(12) United States Patent
Diao et al.

(10) Patent No.: US 10,845,328 B2
(45) Date of Patent: Nov. 24, 2020

(54) NANOPOROUS SEMICONDUCTOR THIN FILMS

(71) Applicant: The Board of Trustees of the University of Illinois, Urbana, IL (US)

(72) Inventors: Ying Diao, Urbana, IL (US); Fengjiao Zhang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 322 days.

(21) Appl. No.: 15/676,617

(22) Filed: Aug. 14, 2017

(65) Prior Publication Data

US 2018/0052136 A1 Feb. 22, 2018

Related U.S. Application Data

(60) Provisional application No. 62/375,475, filed on Aug. 16, 2016.

(51) Int. Cl.
*G01N 27/414* (2006.01)
*H01L 51/05* (2006.01)
(Continued)

(52) U.S. Cl.
CPC ..... *G01N 27/4141* (2013.01); *G01N 27/4146* (2013.01); *G01N 33/0047* (2013.01);
(Continued)

(58) Field of Classification Search
CPC ........... G01N 27/4141; G01N 27/4146; G01N 33/0047; G01N 33/0054; G01N 33/497; G01N 2033/4975; H01L 51/0014; H01L 51/004; H01L 51/0071; H01L 51/0096; H01L 51/0533; H01L 51/0545; H01L 51/0036; H01L 51/0074; H01L 51/0558
See application file for complete search history.

(56) References Cited

U.S. PATENT DOCUMENTS

| 7,479,404 B2 | 1/2009 | Cunningham et al. |
| 7,964,439 B2 | 6/2011 | Kim et al. |
| 2015/0123105 A1* | 5/2015 | Bao ............... H01L 51/0003 257/40 |

FOREIGN PATENT DOCUMENTS

EP 2239561 A1 10/2010

OTHER PUBLICATIONS

Khan, Hadayat Ullah, et al. "Pentacene based organic thin film transistors as the transducer for biochemical sensing in aqueous media." Chemistry of Materials 23.7 (2011): 1946-1953.*
(Continued)

*Primary Examiner* — Robert J Eom
(74) *Attorney, Agent, or Firm* — Haukaas Fortius PLLC; Michael H. Haukaas

(57) ABSTRACT

The present disclosure provides a method of fabricating a nanoporous thin film device comprising depositing a template on a substrate to form a nanoporous insulating layer, the template comprising one or more polymers capable of forming pores when polymerized and at least one crosslinking agent, and depositing a second layer (e.g. organic semiconductor, semiconductor, insulator) on the nonporous insulating layer to form a thin film having a plurality of isolated nanopores on the surface. Nanoporous semiconductor thin films made by these methods is provided. Sensors and devices comprising the nanoporous thin film is also disclosed.

14 Claims, 54 Drawing Sheets

(51) Int. Cl.
*H01L 51/00* (2006.01)
*G01N 33/00* (2006.01)
*G01N 33/497* (2006.01)

(52) U.S. Cl.
CPC ....... *G01N 33/0054* (2013.01); *G01N 33/497* (2013.01); *H01L 51/004* (2013.01); *H01L 51/0014* (2013.01); *H01L 51/0071* (2013.01); *H01L 51/0096* (2013.01); *H01L 51/0533* (2013.01); *H01L 51/0545* (2013.01); *H01L 51/0562* (2013.01); *G01N 2033/4975* (2013.01); *H01L 51/0035* (2013.01); *H01L 51/0036* (2013.01); *H01L 51/0043* (2013.01); *H01L 51/0074* (2013.01); *H01L 51/0558* (2013.01); *Y02A 50/20* (2018.01)

(56) References Cited

OTHER PUBLICATIONS

Roberts, Mark E., et al. "Cross-linked polymer gate dielectric films for low-voltage organic transistors." Chemistry of Materials 21.11 (2009): 2292-2299. (Year: 2009).*

Kang et al., "Enhancing 2D Growth of Organic Semiconductor Thin Films with Macroporous Structures via a Small-molecule Heterointerface," Nature Comm., 5:1-7, Aug. 2014.

Lammertink et al., "Nanostructured Thin Films of Organic-Organometallic Block Copolymers: One-Step Lithography with Poly(ferrocenylsilanes) by Reactive Ion Etching," Adv. Mater., 12(2)98-103, Dec. 1999.

Storm et al., "Fabrication of Solid-state Nanopores with Single-nanometre Precision," Nature Mater., 2:537-540, Jul. 2003.

Yu et al., "Reduction of Thermal Conductivity in Phononic Nanomesh Structures," Nat Nanotechnol., 5(10):718-721, Oct. 2010.

\* cited by examiner

| Before the deposition of DPP-TT | | After the deposition of DPP-TT | |
|---|---|---|---|
| Diameter (nm) | Depth (nm) | Diameter (nm) | Depth (nm) |
| 89.0±10.3 | 20.1±3.7 | 90.5±8.5 | 18.9±2.5 |
| 140.4±15.0 | 22.1±8.5 | 130.8±14.2 | 21.7±3.8 |
| 254.5±12.2 | 31.5±7.6 | 239.6±9.2 | 32.0±8.5 |
| 300.0±16.6 | 33.5±9.5 | 312.0±13.4 | 31.7±6.2 |
| 500.0±6.8 | 35.0±5.6 | 482.0±10.8 | 33.7±11.4 |
| 714.0±15.0 | 38.9±6.8 | 719.2±13.30 | 34.1±12.8 |

Schematic PDMS flow cell

Photo of the sample under detection

Nanopore-template process for nanoporous OSC (in the paper)

Imprint method to control the morphology of OSC

Morphology of DPP2T-TT

PDMS Template

Device Structure: Si/SiO$_2$/nanoporous PVP-HDA/OSC/Au

2DQTT-o-B

LUMO: -4.44 eV   HOMO: -5.59 eV

NANOPOROUS SEMICONDUCTOR THIN FILMS

RELATED APPLICATIONS

This application claims priority under 35 U.S.C. § 119(e) to U.S. Provisional Patent Application No. 62/375,475, filed Aug. 16, 2016, which is incorporated herein by reference.

BACKGROUND OF THE INVENTION

Organic semiconductors (OSC) have emerged as a new class of electronic materials promising a wide range of applications from organic field-effect transistors (OFET), solar cells, thermoelectrics, electronic skins, chemical and mechanical sensors by virtue of their chemical versatility, solution processability and mechanical flexibility. OFET-based chemical sensing presents a combination of advantages including field-effect enabled signal amplification, tunable selectivity and sensitivity by accessing vast chemical and morphological design spaces, as well as solution printability for manufacturing massively deployable low-cost sensor chips which are expected to power the Internet of Things in a foreseeable future.

Reported sensing performances of OFET-based chemical sensors frequently fall short of the high requirements for realizing personalized health and environmental monitoring via detection of volatile organic compounds (VOCs). The VOCs in human breath are strongly correlated with disease conditions ranging from various types of cancer, multiple sclerosis, Parkinson's and Alzheimer's disease, tuberculosis, diabetes, and chronic kidney disease, etc. The disease relevant VOCs in breath, such as ammonia, acetone, nitric oxide, isoprene etc., mostly appear in parts per billion (ppb) levels. On the other hand, OFET sensors with VOC detection limit below 100 ppb are very rarely reported. The response time is also non-ideal, ranging from seconds to minutes. VOCs are also common environmental pollutant, such as formaldehyde, a well-known carcinogenic indoor air pollutant. The National Institute for Occupational Safety and Health (NIOSH) recommends a limit of 16 ppb for long-term occupational exposure, compared to the ppm-level detection limit reported for OFET-based formaldehyde sensors.

Due to the stringent requirement on detection limit, VOC detection and analysis still rely on complex, bulky spectroscopic methods, which are not available to common household. Accordingly, the development of wearable, disposable, ultrasensitive OFET sensors would provide a major impact to VOC detection for personalized health and environmental monitoring.

SUMMARY

This disclosure provides, for the first time, nanoporous organic semiconductor thin films fabricated using simple solution processing methods applicable to both polymer and small molecule semiconductors. The disclosure herein establishes applications involving nanopore-enhanced chemical sensitivity and a doping process.

Templated by a nanostructured layer of poly(4-vinylphenol) (PVP) and 4,4'-(hexafluoroisopropylidene)diphthalic anhydride (HDA), the pore sizes in a semiconductor layer were widely tunable from 50 nm to 1 µm. Thus, introducing nanopores to OFET sensors enhances its reactivity towards VOCs such as ammonia by an order of magnitude, revealed by the reaction model established herein. As a result, the nanopores enabled ultrasensitive, ultrafast response to ammonia down to 1 ppb at hundred-millisecond time scale, which is the best sensing performance reported so far. The generality this strategy was further demonstrated by fabricating nanoporous small molecules for formaldehyde sensing. A 10-fold sensitivity enhancement with unprecedented sensitivity down to 1 ppb was obtained, which is three orders of magnitude better than previous OFET formaldehyde sensors. The excellent performance, simple fabrication, diverse form-factors of nanoporous transistors opens up a wide range of applications in personalized health and environmental monitoring, frequently demanding sensitivity on the ppb level with fast response. The disclosed approach of printing nanoporous thin films could be extended to other material systems and various solution processing methods. Furthermore, the concept of nanoporous organic electronics can bring novel properties beyond chemical sensitivity, such as enhanced mechanical stretchability, new optical properties, and even application in controlled drug release.

Additionally, introducing the porous structure into the organic semiconductors contributes to the doping process after adding the dopant layer in the film device. Given the impact of the pore size and dopant selectivity, the host organic semiconductor could be switched between n- and p-channel with a doping process by fine-tuning the pore structure. Hence, pore structure in the active layer also opens opportunities for modulating the transport of a unipolar material by an effective doping process between p-type, ambipolar and n-type semiconductors. The enhanced-doping properties also benefit to the increase of the carrier mobility as well as film conductivity, which show a bright future in organic electronics, such as field-effect transistors and thermoelectrics.

Accordingly, this disclosure provides a nanoporous semiconducting device comprising:
  a) a substrate having a dielectric layer;
  b) a nanoporous insulating layer comprising one or more insulating polymers that are crosslinked with a crosslinking agent;
  c) a layer comprising an organic semiconductor having a conjugated core,
  wherein the nanoporous insulating layer and the organic semiconductor comprise a plurality of nanopore channels that have an average pore diameter ranging from greater than 0 nm to about 1500 nm, and the conjugated core of the organic semiconductor is oriented parallel to the perimeter of a nanopore channel such that a charge-transfer with an analyte entering the nanopore channel can be facilitated; and
  d) an optional coating at the surface of the organic semiconductor comprising a dopant;
  wherein the plurality of nanopore channels extend from the surface of the organic semiconductor layer, through the nanoporous insulating layer and to the dielectric layer.

This disclosure also provides an organic field-effect transistor (OFET) comprising the above nanoporous semiconducting device, a source electrode, and a drain electrode, wherein the substrate comprises a bottom-gate electrode.

Additionally, a method is described for detecting an analyte, the method comprising:
  a) optionally measuring a baseline current in the described organic field-effect transistor (OFET);
  b) exposing the OFET to a sample comprising an analyte, wherein the analyte interacts with the pi-electrons of the organic semiconductor, thereby causing a change in current; and
  c) detecting a change in the current;

wherein a detectable change in current indicates the presence of the analyte, and wherein the analyte is a small molecule or a macromolecule.

Furthermore, a method of fabricating the disclosed nanoporous semiconducting device is provided, the method comprising:
  a) coating a substrate with a solution to form a film, wherein the solution comprises one or more insulating polymers, a cross-linking agent, and a porogen for inducing nucleation and pore formation;
  b) curing the film to form a nanoporous insulating layer on the substrate;
  c) optionally modifying the hydrophobicity of the surface of the nanoporous insulating layer; and
  d) depositing an organic semiconductor on the surface of the nanoporous insulating layer;

wherein steps a-d result in the formation of a nanoporous semiconducting device having a semiconducting surface area that is higher relative to the semiconducting surface area of semiconducting device lacking a plurality of nanopore channels.

In any of the devices and methods disclosed herein, the ratio of PVP to HDA is about 1:1 to about 20:1.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1A:
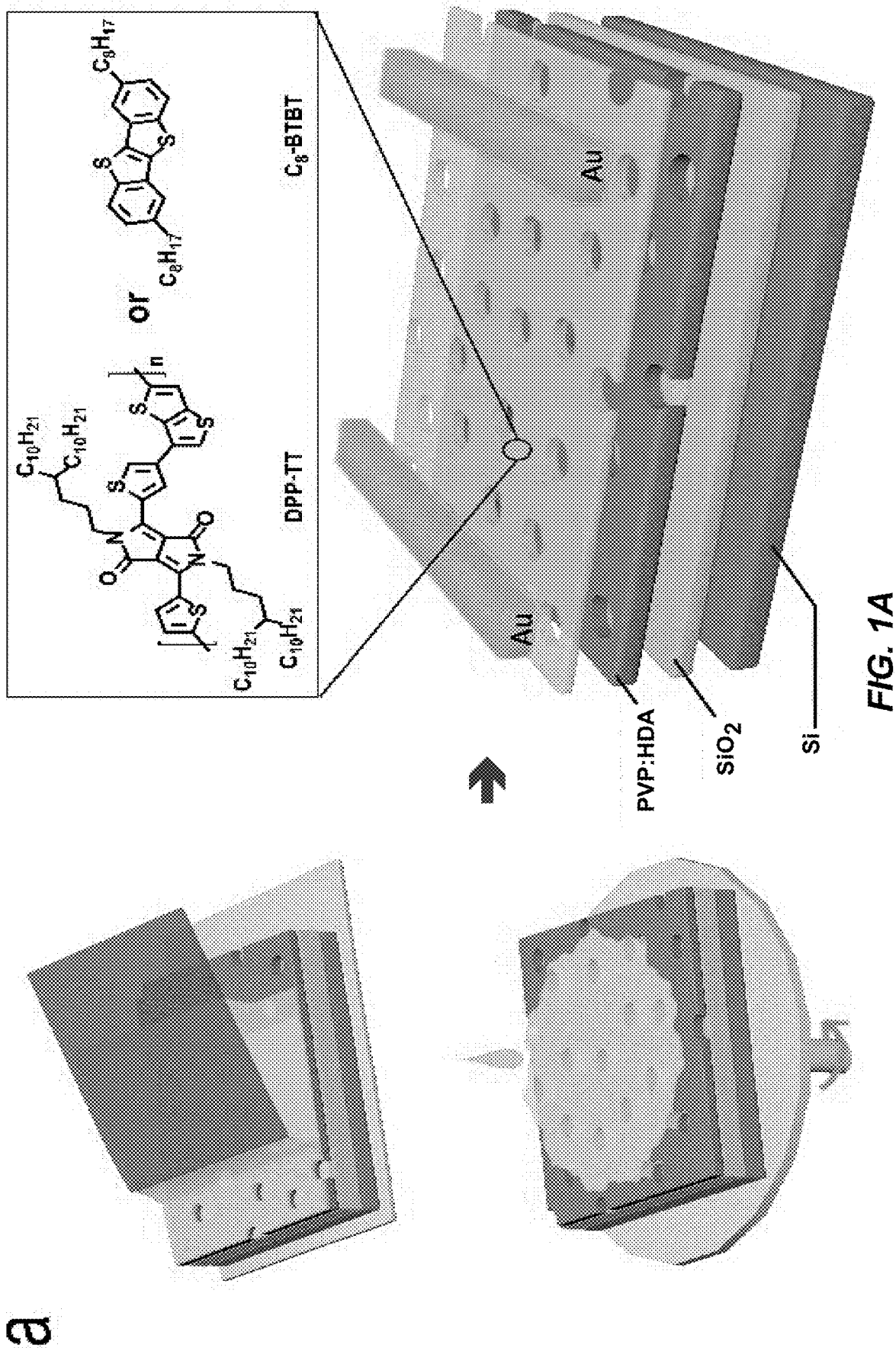
FIG. 1A-1E. Nanoporous semiconductor thin film fabrication via simple solution processing. (a) Schematic of nanoporous semiconductor layer formation templated by a nanoporous PVP:HDA layer via meniscus-guided coating and spin-coating. Also shown is the corresponding nanoporous field-effect transistor device with DPP-TT or $C_8$-BTBT as the active layer, $SiO_2$ as the dielectric layer and doped Si as the gate electrode. (b-e) Atomic Force Microscopy (AFM) height images of porous PVP:HDA templates, with average pore diameter of (b) 0 nm (c) 80 nm, (d) 360 nm, (e) 640 nm. The scale bars are 1 µm in all images.
Figures 1B, 1C, 1D, 1E:
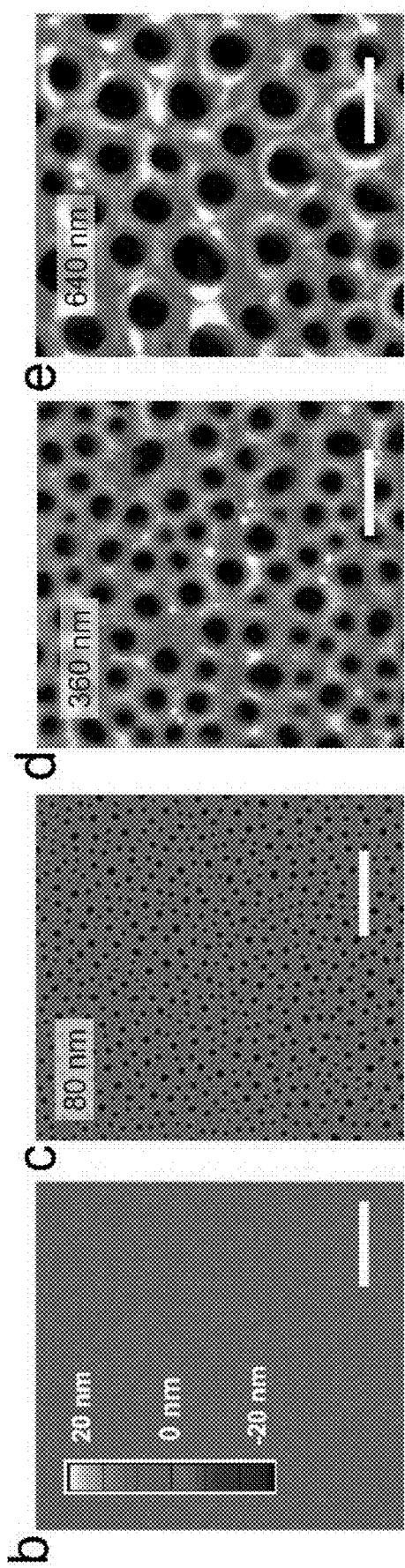

The present disclosure demonstrates a new methodology to enhance chemical sensitivity of OFET based sensors. For the first time, nanopores are introduced with tunable pore sizes into the thin film (e.g. semiconductor thin film) via simple solution processing methods such as meniscus-guided coating and spin-coating. It is noted that introducing porosity to vapor-deposited pentacene thin films has been reported recently by Cho and Oh et al (*Nat. Commun.* 2014, 5, 4752). However, tunable nanoporous OSCs via solution processing has not been demonstrated before. We demonstrate this methodology using both polymer and small molecule semiconductors for ammonia and formaldehyde sensing respectively. We further establish a reaction model to elucidate the mechanism of nanopore-enhanced chemical sensitivity.

The present disclosure also provides a sensor for the improved detection of analytes. For example, introducing nanopores to DPP-TT based OFET sensors enhanced its reactivity towards ammonia by an order of magnitude, revealed by an established reaction model. As a result, the nanopores enabled ultrasensitive, ultrafast response to ammonia down to 1 ppb at hundred-millisecond time scale, which is the best sensing performance reported so far. We further validated the generality of this strategy by fabricating nanoporous $C_8$-BTBT OFET for formaldehyde sensing, a far more challenging sensing target as compared to ammonia due to its low reactivity. Again, we observed a 10-fold sensitivity enhancement with unprecedented sensitivity down to 1 ppb, which is three orders of magnitude improvement over other OFET formaldehyde sensors.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

The term "porogen" refers to a mass of fluidic or solid particles used as is or formed during materials synthesis to make pores in structures for engineering that are dissipate away after the structure has set. An example of a porogen is a marginal solvent.

The term "insulating polymer" refers to a polymer with fully occupied or empty energy bands. Usually insulating polymer has a large energy band gap exceeding 4 electron volts. A insulating polymer can be processed from a solution to form thin layers in the construction of a device. In some instances, an insulating polymer may be used as a dielectric (insulator) in electronic devices. These polymers are also conducive to nanopore formation in a thin film form.

The term "organic semiconductor" refers to organic small molecules or polymers that have semiconducting properties. They are semiconducting because of pi-conjugation and because, for example, the polymer semiconductor has a bandgap of 1 eV to 3 eV. These semiconductors are noninsulating because of a difference in the energy level gap between a semiconductor and an insulator.

Embodiments of the Invention

In various embodiments of this disclosure, a nanoporous semiconducting device comprises:
  a) a substrate having a dielectric layer. The dielectric layer can be, for example, a layer of $SiO_2$ over a substrate of, for example, doped silicon.
  b) a nanoporous insulating layer comprising one or more insulating polymers that are crosslinked with a cross-linking agent;
  c) a layer comprising an organic semiconductor having a conjugated core,
  wherein the nanoporous insulating layer and the organic semiconductor comprise a plurality of nanopore channels that have an average pore diameter ranging from greater than 0 nm to about 1500 nm. The conjugated core of the organic semiconductor is oriented parallel to the perimeter of a nanopore channel such that a charge-transfer with an analyte entering the nanopore channel can be facilitated. In other words, the pi-orbitals of the conjugated core would be facing toward the interior of the nanopore channel where the pi-orbitals would be exposed to interacting with the analyte; and
  d) an optional coating at the surface of the organic semiconductor comprising a dopant;
  wherein the plurality of nanopore channels extend from the surface of the organic semiconductor layer, through the nanoporous insulating layer and to the dielectric layer. In various embodiments, the plurality of nanopore channels are substantially oriented orthogonal relative to the substrate within the nanoporous semiconducting device.

This disclosure includes various embodiments of an organic field-effect transistor (OFET) comprising the nanoporous semiconducting device, a source electrode, and a drain electrode, wherein the substrate comprises a bottom-gate electrode.

In some embodiments, the insulating polymer comprises poly(4-vinylphenol) (PVP), polystyrene (PS), poly(vinylpyrrolidone), benzocyclobutene, polyethylene oxide (PEO), poly(methyl methacrylate) (PMMA), PS-b-PMMA, PS-r-PMMA, PS-b-PMMA-b-PEO, poly(styrene-b-butadiene), poly(styrene-b-2-vinyl pyridine-b-t-butyl methacrylate), PS-b-PEO, poly(iso-b-lactide), poly(styrene-b-4-vinylpyridine), poly(vinylidene fluoride-co-hexafluoropropylene), or a combination thereof. The insulating polymer can be simple derivatives of the insulating polymers, for example, the repeating unit would have a $C_1$-$C_8$(alkyl) substituent, a halogen substituent, a hydroxyl substituent, a methoxy substituent, an ethoxy substituent, or an amine substituent.

In other embodiments, the cross-linking agent comprises 4,4'-(hexafluoroisopropylidene) diphthalic anhydride (HDA), benzophenone-3,3',4,4'-tetracarboxylic dianhydride (BCD), ethylenediaminetetraacetic dianhydride (EAD), diethylenetriaminepentaacetic dianhydride (DAPD), 3,3',4,4'-biphenyltetracarboxylic dianhydride (BPD), biphenyl-4,4'-dicarboxylic acid (BCA), suberic acid (SA), suberoyl chloride (SC), terephthaloyl chloride, di-acylchloride (daCl), divinylbenzene (DVB), poly(ethylene glycol) dimethacrylate, or a combination thereof.

In the above embodiments, the ratio of PVP to HDA is about 1:1 to about 20:1, about 10:1, about 20:3, about 5:1, about 4:1, about 10:3, about 20:7, about 5:2, about 20:9, about 2:1, about 20:11, about 5:3, about 20:13, about 10:7, about 4:3, about 5:4, about 20:17, about 10:9, or about 20:19.

In other various embodiments, the organic semiconductor comprises a small molecule wherein the small molecule is a benzothieno[3,2-b]benzothiophene (BTBT), a dinaphthothieno[3,2-b]thiophene (DNTT), a perplene diimide (PDI), a naphthalene diimide (NDI), a quinoidal terthiophene (DQTT), a phenyl-butyric acid methyl ester, a buckminsterfullerene (C60), a pentacene, a rubrene, or a combination thereof.

In yet other embodiments, the organic semiconductor comprises a semiconducting polymer wherein the semiconducting polymer is poly(diketopyrrolopyrrole-thiophene-thieno[3,2,b]thiophene-thiophene) (DPP-TT), poly[2,5-bis(alkyl)pyrrolo[3,4-c]pyrrole-1,4(2H, 5H)-dionealt-5,5'-di(thiophen-2-yl)-2,2'-(E)-2-(2-(thiophen-2-yl)vinyl)thiophene] (PDVT), a isoindigo polymer (PII), a polythiophene, poly(2,5-bis(3-alkylthiophen-2-yl) thieno[3,2-b]thiophene) (PBTTT), poly[5,5'-bis(3-alkyl-2-thienyl)-2,2'-bithiophene] (PQT), benzothienobenzothiophene thiophene copolymer (PBTBT), poly{[N,N9-bis(2-octyldodecyl)-naphthalene-1,4,5,8-bis(dicarboximide)-2,6-diyl]-alt-5,59-(2,29-bithiophene)} (PNDI2OD-TT), N,N-di(2-ethylhexyl)-3,4,9,10-perylene diimide-1,7-diyl (PDTP-PDI), poly{N-[1-(2-ethylhexyl)-3-ethylheptanyl]-dithieno[3,2-b:20,30-d]pyrrole-3,6-dithien-2-yl-2,5-di(2-ethylhexyl)-pyrrolo[3,4-c]pyrrole-1,4-dione-50,500-diyl (PDTP-DTPDI), poly[4-(4,4-dihexadecyl-4H-cyclopenta[1,2-b:5,4-b']dithiophen-2-yl)-alt-[1,2,5]thiadiazolo-[3,4-c]pyridine] (PCDTPT), or a combination thereof. The organic semiconductors can be simple derivatives of semiconducting small molecules or simple derivatives of semiconducting polymers, for example, the core of the small molecule or the repeating unit of the polymer would have a $C_1$-$C_8$(alkyl) substituent, a halogen substituent, a hydroxyl substituent, a methoxy substituent, an ethoxy substituent, or an amine substituent.

In various embodiments, the dopant is present and the dopant comprises, but is not limited to 7,7,8,8-tetracyano-2,3,5,6-tetrafluoroquinodimethane (F4-TCNQ), dihydro-1H-benzoimidazol-2-yl, polyethylenimine (PEI), tris(pentafluorophenyl)borane (TPFB), graphene oxide (GO), (tridecafluoro-1,1,2,2-tetrahydrooctyl)trichlorosilane, (tridecafluoro-1,1,2,2-tetrahydrooctyl)triethoxysilane, n-octyltrichlorosilane, 4-trifluor-omethyl-benzenethiol, tetrathianaphthacene, bis(cyclopentadienyl)-cobalt(II), complexes of 1,3,4,6,7,8-hexahydro-2H-pyrimido[1,2-a]pyrimidine (hpp), or a combination thereof. The dopant can be used for p-type nanoporous semiconductors and n-type nanoporous semiconductors This disclosure embodies methods of detecting an analyte. The method comprises:
  a) optionally measuring a baseline current in the organic field-effect transistor (OFET) disclosed above;
  b) exposing the OFET to a sample comprising an analyte, wherein the analyte interacts with the pi-electrons of the organic semiconductor, thereby causing a change in current; and
  c) detecting a change in the current;
  wherein a detectable change in current indicates the presence of the analyte, and wherein the analyte is a small molecule or a macromolecule.

In various embodiments, the limit of detection is as low as about 1 part per billion. In other embodiments, the total surface area of the plurality of nanopore channels in the nanoporous semiconducting device as a fraction of the total surface area of the organic semiconductor layer is proportional to the sensitivity of detection.

In some embodiments, the analyte donates electrons to a p-type nanopore channel to decrease current, or the analyte accepts electrons from a p-type nanopore channel to increase current. In some other embodiments, the analyte donates electrons to a n-type nanopore channel to increase current, or the analyte accepts electrons from an n-type nanopore channel to decrease current.

In other various embodiments, the OFET comprises a dopant, and the dopant can donate electrons to the organic semiconductor, or accept electrons from the organic semiconductor, thereby forming a charge-transfer complex having a charge carrier concentration at the organic semiconductor. In additional embodiments, the analyte reacts with the dopant thereby changing the charge carrier concentration at the organic semiconductor and changing the source-drain current of the OFET.

Embodiments of this disclosure provides, a method of fabricating the nanoporous semiconducting device, the method comprising:
  a) coating a substrate with a solution to form a film, wherein the solution comprises one or more insulating polymers, a cross-linking agent, and a porogen for inducing nucleation and pore formation;
  b) curing the film to form a nanoporous insulating layer on the substrate;
  c) optionally modifying the hydrophobicity of the surface of the nanoporous insulating layer; and
  d) depositing an organic semiconductor on the surface of the nanoporous insulating layer;
  wherein steps a-d result in the formation of a nanoporous semiconducting device having a semiconducting surface area that is higher relative to the semiconducting surface area of semiconducting device lacking a plurality of nanopore channels.

In yet other additional embodiments, the porogen comprises tetrahydrofuran (THF), propylene glycol monomethyl ether acetate (PGMEA), dimethylformamide (DMF), dimethyl sulfoxide (DMSO), chloroform, chlorobenzene, dichlorobezene, acetone, acetonitrile, ethanol, isopropanol, or a combination thereof.

In various embodiments, the average pore diameter is tuned by modifying the ratio of PVP to HDA, wherein increasing HDA relative to PVP increases the average pore diameter. In other embodiments, a substrate is coated with the film by performing, for example, spin coating, drop casting, meniscus guided coating, roll-to-roll printing, flexographic printing, slot-die coating, gravure printing, bar-coating, screen printing, ink-jet printing, pen-writing, spray coating, transfer printing, contact printing, or laser printing.

In various other embodiments, the substrate is a flexible substrate, a rigid substrate, or a combination thereof. The substrate optionally comprises $SiO_2$, $Al_2O_3$, $HfO_2$, $V_2O_5$, TiO, an insulating polymer, divinyltetramethyldisiloxane-bis(benzocyclobutene) (BCB), or tetratetracontane.

Results and Discussion

The following features were found to be important for enhanced sensitivity of nanoporous OFETs: 1) the pores are through-pores to grant access to the highly reactive conducting channel at the semiconductor-dielectric interface; 2) the conjugated core of the semiconductor is oriented parallel to the pore wall to facilitate charge-transfer reaction with the analyte. The excellent performance, simple fabrication, diverse form-factors of nanoporous transistors opens a wide range of applications in personalized health and environmental monitoring, frequently demanding sensitivity on the ppb level with fast response. Our approach of printing nanoporous thin films could be extended to other material systems and various solution processing methods. Furthermore, the concept of nanoporous organic electronics can bring novel properties beyond chemical sensitivity, such as enhanced mechanical stretchability, new optical properties, and even application in controlled drug release.

Figures 31A, 31B:
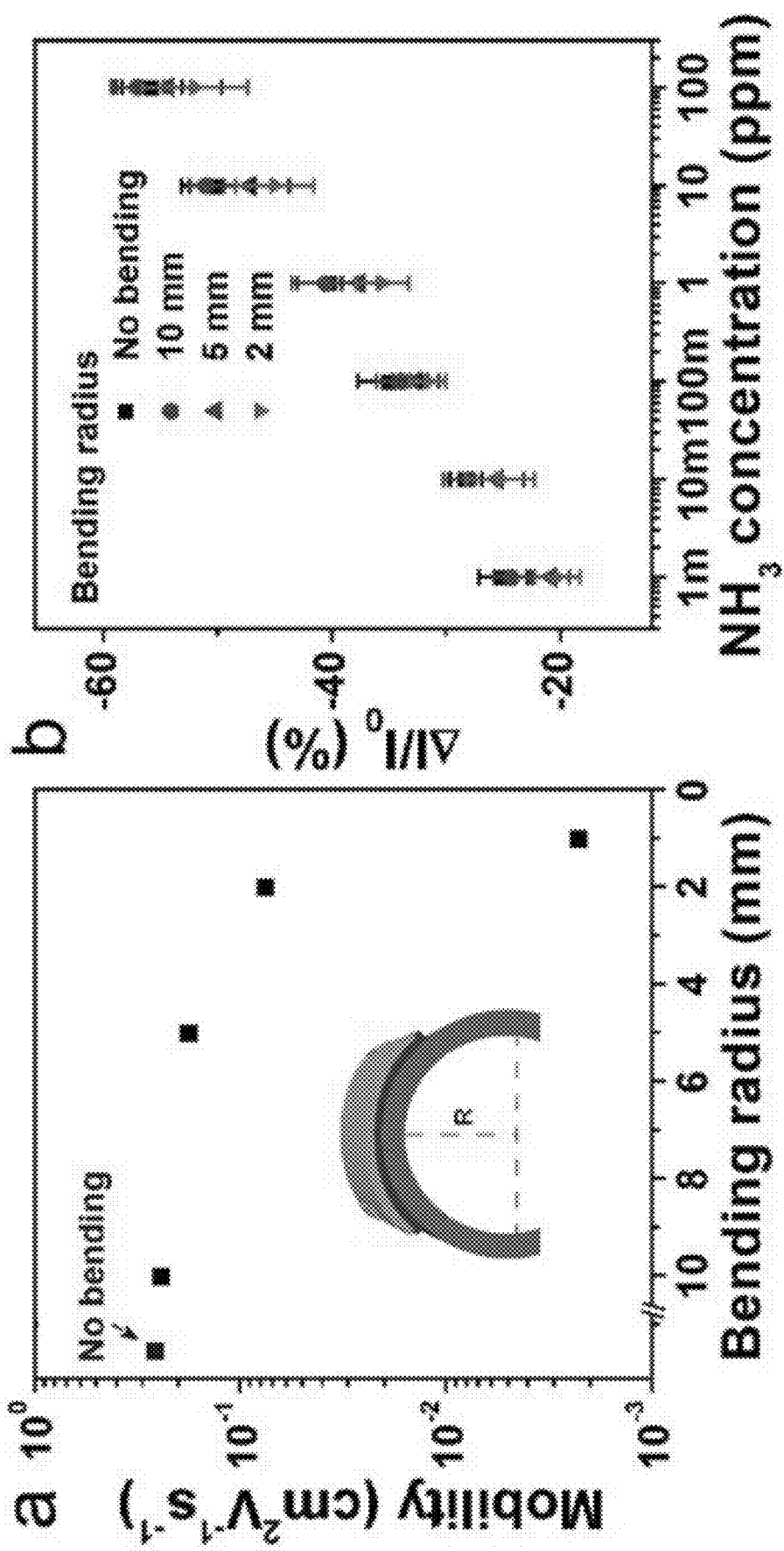
FIG. 31A-31B. Effect of bending on mobility and sensitivity to ammonia. (a) Impact of bending radius on charge carrier mobility of the flexible DPP-TT devices during outward bending. The insert shows the illustration of a bent OFET. (b) Sensitivity of nanoporous DPP-TT sensors with various bending radius.

In one aspect, a method of fabricating a nanoporous thin film is provided, the method comprising depositing a template on a substrate to form a nanoporous insulating layer, the template comprising one or more polymers capable of forming pores when solidified and with or without at least one cross-linking agent, and depositing a second layer on the nanoporous insulating layer to form a thin film having a plurality of isolated nanopores on the surface. In one embodiment, the second layer is selected from a semiconductor, an organic semiconductor and an insulator. The template comprises one or more polymers (e.g. PVP) that can form nanopores when polymerized by a cross-linking agent (e.g. HDA) and deposited on the substrate. The structures of the polymers are such that when they solidify, natural pores are formed, as depicted in FIG. 31. So, when the template is deposited on a substrate by solution processing methods, it forms a template later having nanopores that are through pores all the way to the substrate layer. The size of the pores on the template can be tuned by altering the ratio of PVP:HDA (FIG. 8 and Table 1). When a second layer (e.g. organic semiconductor, semiconductor, insulator) is deposited on the template, it forms nanopores. When the substrate is a gate electrode with a dielectric layer, and the second layer is a semiconductor or organic semiconductor, the floor of the nanopores of the semiconductor layer is in contact with the dielectric. When an electrode is deposited on the surface of the organic semiconductor, analytes can be detected using this sensor. Analytes in a sample (e.g. gas) diffuse into the nanopores, and donate or accept electrons with the semiconductor in the pore, thereby changing the hole concentration and resulting in changes in currents that can be detected by the electrodes. The concentration of an analyte can be quantified based on the electrical current changes.

Figures 43A, 43B:
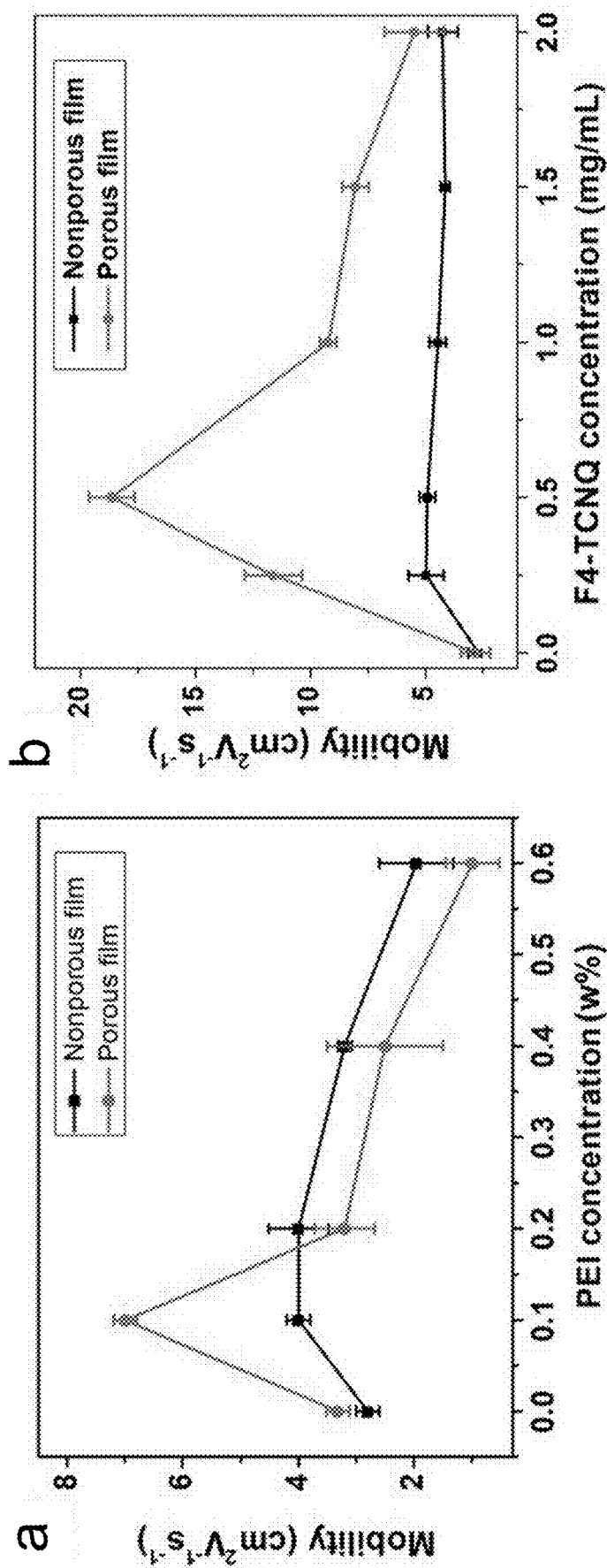
FIG. 43A-43B. Charge carrier mobility of thin films doped with (a) PEI and (b) F4-TCNQ as a function of doping concentration.
Figure 44:
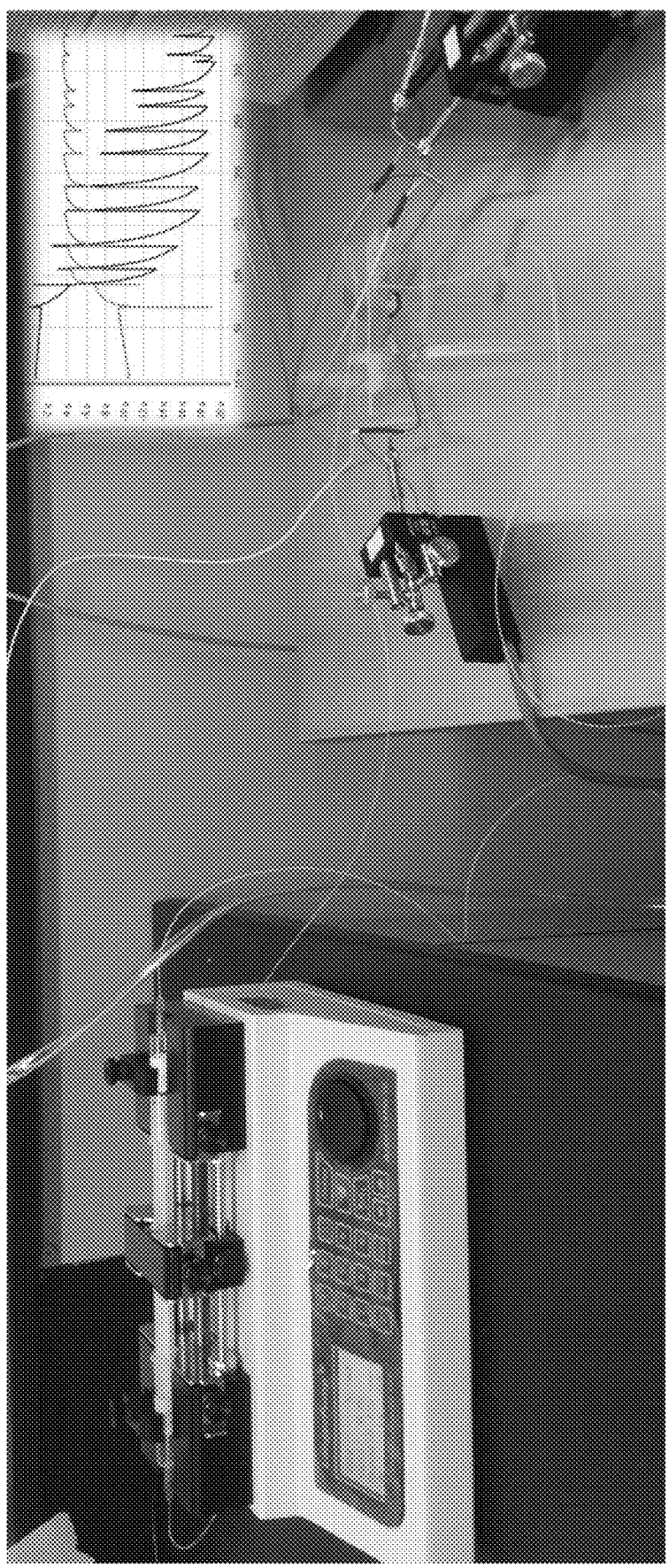
FIG. 44. Apparatus system for gas monitoring.
Figure 45A:
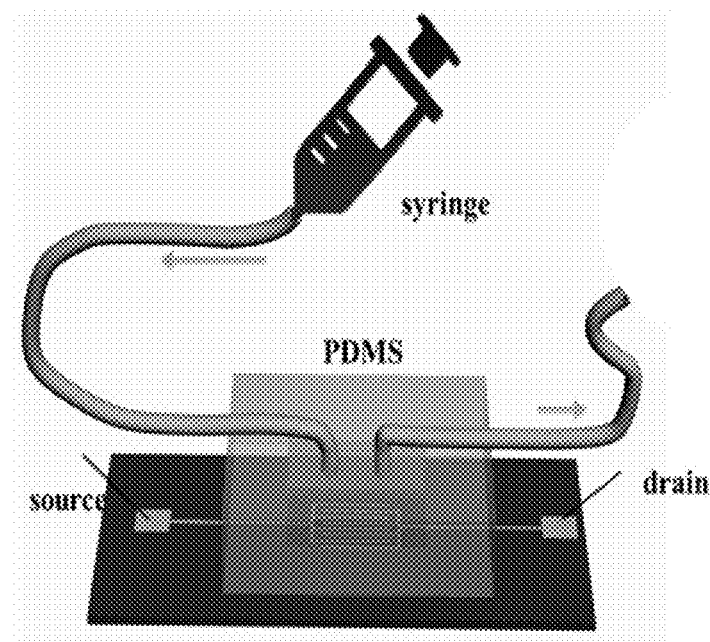
FIG. 45A-45B. PDMS flow cell. (a) Schematic for PDMS flow cell. (b) Photo of sample under detection.
Figure 45B:
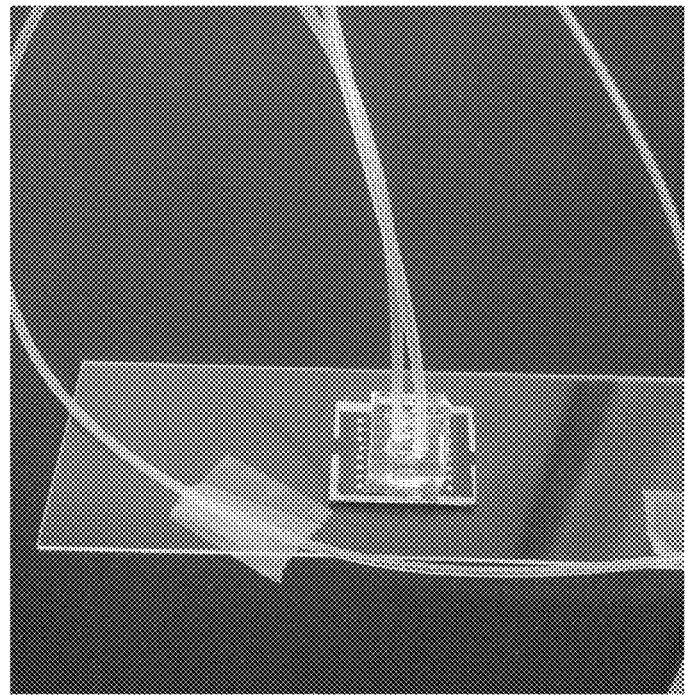
Figure 46A:
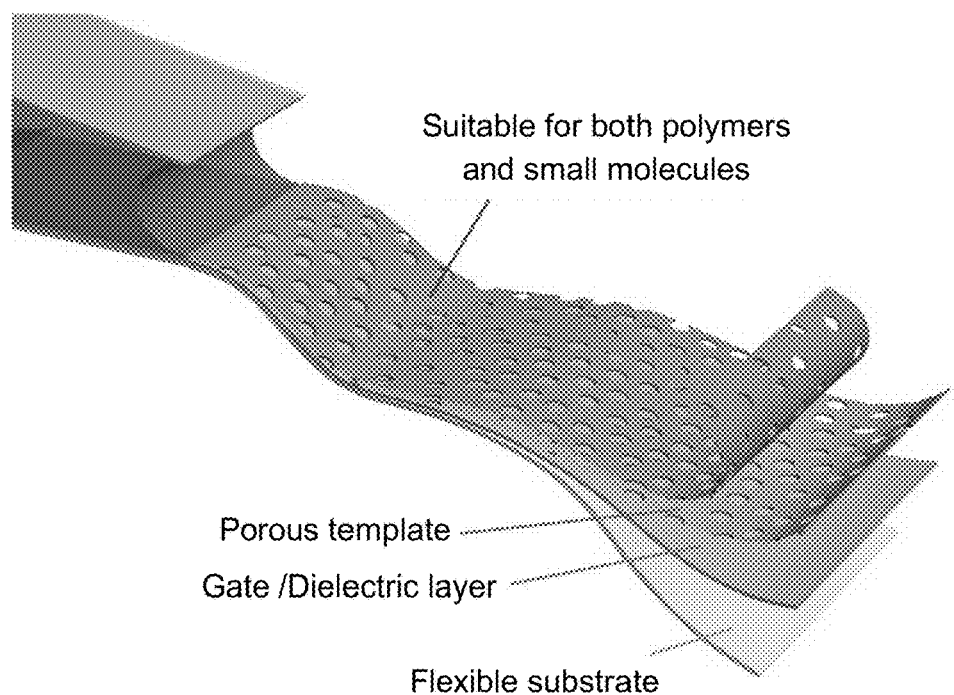
FIG. 46A-46B. Two methods for microstructure construction in an organic semiconductor film. (a) Nanopore-template process for nanoporous OSC. (b) Imprint method to control the morphology of OSC.
Figure 46B:
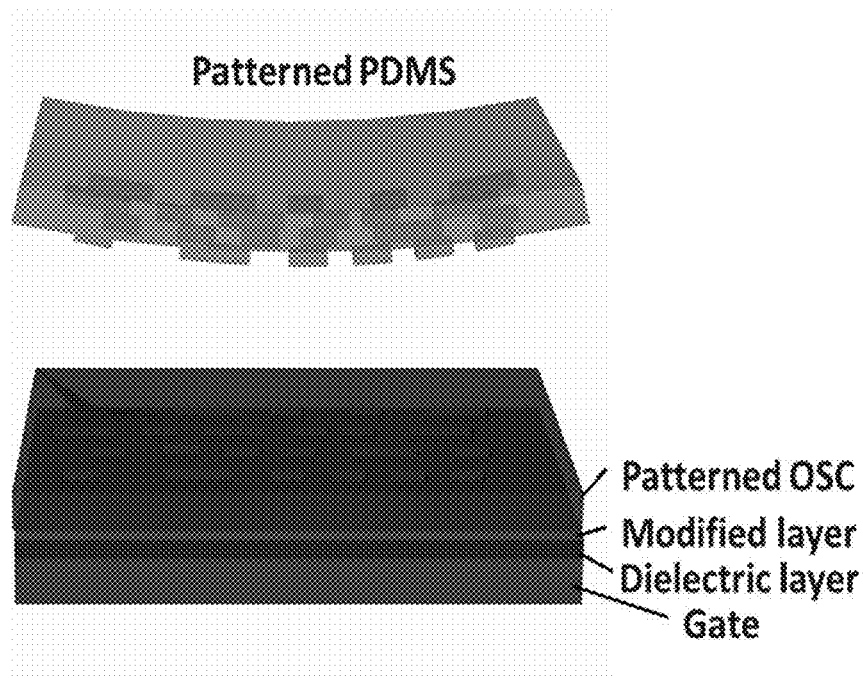
Figure 47B:
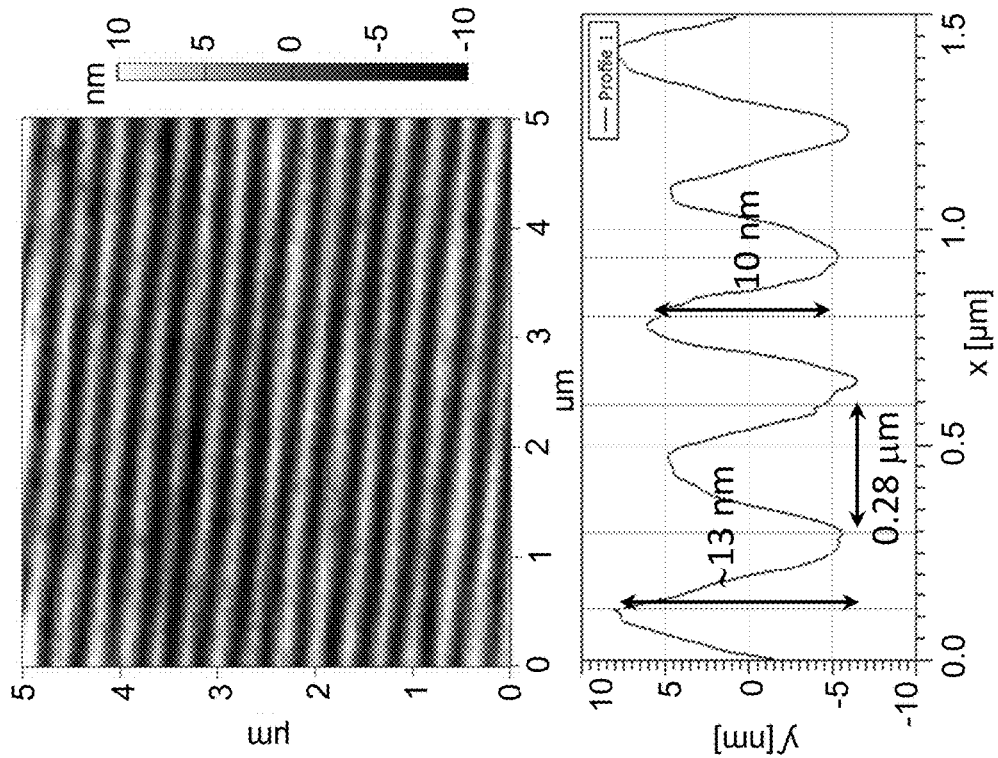
FIG. 47A-47B. PDMS template prepared with Blue-ray disc. (a) PDMS template. (b) Morphology of DPP2T-TT.
Figure 47A:
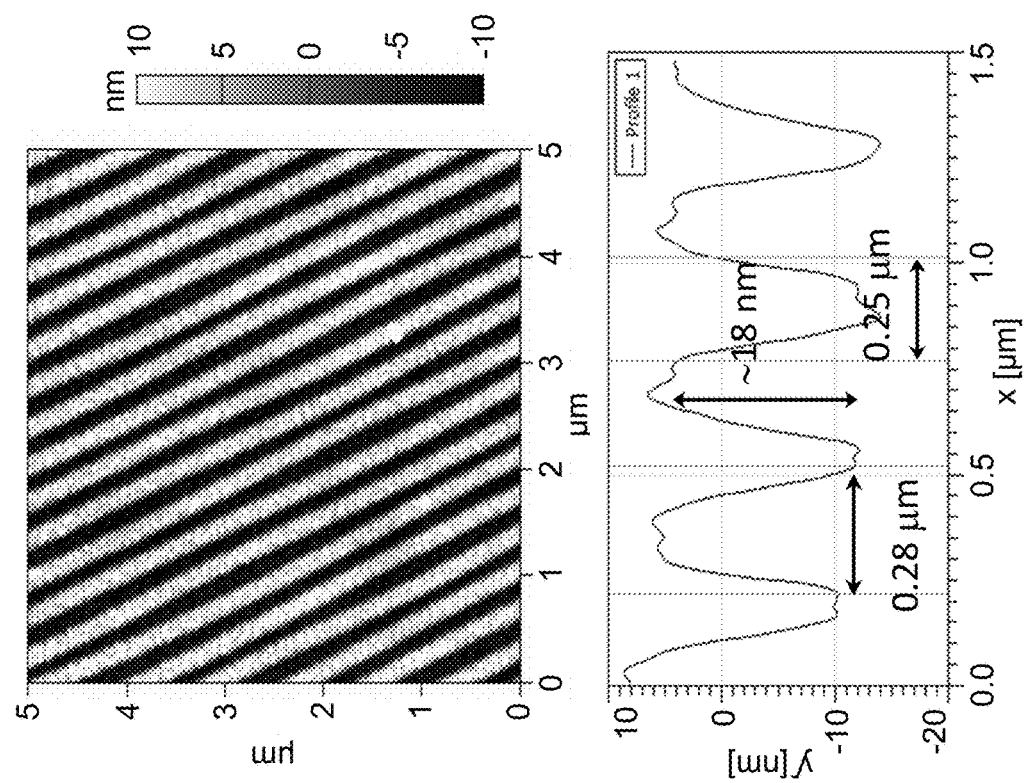
Figure 48:
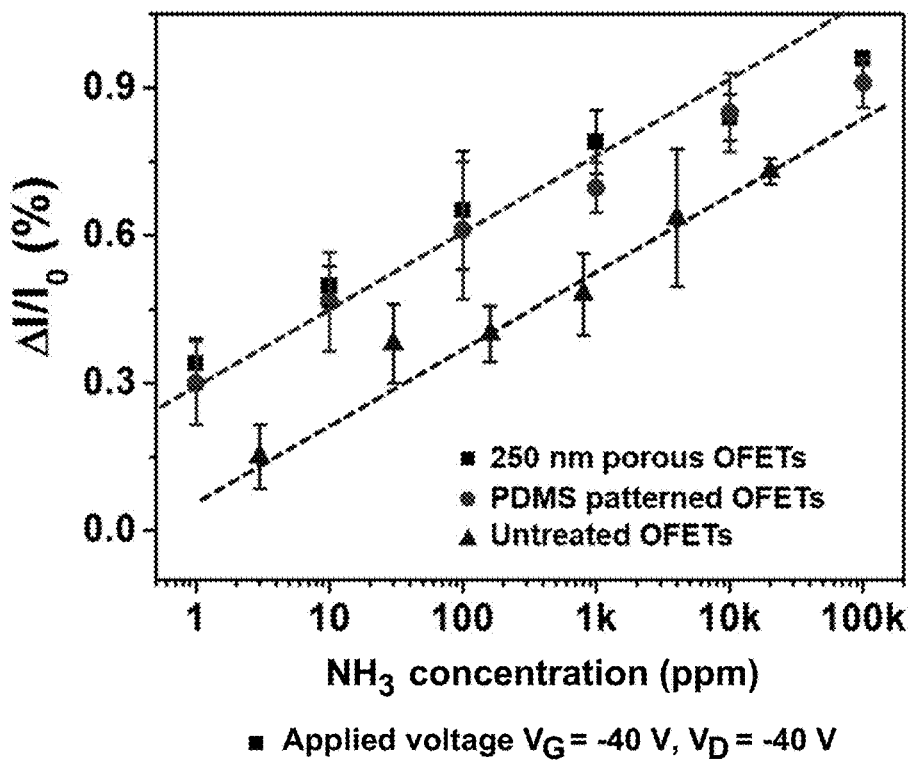
FIG. 48. Sensing performance comparison.
Figure 49:
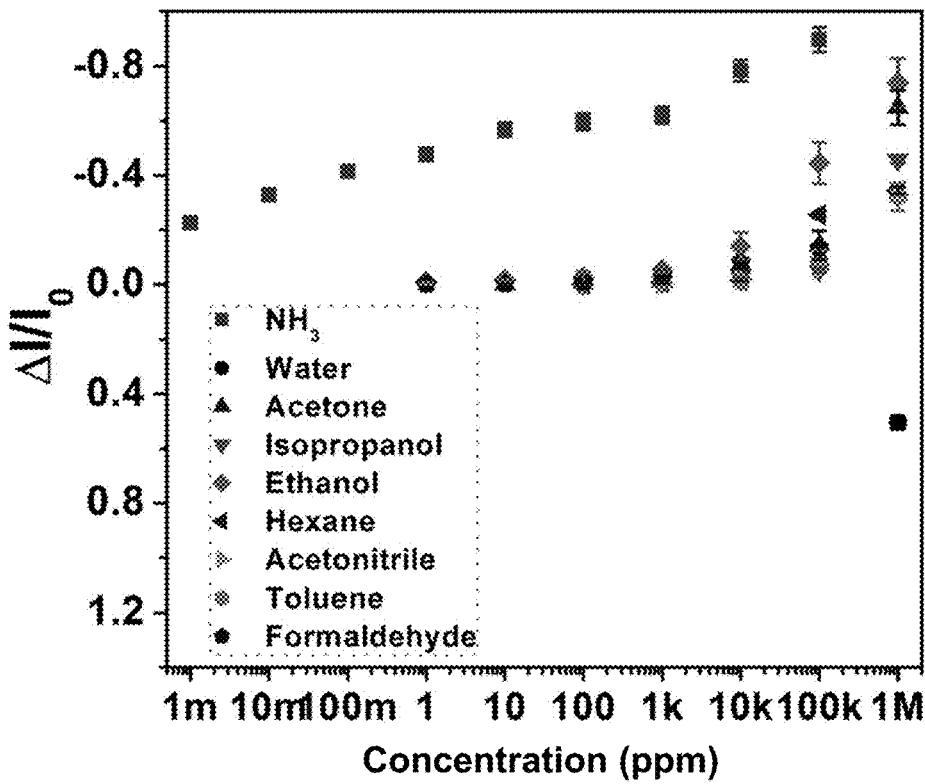
FIG. 49. Sensing performance with air as carrier gas.
Figure 50:
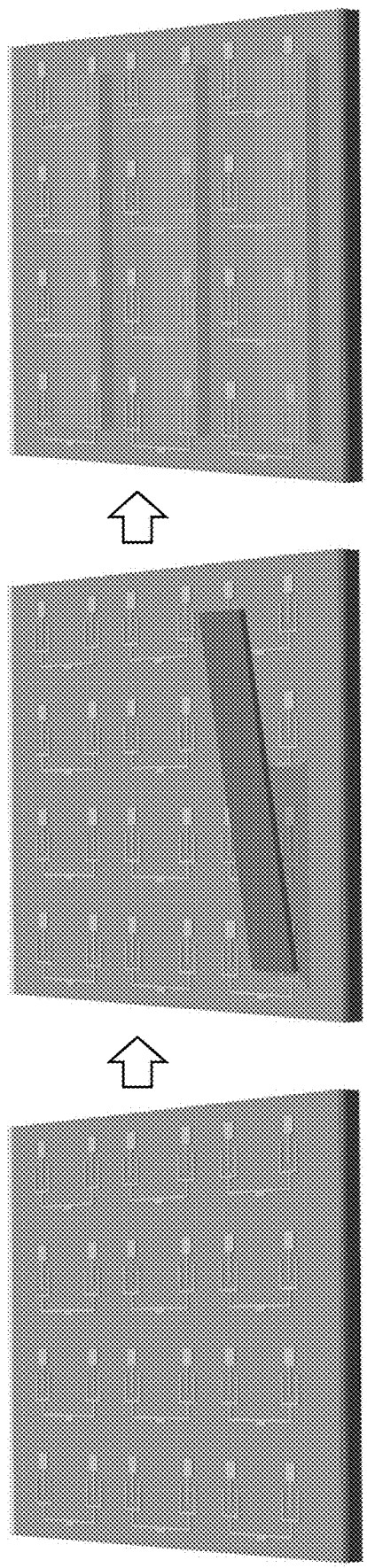
FIG. 50. Printed PEI layer for patterned doping.
Figure 51:
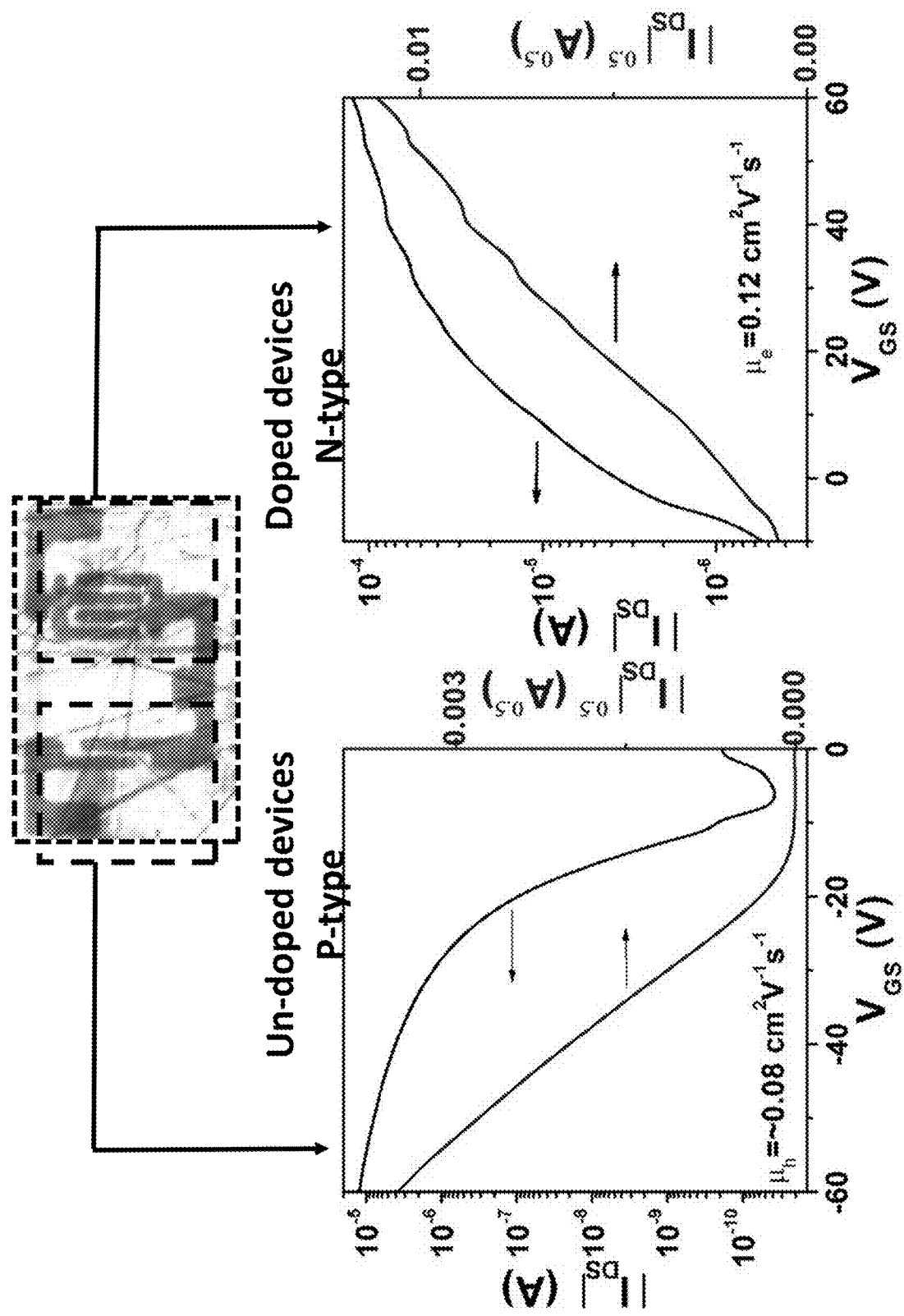
FIG. 51. Patter doped ambipolar devices.
Figure 52:
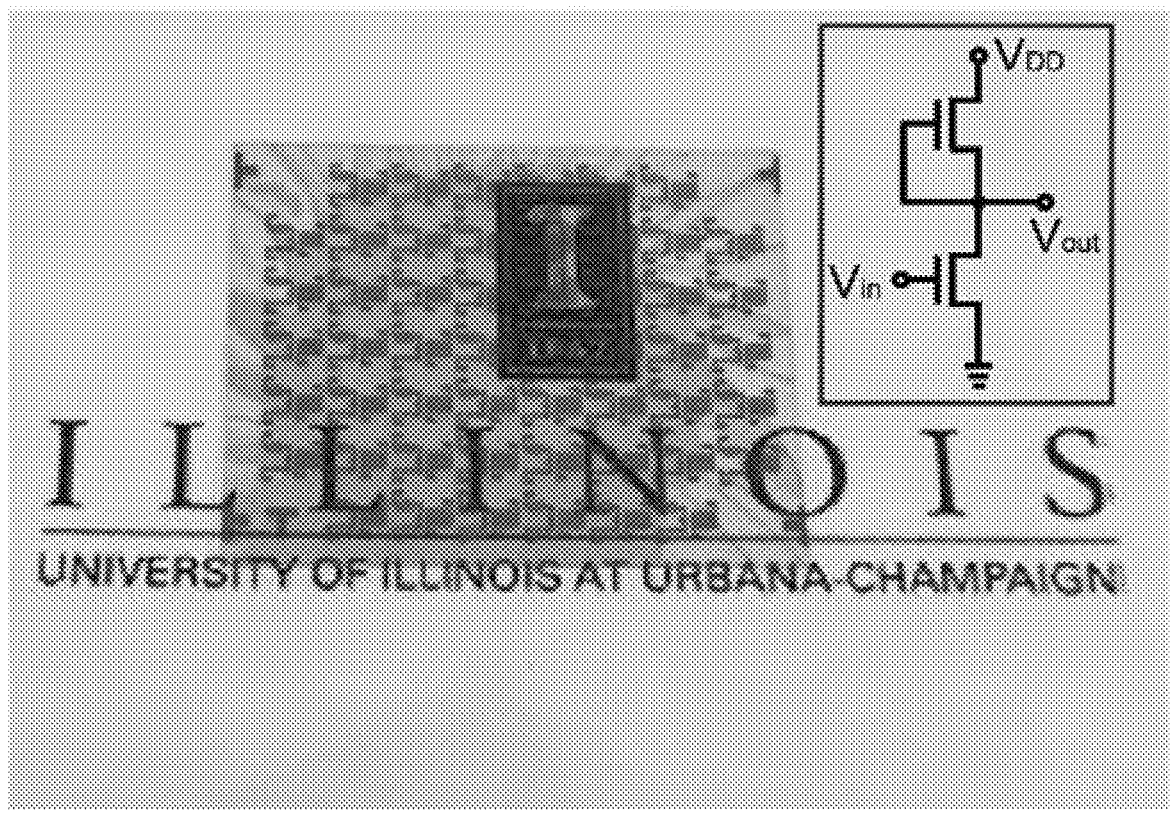
FIG. 52. Doping induced inverter.
Figure 53:
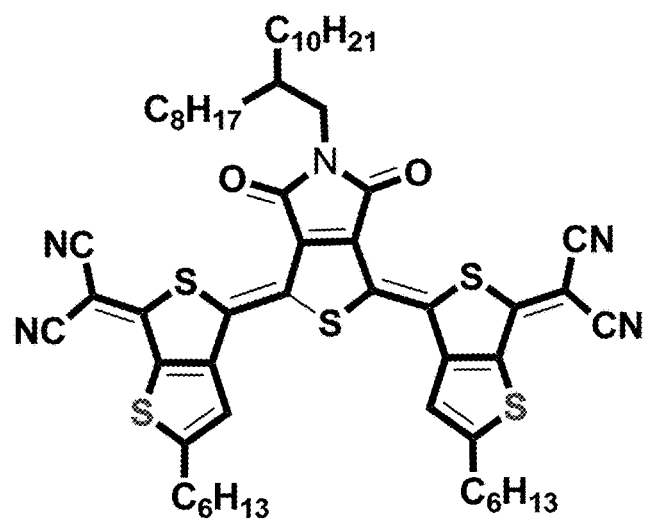
FIG. 53. N-type porous OFETs: 2DQTT-o-B. 2DQTT-o-B was spin-coated. The device was fabricated after 100° C. thermal annealing of the film.
Figure 54:
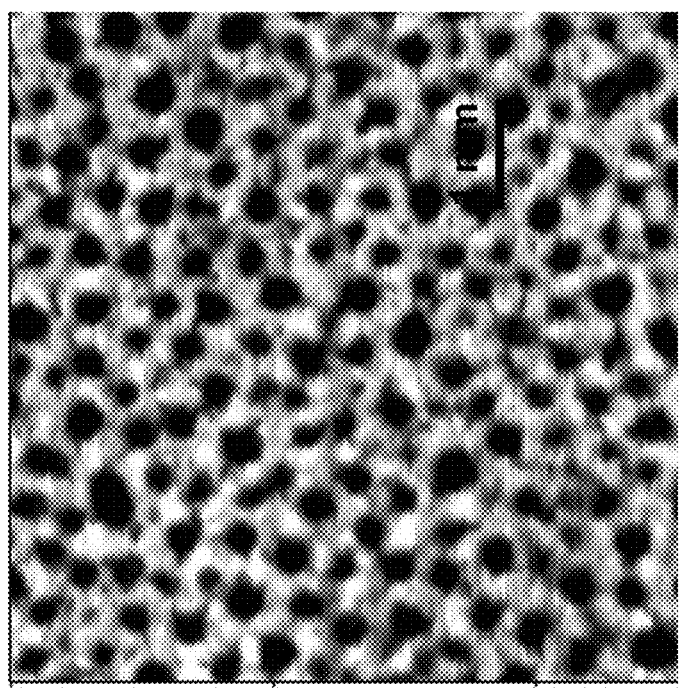
FIG. 54. Morphology of 2DQTT-o-B films. (a) OSC on nonporous substrate. (b) OSC on porous PVP:HDA template. The random holes occur on annealed films, even though using a flat substrate. However, the controllable nanoporous structure can be transferred from template to 2DQTT-o-B film.
Figure 54:
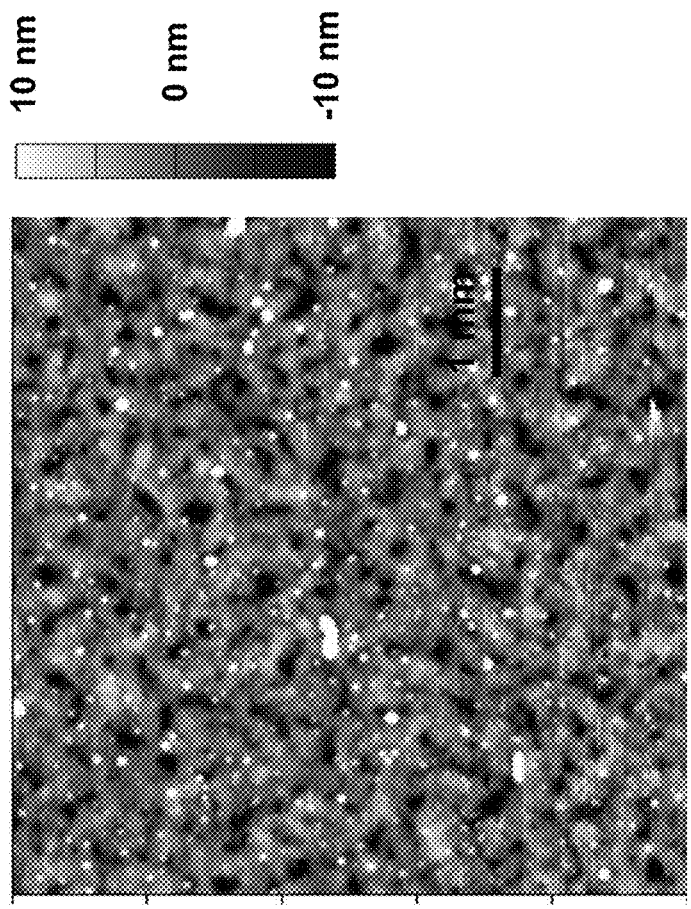
Figures 55A, 55B, 55C:
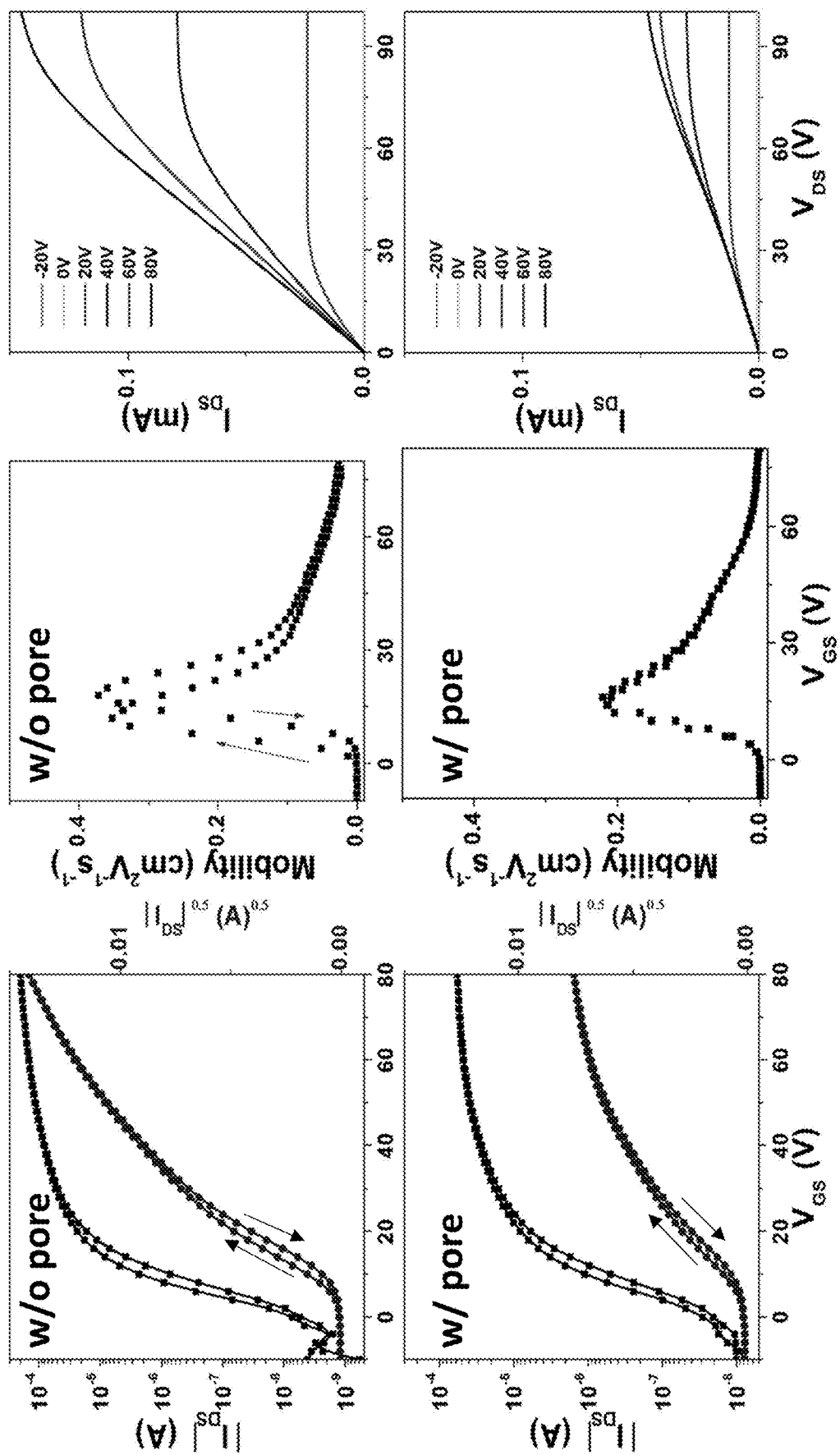
FIG. 55A-55C. Characteristic curves for nanoporus 2DQTT-o-B films
Figure 56A:
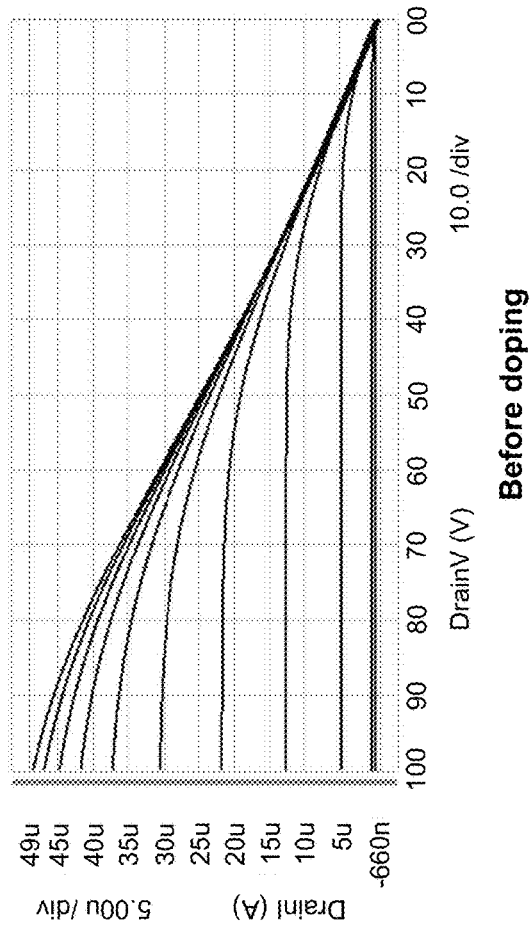
FIG. 56A-56B. N-type doping enhanced conductivity. (a) Significant change on conductivity—before and after doping with 0.2 wt % PEI. (b) Table showing 2DQTT-o-B film conductivity before and after doping.
Figure 56B:
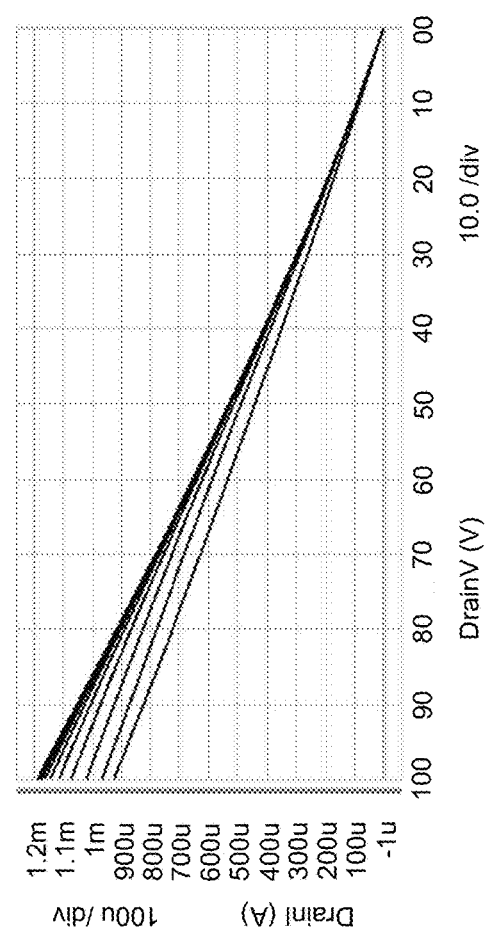

Coating the semiconductor or organic semiconductor with various dopants can increase the sensitivity and/or specificity of the sensor. Doping is independent of the sensing application. The nanoporous structure can enhance doping efficiency, and therefor can increase the performance of the semiconductor, such as enhancing the charge carrier mobility (FIG. 43) and conductivity. The enhance performance of the thin films can benefit the transistor, inverter, sensors, thermoelectric applications and other devices having the thin films.

It should be noted that although several examples show the methods being used to make organic semiconductor thin films, the method could be used to make other thin films as well, for example semiconductors and insulators.

In another aspect, a nanoporous thin film made from any of the methods described herein is provided.

In another aspect, sensors are provided, the sensors comprising the nanoporous thin films described herein. Devices comprising sensors and thin films described herein are also provided. The devices may further comprise a microfluidic system enclosing the sensor to help draw the sample to be tested to the thin film. In another aspect, the sensors are flexible and wearable. These sensors and devices made using the methods described herein can be used to for the detection of any analyte of interest by altering the semiconductor or organic semiconductor layer, the pore sizes, and/or the dopants.

TABLE 1

Ratio of polymer to cross linking agent on pore diameter

| PVP:HDA Ratio | 20:1 | 20:3 | 20:4 | 20:6 | 20:8 | 20:10 | 20:15 |
|---|---|---|---|---|---|---|---|
| Pore diameter (nm) | 0 | 100 | 280 | 300 | 500 | 510 | 700 |

Template

A template comprises one or more polymers that can naturally form nanopores upon polymerization including, but is not limited to, poly(4-vinylphenol), polystyrene (PS), poly(vinylpyrrolidone), benzocyclobutene, polyethylene oxide (PEO), poly(methyl methacrylate) (PMMA), block copolymer such as PS-b-PMMA, PS-r-PMMA, PS-b-PMMA-b-PEO, poly(styrene-b-butadiene), poly(styrene-b-2-vinyl pyridine-b-t-butyl methacrylate), PS-b-PEO, poly(iso-b-lactide), and poly(styrene-b-4-vinylpyridine).

Cross Linking Agent.

The cross linking agent of the present disclosure includes, but is not limited to, 4,4'-(hexafluoroisopropylidene)diphthalic anhydride (HDA), benzophenone-3,3',4,4'-tetracarboxylic dianhydride (BCD), ethylenediaminetetraacetic dianhydride (EAD), diethylenetriaminepentaacetic dianhydride (DAPD), 3,3',4,4'-biphenyltetracarboxylic dianhydride (BPD), biphenyl-4,4'-dicarboxylic acid (BCA), suberic acid (SA), and suberoyl chloride (SC), terephthaloyl chloride, di-acylchloride (daCl), divinylbenzene (DVB), and poly(ethylene glycol) dimethacrylate.

Dopant

The dopant can be a material having a redox or charge transfer reaction with semiconductors or organic semiconductors. The dopants always have a stronger electron-withdrawing or electron-donating ability. These dopants includes, but not limited to, 7,7,8,8-Tetracyano-2,3,5,6-tetrafluoroquinodimethane (F4-TCNQ), polyethylenimine (PEI), tris(pentafluorophenyl)borane (TPFB), graphene oxide (GO), (tridecafluoro-1,1,2,2-tetrahydrooctyl)trichlorosilane, (tridecafluoro-1,1,2,2-tetrahydrooctyl)triethoxysilane and n-octyltrichlorosilane, 4-trifluor-o-methyl-benzenethiol. The dopants can also be organic complexes with a very high HOMO level or a low LUMO, such as tetrathianaphthacene, bis(cyclopentadienyl)-cobalt(II), the di-metal complexes of chromium or tungsten with the anion of 1,3,4,6,7,8-hexahydro-2H-pyrimido[1,2-a]pyrimidine (hpp). The acid-base can also be used as dopants here.

Organic Semiconductor Polymers

The organic semiconductor polymer can include, but not limited to, poly(diketopyrrolopyrrole-thiophene-thieno[3,2,b]thiophene-thiophene) (DPP-TT) or other donor-acceptor copolymer with the diketopyrrolopyrrole (DPP) unit, poly[2,5-bis(alkyl)pyrrolo[3,4-c]pyrrole-1,4(2H, 5H)-dionealt-5,5'-di(thiophen-2-yl)-2,2'-(E)-2-(2-(thiophen-2-yl)vinyl) thiophene] (PDVT5), isoindigo based polymers (PIIs), polythiophene, poly(2,5-bis(3-alkylthiophen-2-yl) thieno[3,2-b]thiophene) (PBTTT), poly[5,5'-bis(3-alkyl-2-thienyl)-2,2'-bithiophene] (PQT), benzothienoben-zothiophene thiophene copolymer (PBTBT), naphthalene diimides or perplene diimide units based polymer including poly{[N,N9-bis(2-octyldodecyl)-naphthalene-1,4,5,8-bis(dicarboximide)-2,6-diyl]-alt-5,59-(2,29-bithiophene)} (PNDI2OD-TT), N,N-di(2-ethylhexyl)-3,4,9,10-perylene diimide-1,7-diyl (PDTP-PDI), poly{N-[1-(2-ethylhexyl)-3-ethylheptanyl]-dithieno[3,2-b:20,30-d]pyrrole-3,6-dithien-2-yl-2,5-di(2-ethylhexyl)-pyrrolo[3,4-c]pyrrole-1,4-dione-50,500-diyl (PDTP-DTPDI), poly[4-(4,4-dihexadecyl-4H-cyclopenta[1,2-b:5,4-b']dithiophen-2-yl)-alt-[1,2,5] thiadiazolo-[3,4-c]pyridine] (PCDTPT), and analogues with the same donor or acceptor unit.

Organic Semiconductor Small Molecules

The organic semiconductor small molecule can include, but is not limited to, 2,7-dioctyl [1]benzothieno[3,2-b]benzothiophene (C8-BTBT) and analogues with the same BTBT conjugated core, 2,9-didecyl-dinaphtho[2,3-b:2',3'-f] thieno[3,2-b]thiophene (C8 or C10-DNTT) and analogues with the same DNTT conjugated core, 6,13-bis(triisopropylsilylethynyl)pentacene (TIPS-pentacene) and derivatives, perplene diimide derivatives (PDIs) and derivatives, naphthalene diimides (NDIs) and derivatives, phenyl-C61-butyric acid methyl ester, phenyl-$C_{71}$-butyric-acid-methyl ester and derivatives, buckminsterfullerene (C60), pentacene and derivatives, rubrene and derivatives.

Support Substrate

In one embodiment of the invention, the nanoporous semiconductor thin film or sensor is supported by a support substrate. The support substrate can comprise one or more of an acrylamide, cellulose, nitrocellulose, glass, indium tin oxide, silicon wafer, mica, polystyrene, or polyvinylidene fluoride (PVDF) filter, filter paper (e.g., Whatman), glass fiber filters (GF), fiberglass, polyethylimine coated GFs, porous mylar or other transparent porous films, cellulose nitrate (CN) membrane, mixed cellulose ester membrane, cellulose acetate membrane, polyethersulfone (PES) membrane, PTFE membrane, ultrafiltration membranes of poly (vinyl chloride) (PVC), carboxylated poly(vinyl chloride) (CPVC), polystyrene, polyethylene vinyl acetate, polypropylene, polymethacrylate, polyethylene, polyethylene oxide, polyimide, poly(etherimide), polyarylate, polynorbornene, polycyclic olefin, polyethylene naphthalate, polyethylene terephthalate, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. The support substrate can be formed into pre-perforated strips, individual strips, individual sheets, or any other suitable shape. In one embodiment, the support substrate is flexible and wearable.

Electrode

An electrode is a composition that, when connected to an electronic device, can sense a current or charge and convert it to a signal. Alternatively, an electrode can be a composition that can apply a potential to and/or pass electrons to or from connected devices.

Electrodes include, but are not limited to, certain metals and their oxides, including gold; copper; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste).

The electrode can be a planar electrode. The electrode can be deposited on a sensor or the nanoporous semiconductor thin film by a variety of methods including, but not limited to, screen-printing or evaporation. An electrode may be open or covered by a cover to form a defined volume cell.

A sensor electrode can detect a change in resistance/current caused by the interaction of a ligand and an analyte such as C8-BTBT or DPP-TT. The change in resistance/current can indicate an amount of analyte present in the sample.

In some embodiments, an electrode is not used for detection of analyte/ligand binding or interaction. Instead other methods can be used to detect binding. In these embodiments, an electrode can be absent from the biosensor structure. For example, the increased amount of mass on the sensor when a ligand binds or interacts with an analyte in a sample can be detected. Additionally, a colorimetric or fluorescent change that occurs when a ligand binds an analyte can be detected. A change in a Raman spectroscopy or Fourier transform infrared spectroscopy reading can also be used to detect analyte/ligand binding or association. In other embodiments, electrochemical changes can be detected, fluorometric changes can be detected with HPLC, and immunoassay changes can be detected by HPLC. Gas chromatographic detection with mass spectrometry (GCMS) can also be used to detect ligand/analyte binding.

Devices

The invention also provides a device comprising a sensor and a detector. The detector can be connected to a data acquisition system. The detector can comprise a digital or analog multimeter that can measure voltage, current, and resistance. A detector can also be a spectrophotometer, fluorometer, or a spectrometer like a Raman spectrometer or a Fourier transform infrared spectrometer.

The data acquisition system can be selected from the group consisting of a computer, a hand-held device, a cell phone, and a tablet. The detector provides information (e.g., a sample identifier, a subject identifier, a quantity detected of one or more analytes, a positive or negative reading regarding the presence or absence of an analyte, or a combination thereof) to the data acquisition system, which can then analyze the information and provide an easy to read and interpret result. A device can further comprise a screen that allows for visualization of an amount of an analyte, such as ascorbic acid, present in a sample. A device can be battery operated and portable.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Templating Nanoporous OSC Thin Films

We demonstrate a simple, additive approach to fabricate nanoporous semiconductor thin films in solution processing. The solution processing methods we used include spin coating and meniscus-guided unidirectional coating; the latter shares the same fundamental physics as large-scale roll-to-roll printing (FIG. 1a). The simplicity and generality of this approach for fabricating nanoporous thin films stand in contrast to the conventional subtractive approaches based on lithography and etching, which involve complex procedures and corrosive chemicals.

Figure 6:
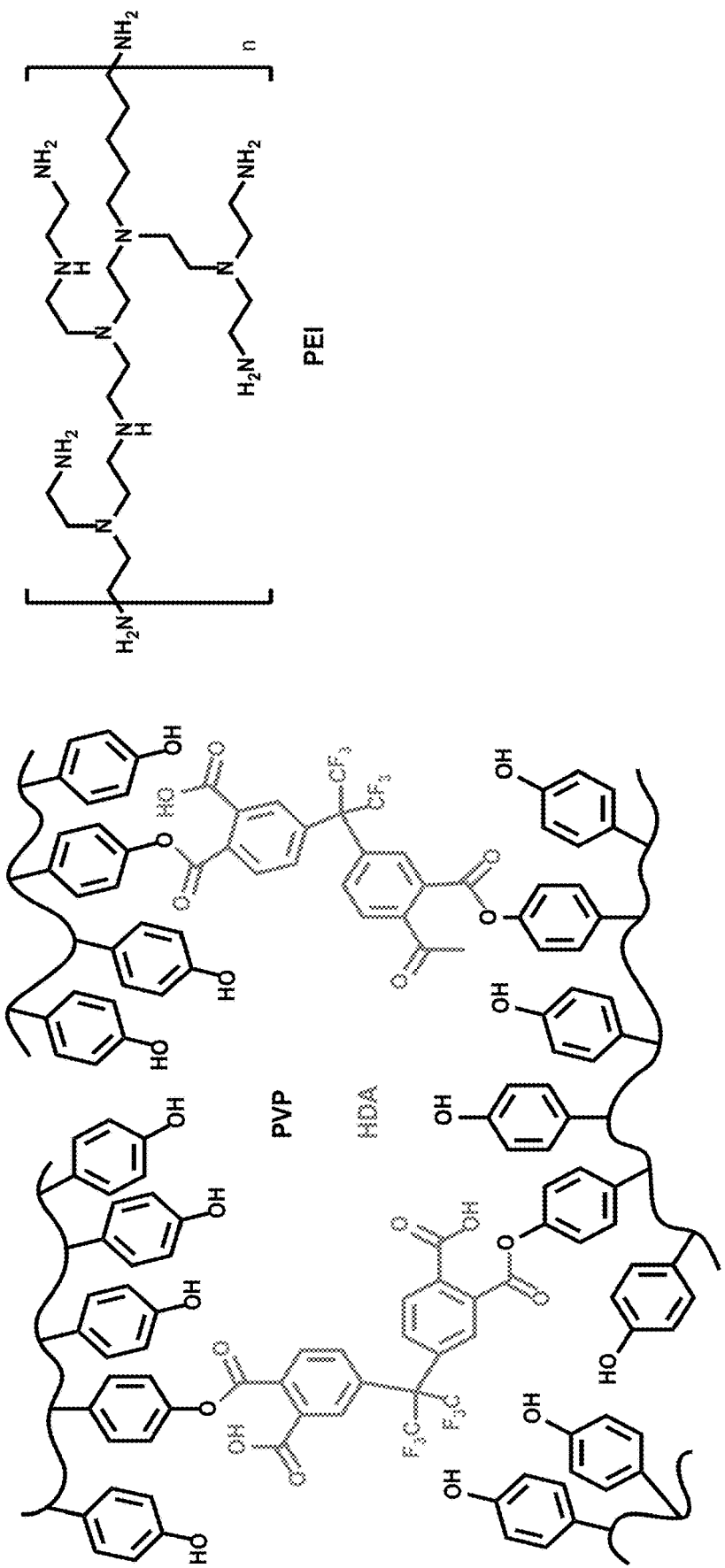
FIG. 6. Molecular structures. Chemical structure of cross-linked poly(4-vinylphenol) (PVP)-4,4'-(Hexafluoroisopropylidene)diphthalic anhydride (HDA) and polyethyleneimine (PEI).
Figure 7:
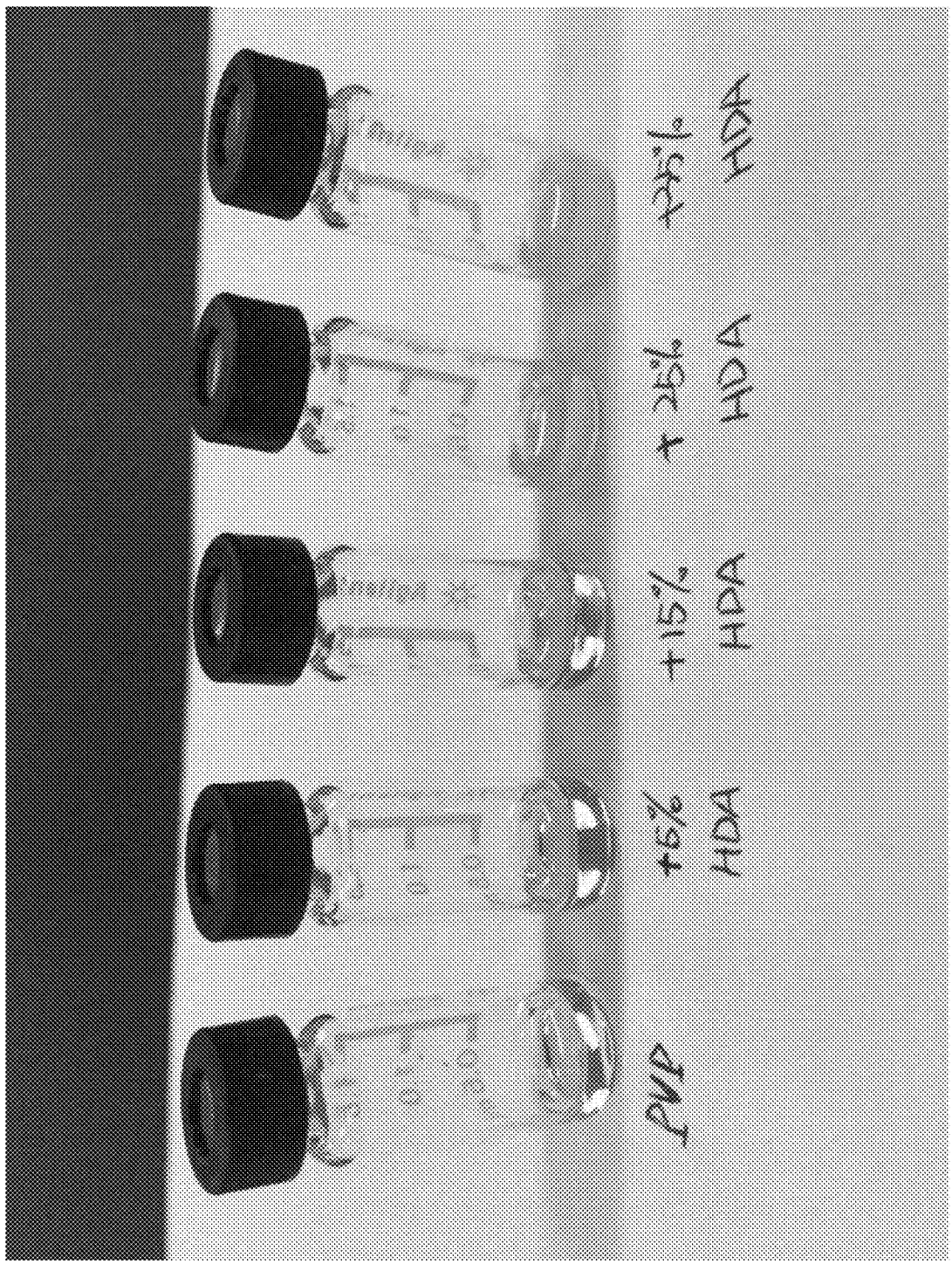
FIG. 7. Photograph of PVP-THF solution without and without adding HDA for testing the effect of HDA on the miscibility of PVP in THF.
Figures 8A, 8B:
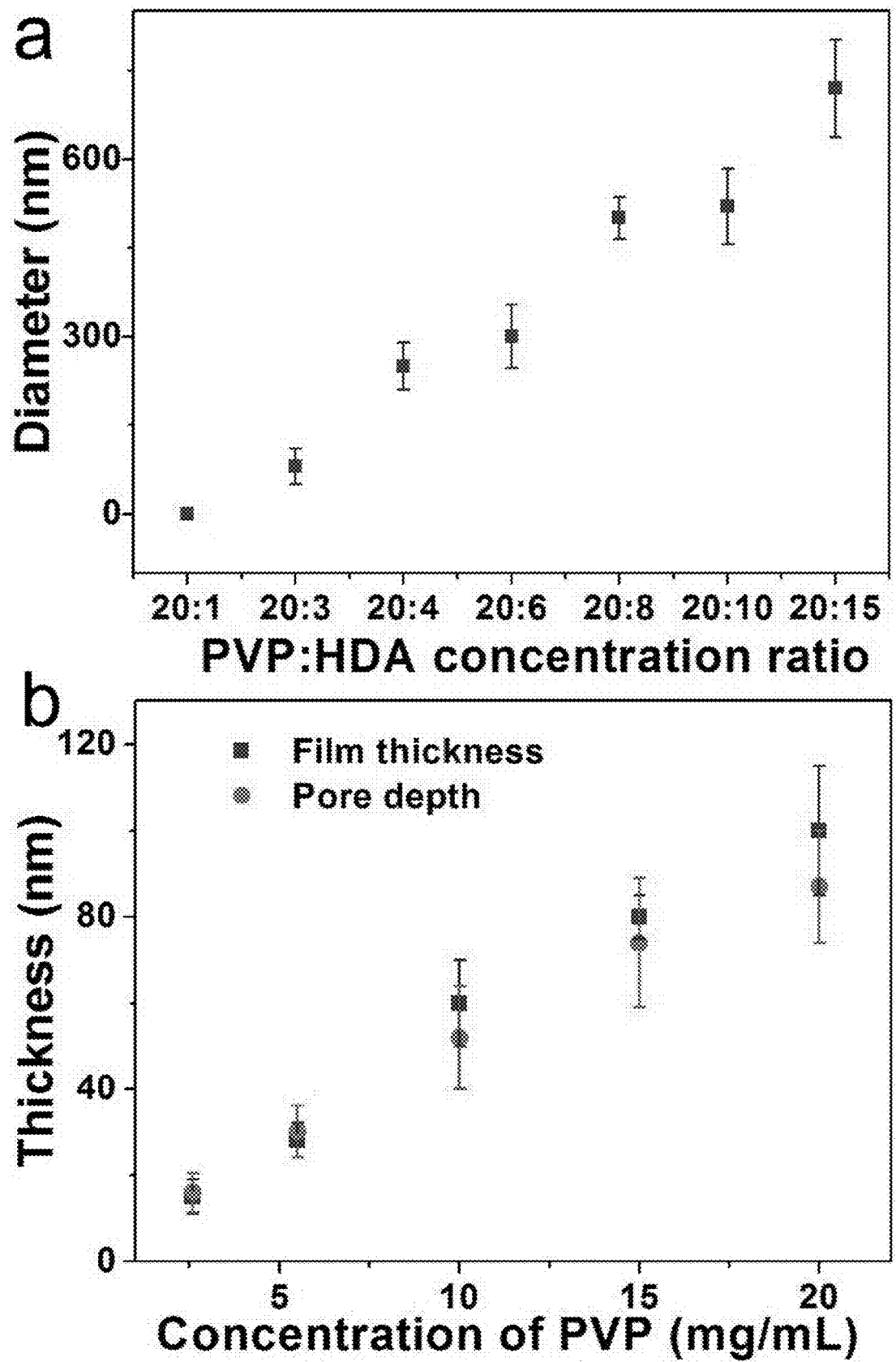
FIG. 8A-8B. Structure characteristics of the nanoporous PVP:HDA modified template. (a) PVP:HDA weight ratio dependent pore diameter, with the PVP concentration of 5.5 mg/mL. These data were obtained from AFM height images, some of which shown in FIG. 1. (b) Thickness and pore depth as a function of PVP concentration. The PVP:HDA weight ratio is 20:4. The error bars represent the standard deviation from at least five independent measurements.
Figures 9A, 9B, 9C, 9D, 9E, 9F:
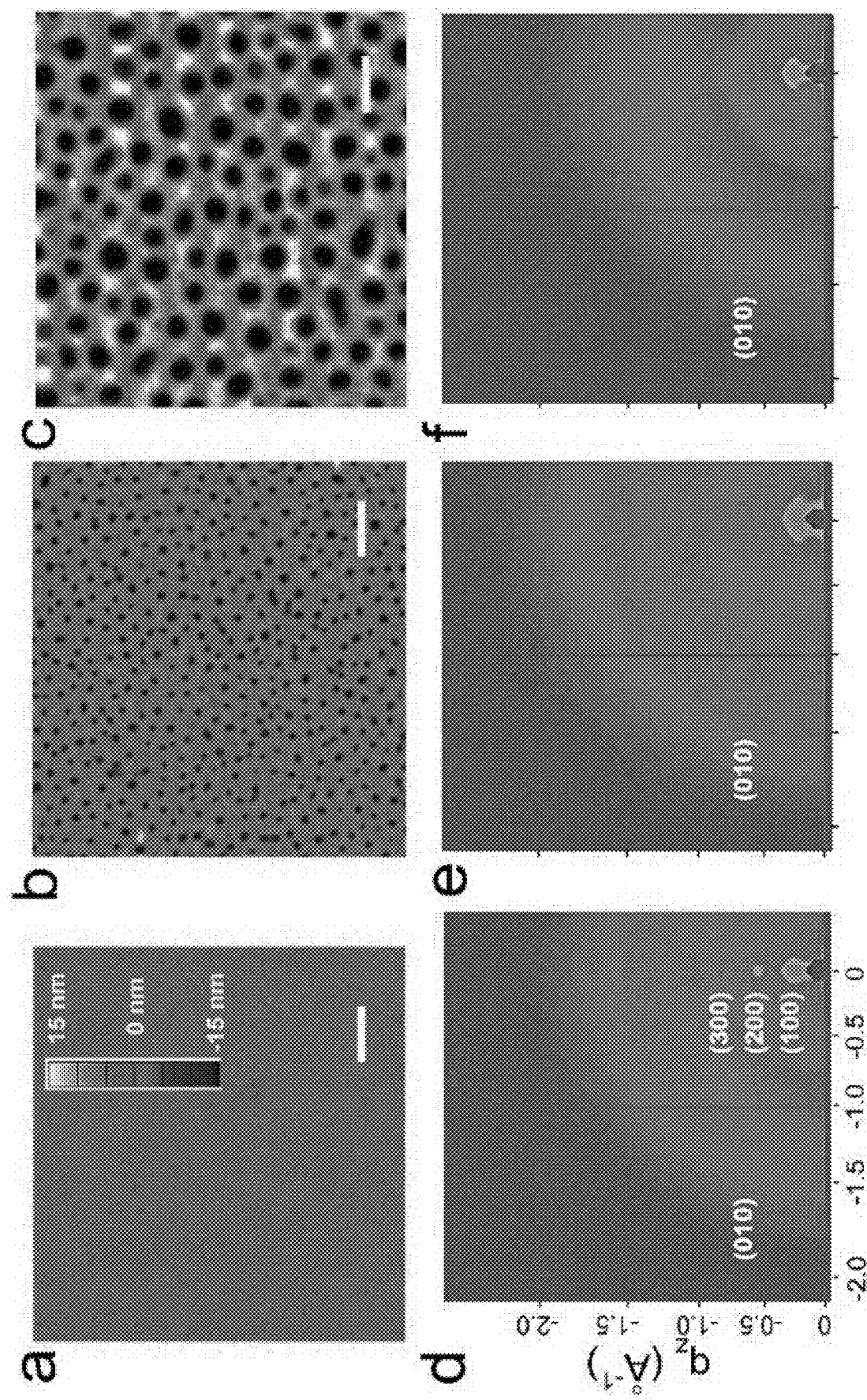
FIG. 9A-9G. Characterization of spin-coated DPP-TT film. (a-c) AFM images and (d-f) GIXD images of spin-coated DPP-TT films on PVP:HDA with (a, d) 0 nm, (b, e) 100 nm and (c, f) 400 nm pores. The scale bars are 1 μm in all images. (g) Comparison of geometrically corrected orientation distribution for spin-coated DPP-TT film with various pore structures. The error bars were standard errors of calculated (010) peaks areas from multipeak fitting.
Figure 9G:
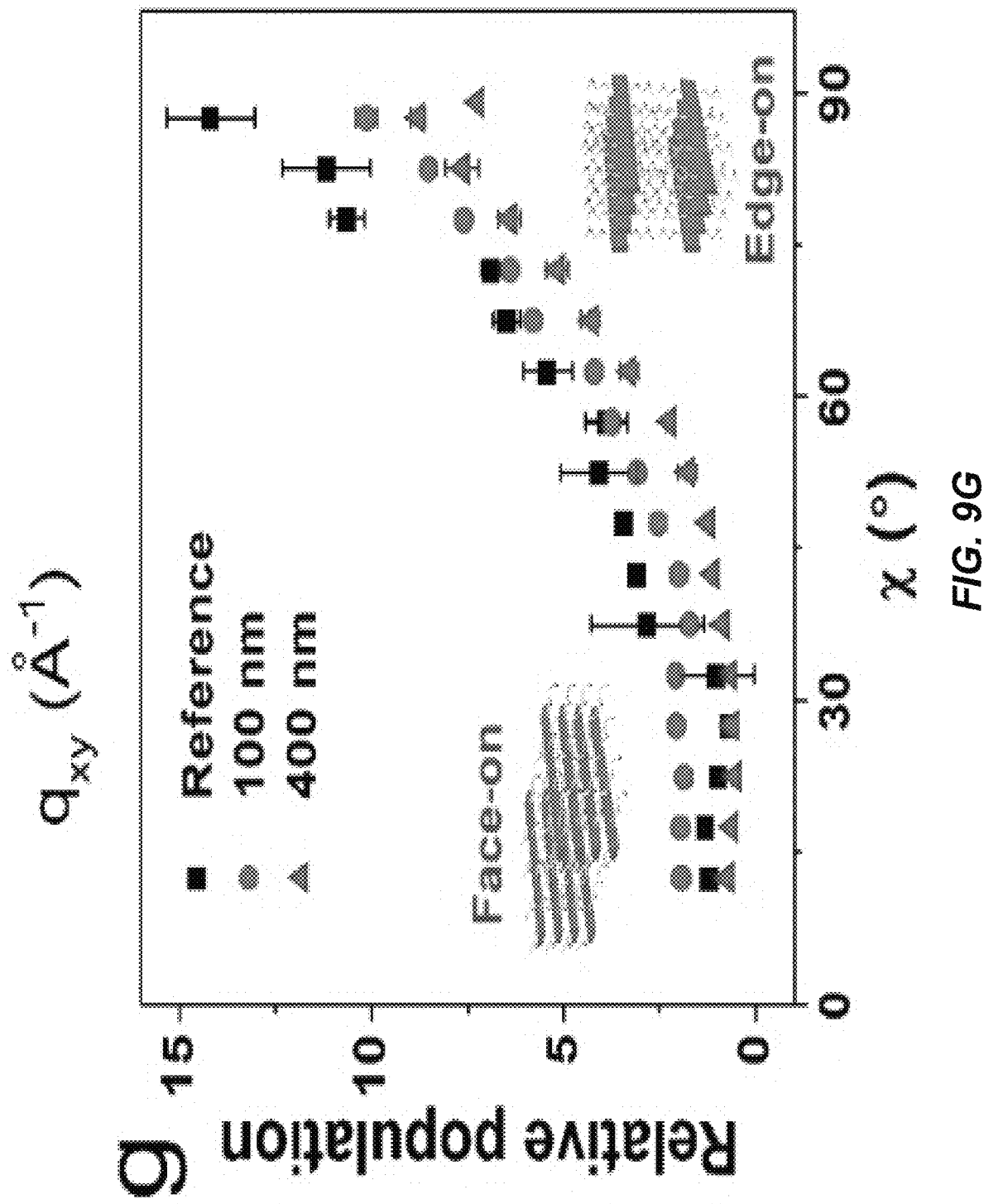
Figures 10A, 10B, 10C:
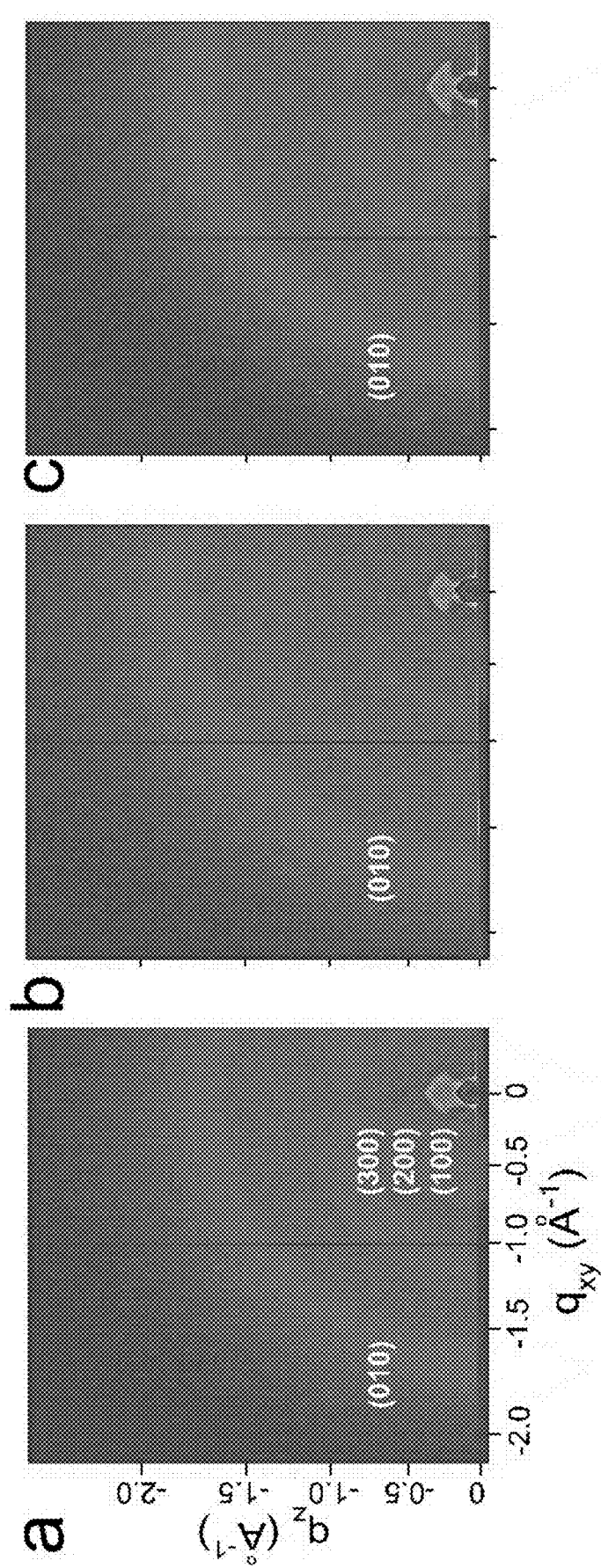
FIG. 10A-10C. GIXD investigations of printed DPP-TT film. DPP-TT films on PVP:HDA with (a) 0 nm, (b) 100 nm and (c) 400 nm pores. The diffraction patterns were obtained with the printing direction perpendicular to the incident beam, complementing FIG. 2d-f wherein the diffraction pattern corresponds to parallel scans.

The key to our method is to direct the semiconductor deposition using a nanoporous insulating layer serving as the template, which can be fabricated over a large area via one-step microphase separation during spin coating. The nanoporous template was prepared from poly(4-vinylphenol) (PVP)/tetrahydrofuran (THF) solution with 4,4'-(Hexafluoroisopropylidene) diphthalic anhydride (HDA) added as the cross-linking agent for PVP (FIG. 6). Nanopores ranging from 50 nm up to 1 µm in pore diameters were obtained by systematically increasing the HDA:PVP ratio in the solution (FIG. 1b-e and FIG. 8a). Through Hansen et al (*Prog. Org. Coat.*, 2004, 51, 109-112) solubility parameter calculations (Table 2, Scheme 1), we infer that addition of HDA decreases the miscibility of PVP with THF, which was proofed by the solubility measurement as FIG. 7, thereby inducing microphase separation between a continuous PVP-rich phase and a discrete THF-rich phase by the mechanism of nucleation and growth. Subsequent THF evaporation leaves nanopores in the film. Adding more HDA in PVP-THF solution contributes to increased pore size (FIG. 8a). AFM characterizations revealed that the nanopores extend through the entire thickness of the PVP:HDA film (FIG. 8b).

TABLE 2

Hansen solubility parameters for various materials and calculated molecular distance (Scheme 1).

| | Hansen solubility parameter | | |
|---|---|---|---|
| Materials | Dispersion ($\delta_D$) | Polarity ($\delta_P$) | H-bond ($\delta_H$) |
| PVP | 20.33 | 29.26 | 14.47 |
| HDA | 20.52 | 13.82 | 6.32 |
| PVP-HDA (stoichiometry ratio = 2.6:1) | 20.77 | 0.92 | 14.41 |
| THF | 16.75 | 5.69 | 7.98 |

Scheme 1.
The distance (R value) between different molecules is calculated by the Hansen equation.

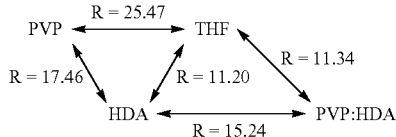

where the Hansen Equation is:

$$R^2 = 4(\delta_{D1}-\delta_{D2})^2 + (\delta_{P1}-\delta_{P2})^2 + (\delta_{H1}-\delta_{H2})^2, \text{ and}$$

where the unit for the solubility parameter is $MPa^{1/2}$ (MPa is the abbreviation for mega pascal).

Figure 11:
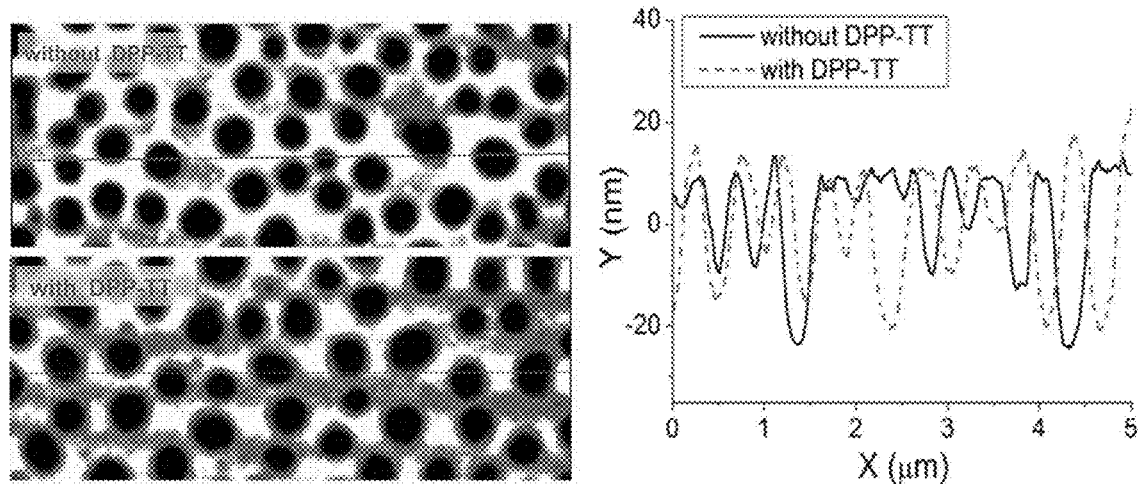
FIG. 11. Comparison of pore structures before and after the deposition of DPP-TT. The concentration of PVP is 5.5 mg/mL for template layer fabrication, while DPP-TT was deposited on the template layer from chlorobenzene solution (5 mg/mL) via spin coating. The corresponding thickness of the DPP-TT layer was measured to be 23 nm on average. The figures compare the AFM height images before and after DPP-TT deposition. Depth profile is shown along the horizontal line.

With the nanoporous PVP:HDA template prepared, we next deposited organic semiconductor thin film on the template layer using either spin-coating or meniscus-guided coating (FIG. 1a). We first deposited poly(diketopyrrolopyrrole-thiophene-thieno[3,2,b]thiophene-thiophene) (DPP-TT), a high performance donor-acceptor conjugated polymer. Before deposition, we grafted a monolayer of octadecyl tricholorosilane (OTS) on the template layer to passivate the charge traps. After DPP-TT deposition, we observed a faithful pattern transfer from the template layer (FIG. 1b-e) to the semiconductor layer (FIG. 2a-c and FIG. 9a-c) using both solution processing methods. The DPP-TT polymer formed a continuous thin film with isolated nanopores decorating the entire surface. The continuity of the thin film is important for providing percolation pathways for the charge carriers in a transistor device. From AFM height images, we measured that the pore diameter and pore depth in the semiconductor layer remain almost the same as those in the template layer, across the entire range of pore sizes tested (FIG. 11). From unchanged pore depth, we infer that the template pore floors are coated with DPP-TT of the same thickness as that on the top surface. The almost identical pore diameter before and after DPP-TT deposition indicates that the pore walls are not coated by the polymer film, particularly considering that the DPP-TT film thickness is by no means negligible (~23 nm). We later show that this morphology feature is important for enhancing chemical sensitivity by exposing the conductive channel of the transistor device.

Example 2. Characterization of Nanoporous Semiconductor Films

Figures 2A, 2B, 2C, 2D, 2E, 2F:
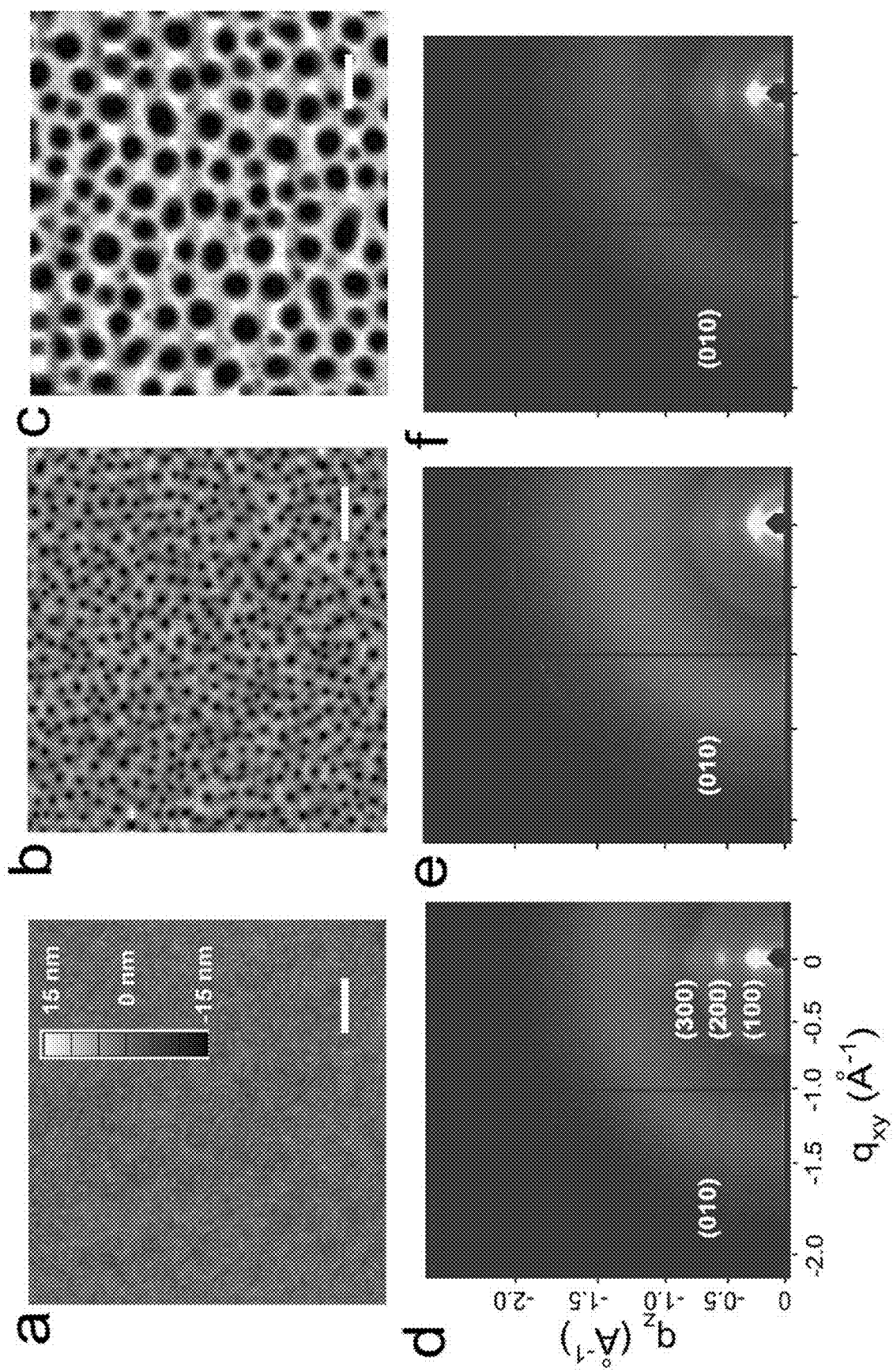
FIG. 2A-2H. Morphology Characteristics of printed DPP-TT thin films. (a-c) AFM images and (d-f) GIXD diffraction patterns of printed DPP-TT film on the PVP:HDA template layer with pore size of (a, d) 0 nm, (b, e) 100 nm and (c, f) 400 nm. The scale bars are 1 µm in all AFM images. Films were printed at 0.5 mm/s from 3 mg/mL chloroform solution at room temperature. Arrows indicate the printing direction. GIXD was taken with the printing direction is parallel to the incident beam as well as perpendicular to the incident beam. The GIXD images are not geometrically corrected to show the lamella peaks clearly. (g) Comparison of geometrically corrected orientation distribution for printed DPP-TT film with various pore sizes. The plot at polar angle $\chi=0°$ indicates face-on orientation and $\chi=90°$ represents edge-on orientation. The normalized diffraction intensities scale with the population of the crystallites with orientation characterized by the polar angle $\chi$. The error bars were standard errors of calculated (010) peaks areas from multipeak fitting. (h) Schematic illustrating the cross-sectional morphology of porous DPP-TT film printed on top the porous PVP:HDA template. The magnified image shows the edge-on molecular packing in the DPP-TT layer.
Figures 2G, 2H:
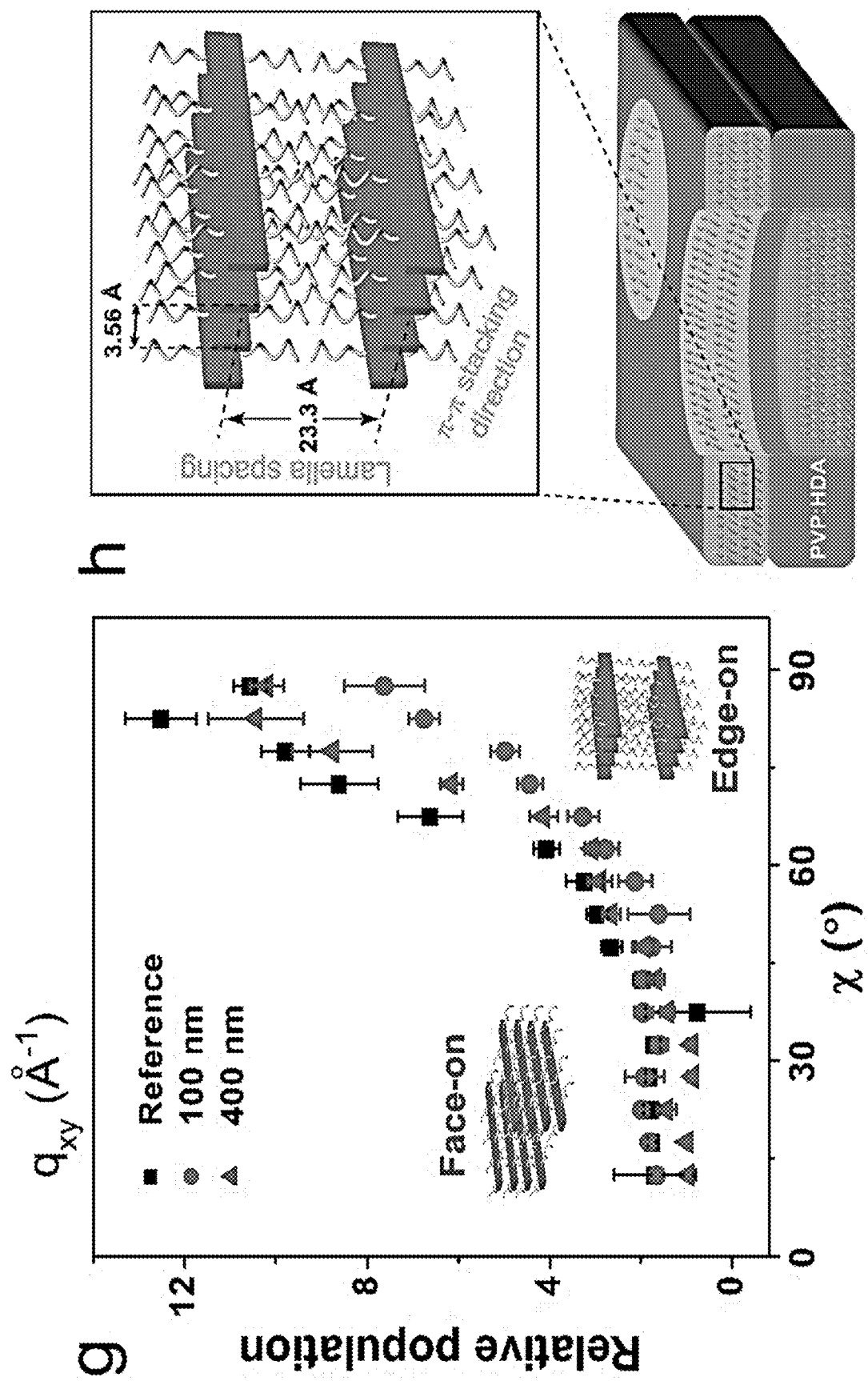

We further characterized the molecular packing in the nanoporous semiconductor films by Grazing-incidence X-ray diffraction (GIXD) (FIG. 2d-f, FIGS. 9 and 10). The detailed molecular packing analysis is summarized in Table 3 and Table 4. Not surprisingly, the presence of nanopores did not noticeably alter the molecular packing in the DPP-TT thin film. FIG. 2g shows the geometrically corrected orientation distribution of crystallites in coated DPP-TT films obtained from pole-figure analysis on the π-π stacking ring. The analysis unveiled a predominant edge-on orientation of the π stacks (FIG. 2h and FIG. 9g) in all cases tested regardless of the processing methods and the pore sizes. We expect this preferred orientation to promote the charge-transfer reaction with the analyte by maximizing the exposure of the π orbitals of the conjugated core at the pore wall.

Figures 12A, 12B:
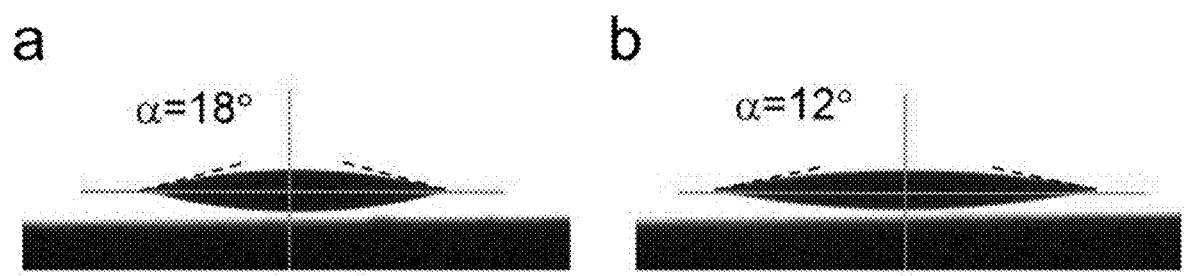
FIG. 12A-12B. Contact angle of DPP-TT/chlorobenzene drop on substrate which is (a) nonporous and (b) with pore diameter of ~400 nm and pore depth of ~30 nm. For the liquid droplet on a porous surface in the Wenzel state, the apparent contact angle is modified and relates to the intrinsic contact angle by the following equation.
Figure 13:
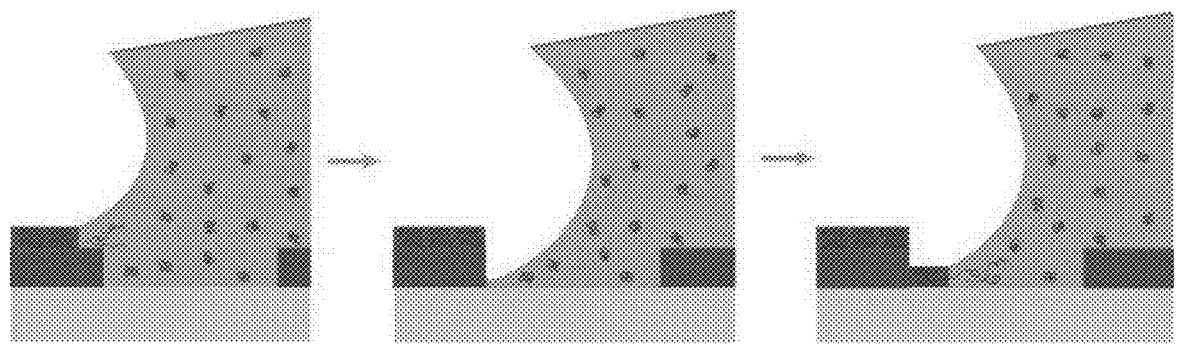
FIG. 13. Mechanism of OSC deposition on the porous template. Schematic illustrating the inferred molecule deposition process during the meniscus-guided coating.

How does the nanoporous template direct the semiconductor deposition process to yield the observed morphology. First, we determined that the polymer ink solution is in the Wenzel state when in contact with the nanoporous template (FIG. 12), indicating that the ink wets the entire contour of the template layer. Therefore, we expect the polymer deposition on the pore floor to occur in the same fashion as on the top surface, both driven by solvent evaporation at the triple-phase contact line. When the meniscus sweeps over the vertical pore wall, however, deposition does not have time to occur due to the constant meniscus speed along the coating direction. The consistently low contact angle between the ink and the entire porous template may have also prevented contact line pinning and therefore no deposition occurred at the pore wall (FIG. 13). The same mechanism applies to the deposition of 2,7-dioctyl [1]benzothieno[3,2-b]benzothiophene ($C_8$-BTBT), a small molecule semiconductor as shown later.

TABLE 4

Molecular packing in spin-coated DPP-TT films analyzed from GIXD images.

| Organic thin films | Without pores | 100 nm pores | 400 nm pores |
|---|---|---|---|
| Lamella spacing (Å) | 23.20 ± 0.05 | 23.35 ± 0.09 | 23.21 ± 0.06 |
| π-π stacking distance (Å) | 3.69 ± 0.07 | 3.68 ± 0.02 | 3.68 ± 0.02 |
| FWHM of π-π stacking peak (Å$^{-1}$) | 0.22 ± 0.06 | 0.27 ± 0.03 | 0.26 ± 0.02 |

Example 3. Nanoporous Polymer OFET for Ammonia Sensing

Figure 14:
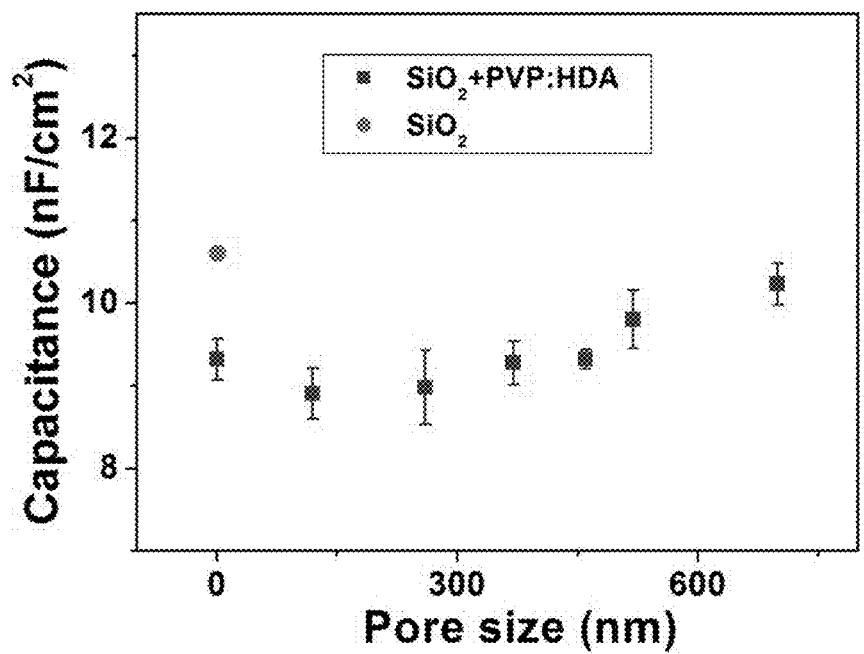
FIG. 14. Capacitance of template modified dielectric. The plots represent the capacitance of the 300 nm $SiO_2$ dielectric layer combined with the PVP:HDA template layer as a function of pore sizes. The thickness of the modified layer is kept at 30±8 nm.
Figures 15A, 15B:
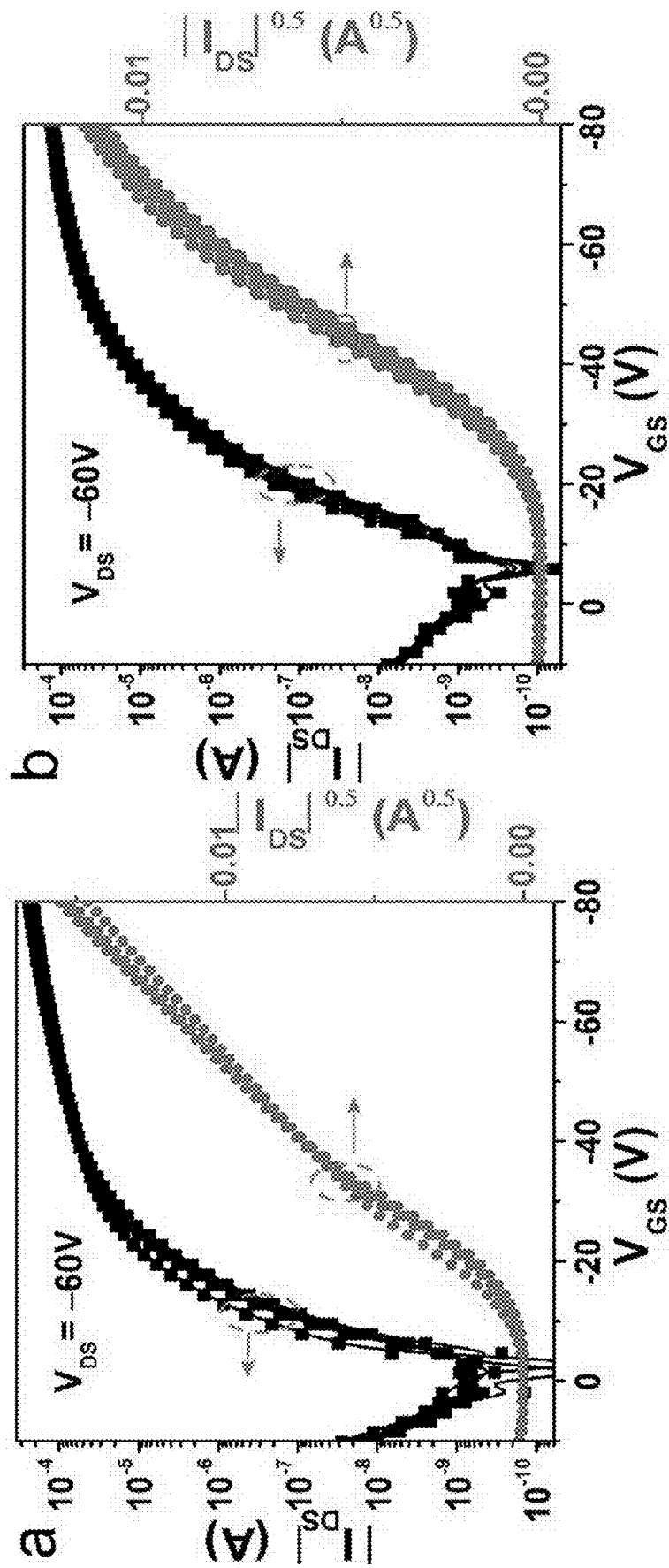
FIG. 15A-15B. Stability measurements (5 sweeps) under ambient conditions for DPP-TT OFETs (a) without and (b) with pores.

To characterize the charge transport properties and sensing performance of the nanoporous semiconductor thin films, we fabricated top contact bottom gate transistor devices and performed electrical measurements under ambient conditions (FIG. 3). Typical transfer curves of DPP-TT OFETs with and without pores are shown in FIG. 3a. Both devices exhibited predominant hole transport with an on/off ratio of ~$10^5$. The DPP-TT based nanoporous OFETs had comparable mobility (0.30±0.05 cm$^2$V$^{-1}$ s$^{-1}$) but slightly lower on-current compared to the nonporous devices, due to a slight decrease in capacitance when the nanostructured template layer was introduced (FIG. 14). This observation confirms that introducing nanopores did not adversely influence the device performance. Notably, the transistor devices remained stable after repeated measurements in air, which is ideal for sensing applications (FIG. 15).

Figures 3A, 3B:
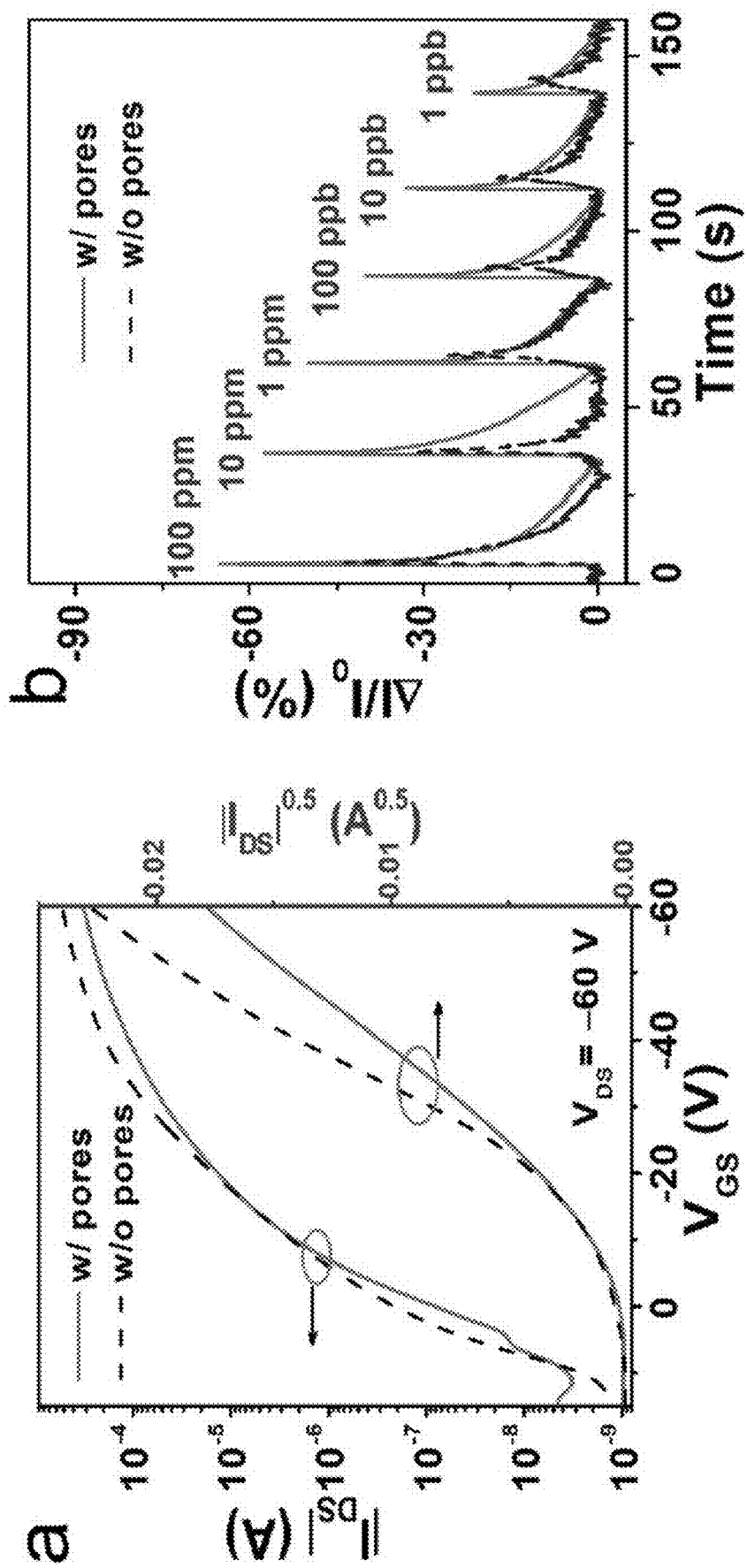
FIG. 3A-3F. Nanoporous OFET based ammonia sensor. (a) Comparison of transfer curves from porous vs. nonporous OFET. The devices were fabricated with a channel length of 65 µm and width of 4500 µm. (b) Current responses of DPP-TT based sensing device to a series of ammonia gas concentrations at constant voltage ($V_{GS}=-10V$, $V_{DS}=-20V$). The devices were fabricated with DPP-TT film without (w/o) or with (w/) pores (with a diameter of ~700 nm). (c) Read-out signals showing percentage current change as a function of time responding to 1 ppb $NH_3$. The continuous lines show the simulated response based on the reaction model. (d) Schematic diagram of the nanoporous OFET-based ammonia sensor. The magnified cartoon illustrates the charge transport reaction occurring at the conductive channel with ammonia. (e) Sensitivity of DPP-TT devices to ammonia with concentrations ranging from 1 ppb to 100 ppm. Dependence of sensitivity on pore sizes is shown. The sensitivity is defined as the percent change in current $\Delta I$ with respect to the initial current $I_0$. (f) Dependence of sensitivity on the area fraction of the exposed pore wall. $A_s$ is the total surface area of the pore wall calculated from the film thickness, pore diameter and pore area density. $A_t$ is the total surface area of the semiconductor layer. Error bars were calculated from 6-8 measurements on 3-4 independent samples at each condition.

We next measured the sensing performance of DPP-TT transistor to NH$_3$ in real time. To this end, the gas sensing experiments were performed in a PDMS microfluidic system that enclosed the transistor devices. When NH$_3$ molecules are carried into the PDMS channel, they diffuse into the conductive channel of the transistor device and donate electrons to DPP-TT via a charge transfer reaction, thereby reducing the hole concentration and resulting in a decrease in the current. The device sensitivity to the analyte is defined as $\Delta I/I_0 = (I_g - I_0)/I_0$, where $I_0$ and $I_g$ denote the initial drain current and the current after exposure to the analyte respectively, and $\Delta I$ is the net current change. FIG. 3b show the dynamic sensing performance of DPP-TT based sensor for detecting NH$_3$ ranging from 1 ppb to 100 ppm (in v/v) in dry air. At the low concentration limit of 1 ppb, the presence of

TABLE 3

Molecular packing in printed DPP-TT films analyzed from GIXD images. Two-dimensional diffraction patterns were integrated along the polar angle χ to obtain a one-dimensional plot of intensity vs q. The one-dimensional diffraction pattern was subsequently deconvoluted with background subtraction to accurately determine the peak positions and the corresponding peak widths represented by the full width at half maximum (FWHM).

| Organic thin films | Printing direction | Without pores | 100 nm pores | 400 nm pores |
|---|---|---|---|---|
| Lamella spacing (Å) | par | 23.35 ± 0.01 | 23.22 ± 0.02 | 23.07 ± 0.02 |
| | perp | 23.18 ± 0.02 | 23.38 ± 0.02 | 23.28 ± 0.02 |
| π-π Stacking distance (Å) | par | 3.57 ± 0.05 | 3.55 ± 0.05 | 3.56 ± 0.03 |
| | perp | 3.56 ± 0.04 | 3.58 ± 0.07 | 3.57 ± 0.04 |
| FWHM of π-π stacking peak (Å$^{-1}$) | par | 0.16 ± 0.01 | 0.14 ± 0.03 | 0.16 ± 0.02 |
| | perp | 0.15 ± 0.02 | 0.15 ± 0.01 | 0.15 ± 0.01 |

Figures 3C, 3D:
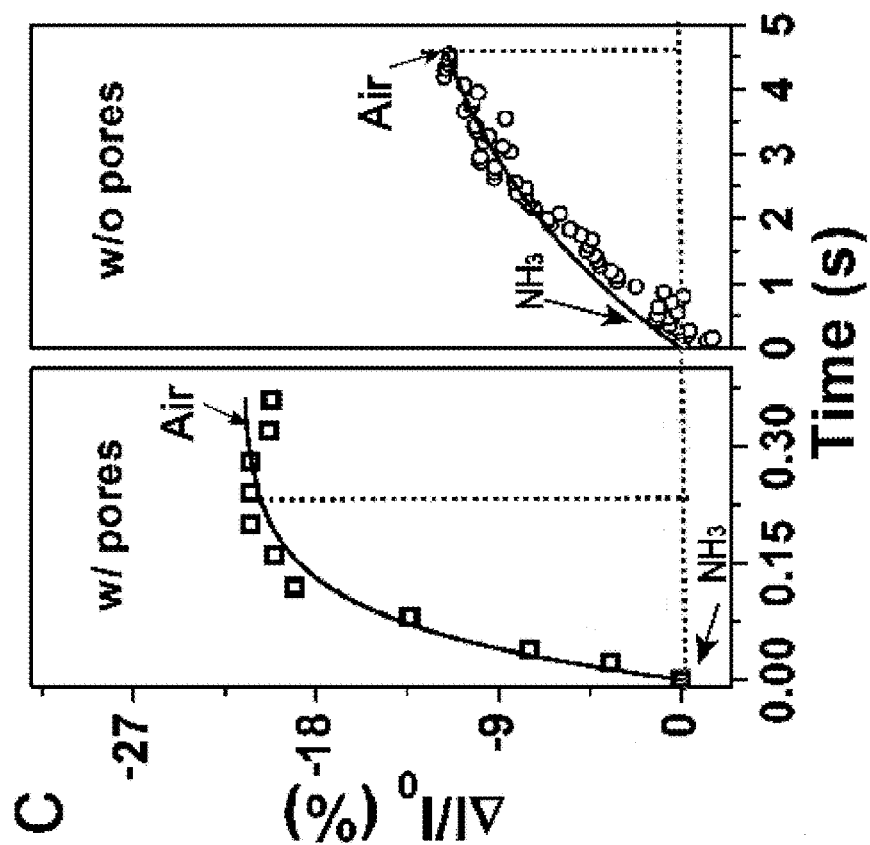
Figures 16A, 16B:
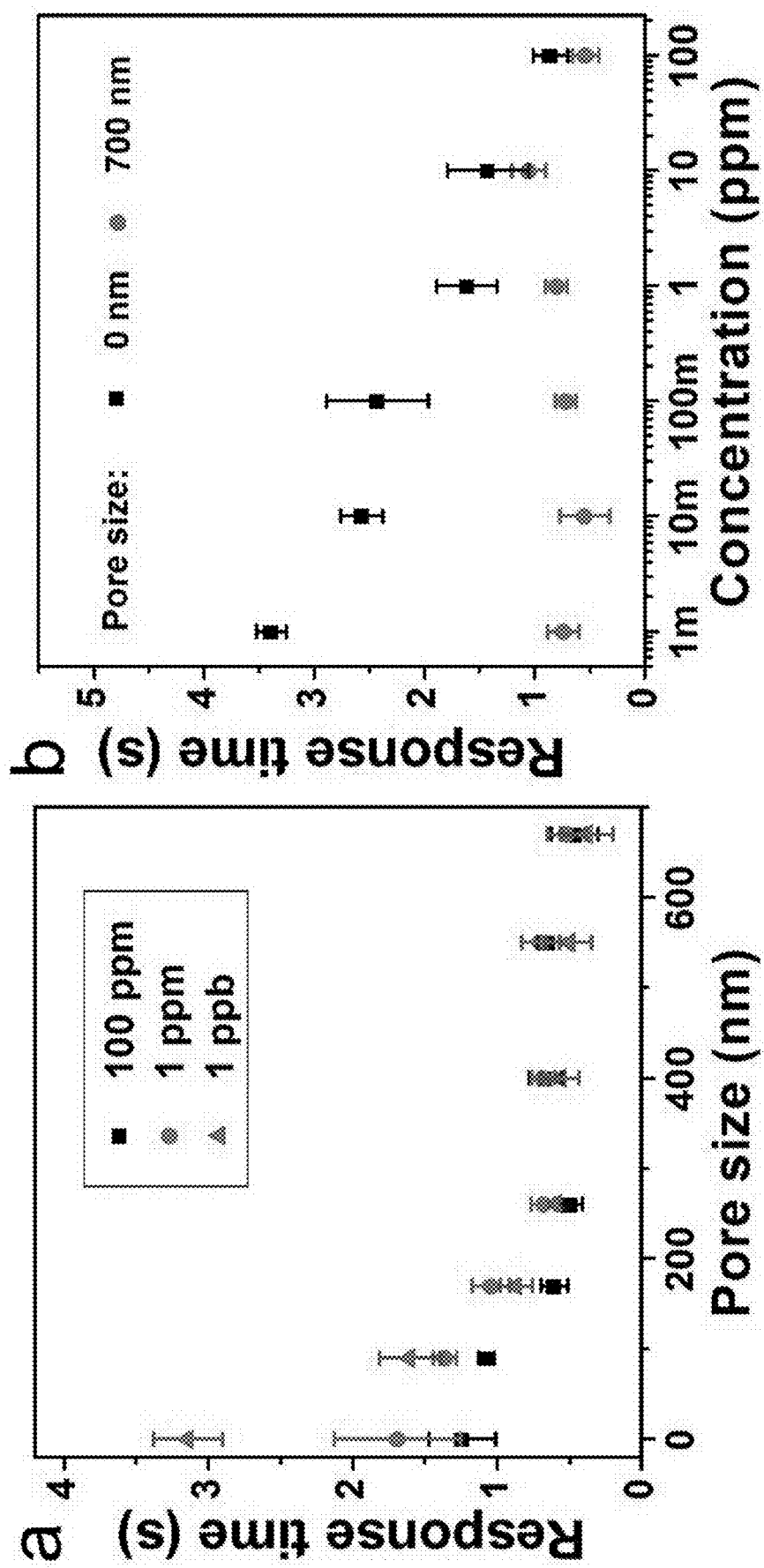
FIG. 16A-16B. Response time of DPP-TT sensors to $NH_3$ gas. (a) Response time as a function of pore size in DPP-TT sensors. (b) Response time of DPP-TT as a function of $NH_3$ concentration, comparing devices without pores and with 700 nm pores. Error bars were calculated from 6-8 measurements on 3-4 independent samples at each condition.

700 nm nanopores enhanced the sensitivity by up to 2.5 times to 27.8% and reduced the response time by an order of magnitude from seconds to hundred milli-second time scale (FIG. 3c and FIG. 16). Typical detection limits are frequently in the hundred ppb range with response time on the order of seconds to minutes (Table 5). Our low detection limit, high sensitivity and ultrafast response are unprecedented among OFET-based $NH_3$ sensors. The ultrasensitive and ultrafast sensing performance can enable even the most demanding health and environmental applications as demonstrated later.

TABLE 5

Recently reported sensing performance of OFET based $NH_3$ sensors.

| Organic thin films | Limit of detection | Sensitivity ($\Delta I/I_0$) | Response time | Fabrication of the active layer |
|---|---|---|---|---|
| Nanoporous DPP-TT | 1 ppb | 27.8% (1 ppb) 51% (100 ppb) | 0.4 s-1 s | Spin-coating/printing |
| pDPPCOOH-BT | 10 ppb | 12.5% (1 ppm) | >5 s | Spin-coating |
| HTEB ultrathin film | 100 ppb | 41% (100 ppb) 57% (500 ppb) | 5-32 s | Solution shearing |
| CuPc-TPFB CoPc-TPFB ultrathin film | 450 ppb | CuPc-TPFB 26% (450 ppb) CoPC-TPFB 28% (450 ppb) | 9-120 s/ >300 s | Thermal evaporation |
| Pentacene | 500 ppb | 23% (3 ppm) | ~100 s | Thermal evaporation |
| Graphene | 500 ppb | 10% (10 ppm) | >3600 s | Chemical vapor deposition |
| DPP-TT | — | 50% (10 ppm) | ~5 s | Bar-coating |

Example 4. Sensing Mechanism and Reaction Model

Figure 3E:
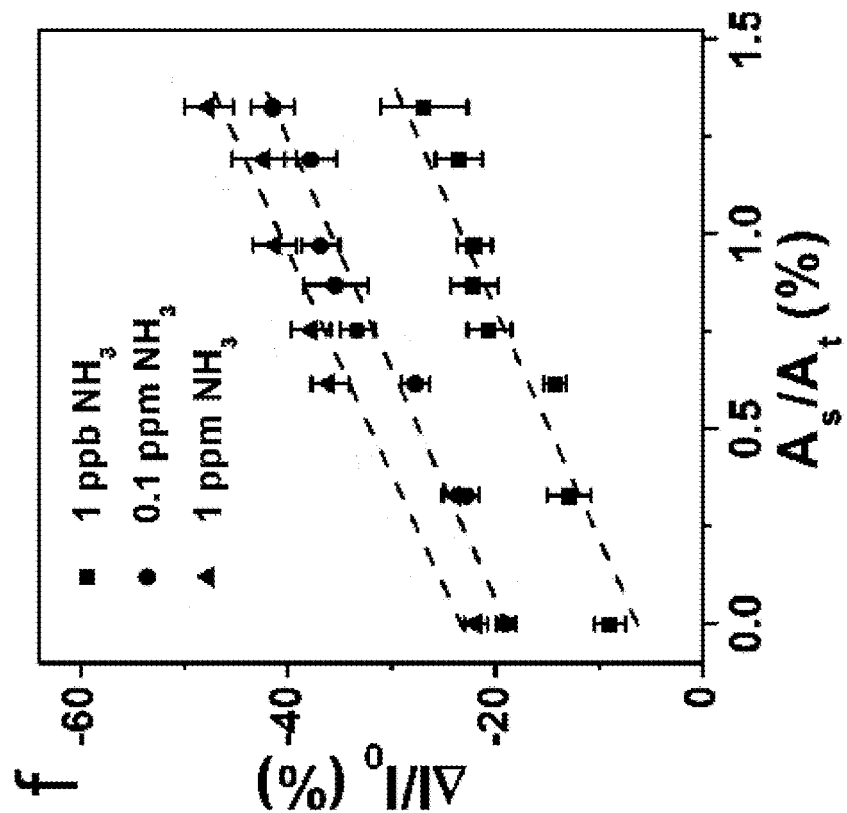
Figure 3F:
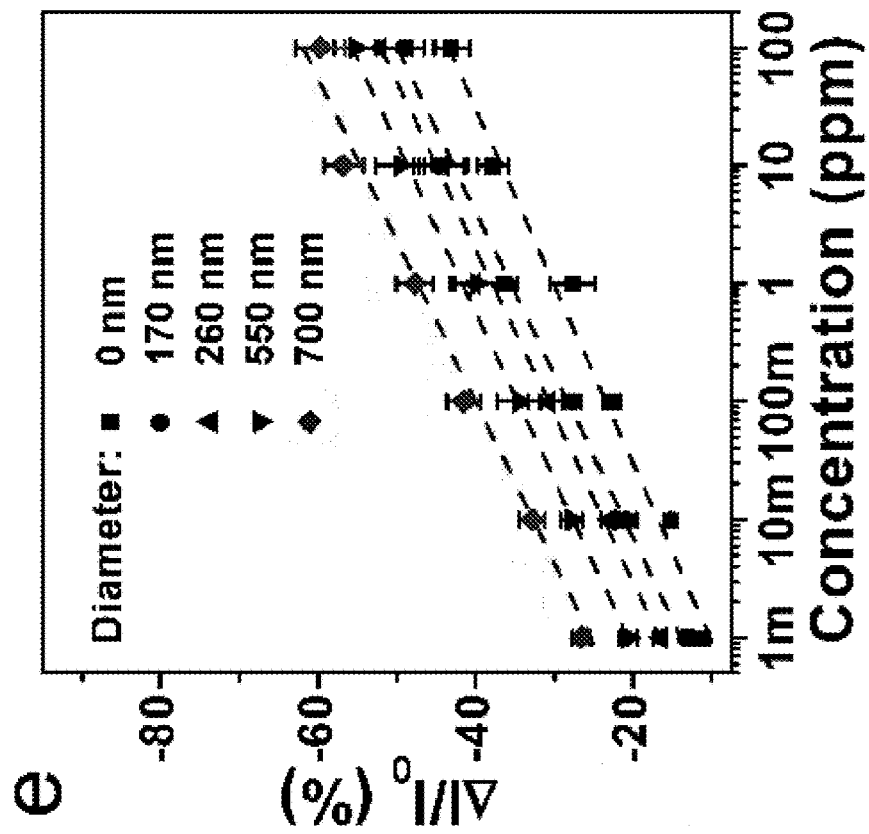

The mechanism by which nanopores promote device sensitivity and shorten response time was investigated. We hypothesized that introducing through-pores in the thin film exposes the highly reactive sites originally buried in the conducting channel to the pore wall (FIG. 3d). Their high reactivity comes from two aspects: first, the DPP-TT molecules in the conducting channel are positively charged serving as hole carriers; second, the backbone of DPP-TT is oriented edge-on with respect to the substrate (FIG. 2h), thereby favorably exposing the π-electrons to the pore wall. Both factors are expected to promote charge transfer reactions between $NH_3$ and DPP-TT at the pore wall. To test our hypothesis, we systematically varied the pore size and correspondingly the area fraction of the pore wall out of the total surface area ($A_s/A_t$), and measured the pore-size dependent sensing performance (FIG. 3e). We observed that the device sensitivity was linearly proportional to the pore wall area fraction $A_s/A_t$ (FIG. 3f). This observation is consistent with our hypothesis since the area density of highly reactive sites scales with the area fraction of the conductive channel exposed to the pore wall and therefore $A_s/A_t$. We further verified that the sensing performance was insensitive to the through-pore thickness when varied between 50 nm to 12 nm (FIG. 17), but further reducing the thickness to 8 nm started to decrease the sensitivity. This result suggests that the conducting channel likely has a thickness between 8-12 nm within which the highly reactive sites reside.

Figure 17:
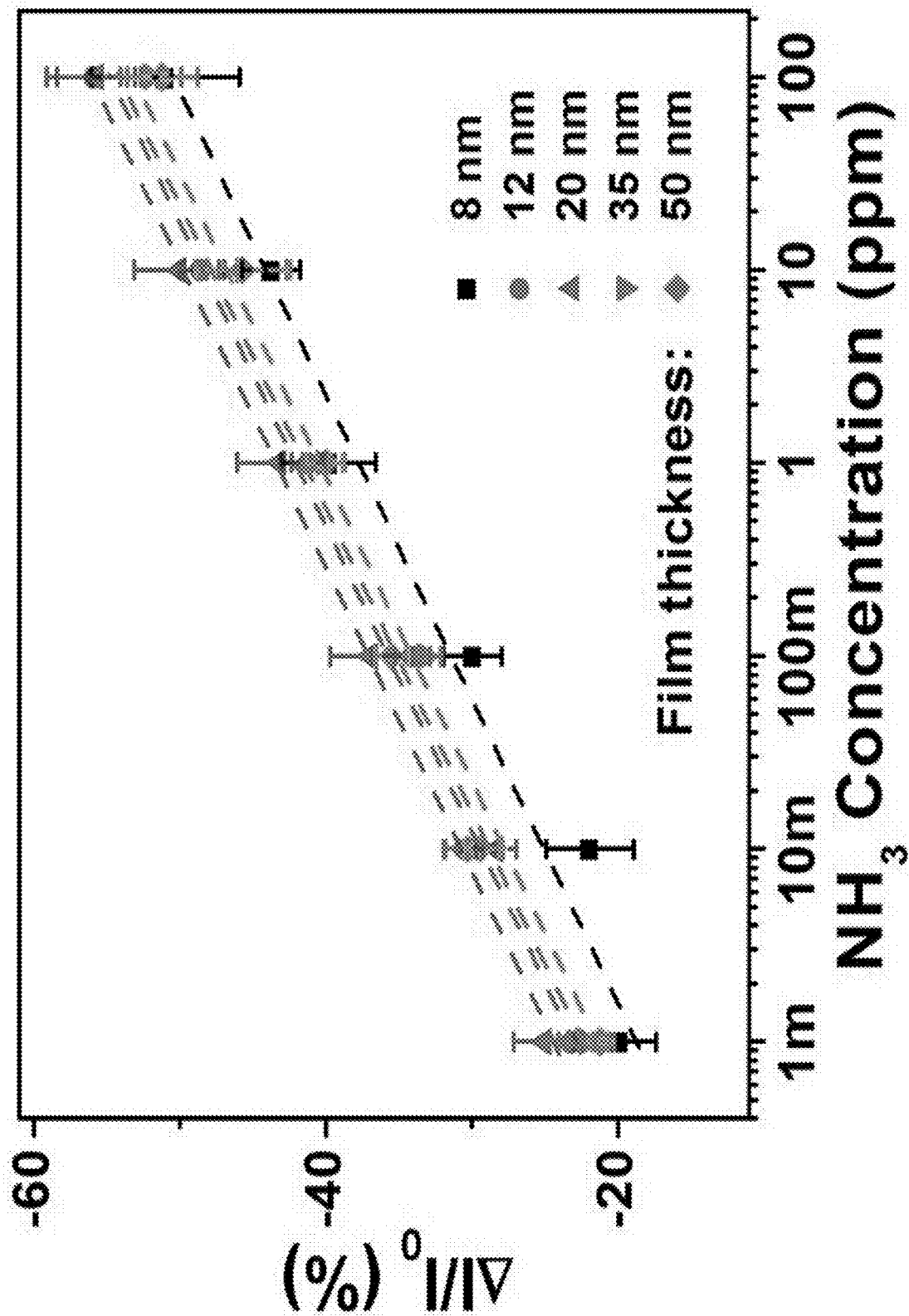
FIG. 17. Film thickness dependent sensing performance of DPP-TT sensors to $NH_3$ gas. Sensitivity of DPP-TT devices with various film thicknesses as a function of ammonia concentration. The devices were constructed with a pores diameter of 400 nm. The error bars were calculated from more than five devices.

To quantify the extent to which the charge transfer reaction rate is modulated by nanopores, we established a simple analytical model detailed below and FIG. 17. One important assumption of the model is negligible diffusional resistance in a low Damköhler number ($D_a$) regime. This assumption is justified since the estimated diffusion time scale is $10^{-4}$ s in nanoscopic thin films, which is at least three orders of magnitude shorter than the response time. Therefore, the response time is determined by the charge-transfer reaction alone. Considering a first-order charge-transfer reaction between the hole carrier ($DPPTT^+$) and the analyte ($NH_3$), as described by the following first-order reaction:

(Reaction 1)

we derived that device sensitivity follows the equation below:

$$\Delta I/I_0 = -\frac{1}{1+\frac{k_{-1}}{k_1 C_{NH_3}}}\left(1 - e^{(-(k_1 C_{NH_3} + k_{-1})t)}\right) \quad \text{(Equation 1)}$$

where $C_{NH_3}$ represents the concentration of $NH_3$, $k_1$ and $k_{-1}$ are the forward and backward reaction rate constant respectively, and t is the reaction time. It is evident that the sensing performance is highly dependent on the reaction rate constants.

Figures 18A, 18B, 18C, 18D:
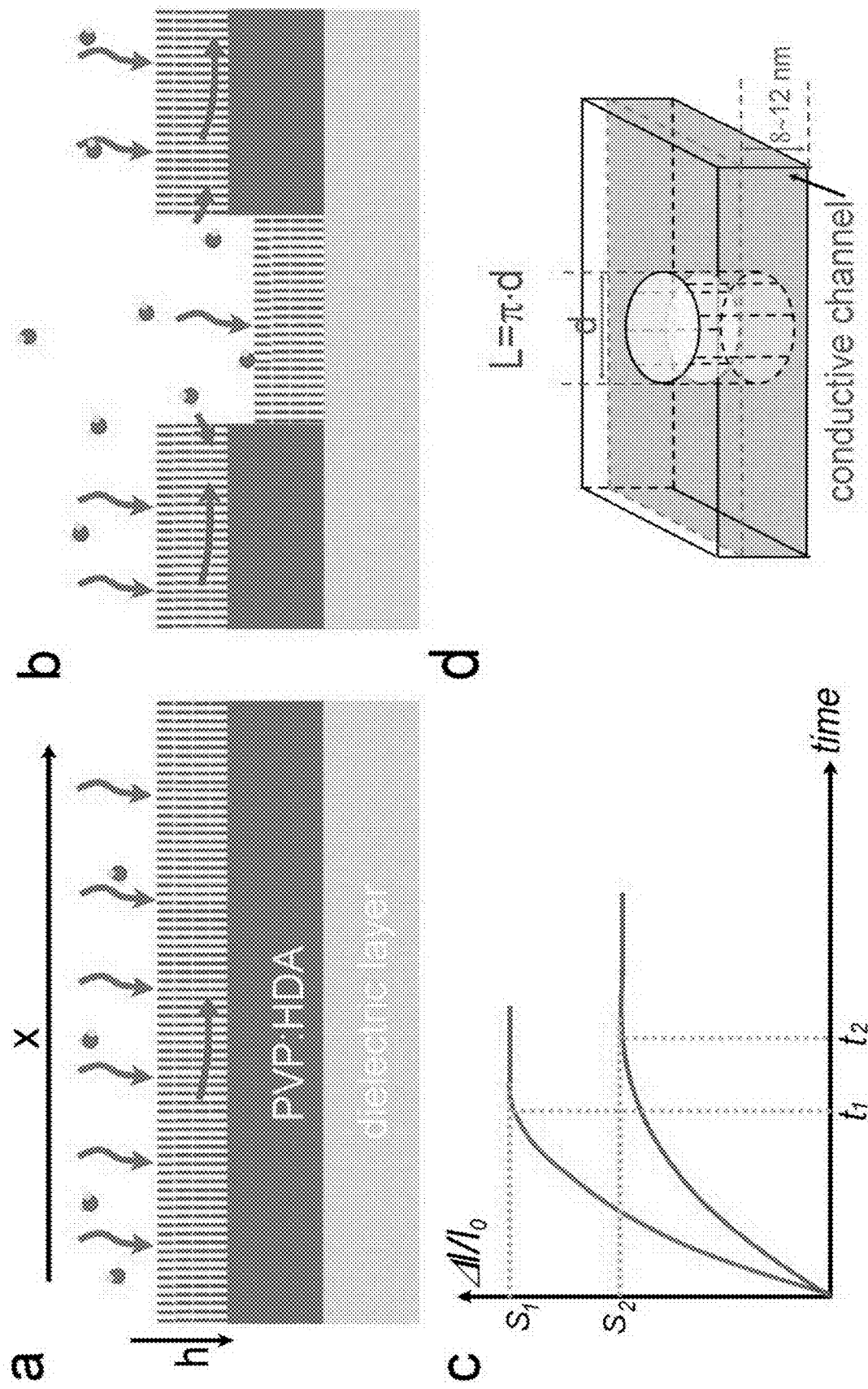
FIG. 18A-18D. Sensing mechanism of nanoporous DPP-TT OFET devices. Cross-section view comparing OFET devices (a) without and (b) with pores. (c) Dynamics responses comparing nonporous (lower line) and nanoporous (upper line) cases respectively. $S_1$ and $S_2$ are the sensitivities of nanoporous and nonporous OFET sensors, $t_1$ and $t_2$ represent the corresponding response time. (d) Schematic illustrating the reaction sites in the semiconductor layer.
Figure 19:
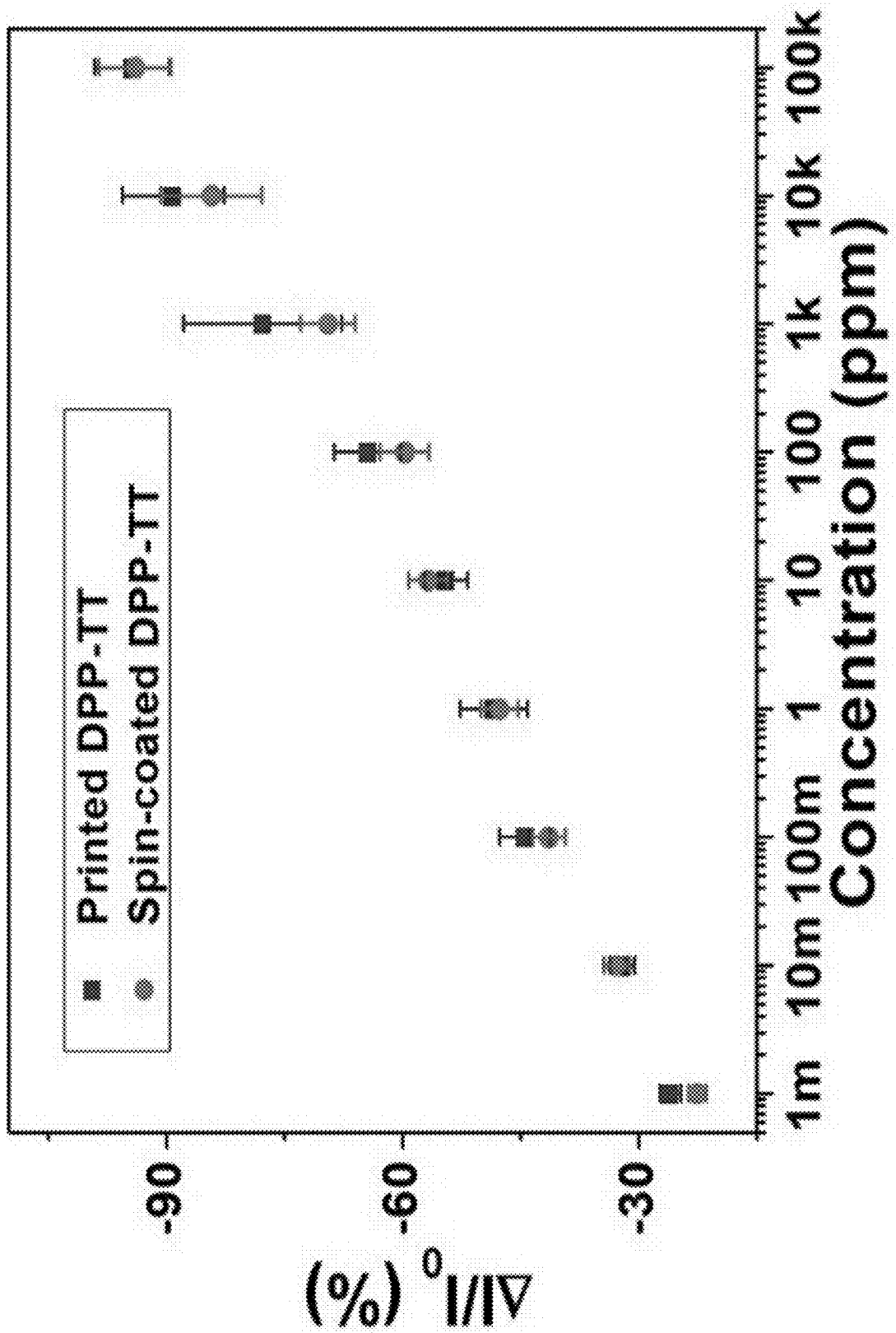
FIG. 19. Comparison of sensing performance of solution-processed DPP-TT sensors. The current response shown are DPP-TT based OFET devices in the presence of $NH_3$. The DPP-TT films were fabricated via the printing method (squares) and the spin-coating method (circles), respectively.
Figures 20A, 20B:
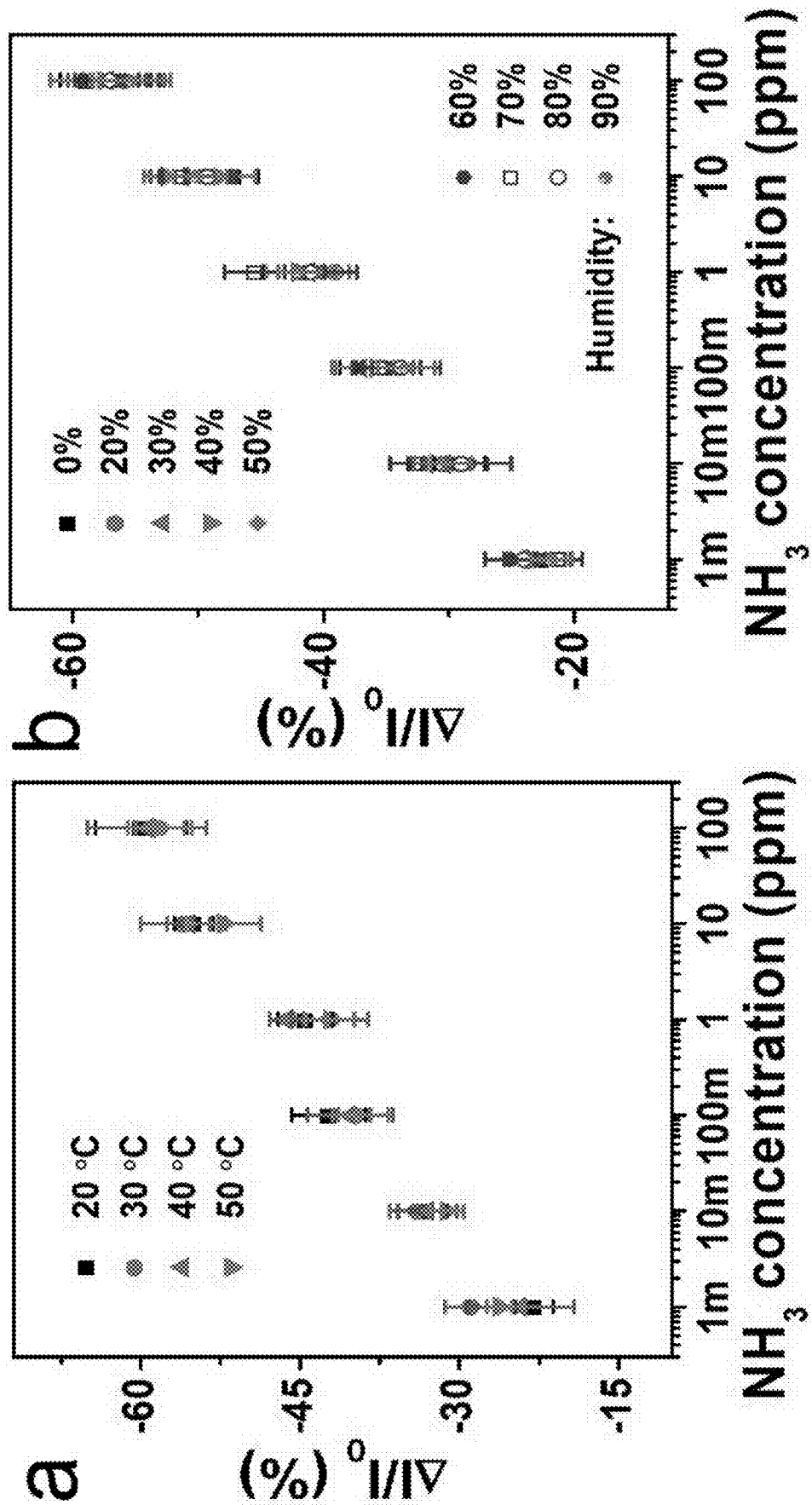
FIG. 20A-20B. Stability of porous DPP-TT based ammonia sensors. (a) Environment temperature and (b) Humidity dependence of the ammonia sensor of porous DPP-TT OFETs. The pore size for the organic thin film is 600 nm, and the error bars are achieved from 6 measurements on 2-3 independent samples at each condition.

To compare the reaction kinetics for sensors with and without nanopores, we fitted Equation 1 to the experimentally obtained dynamic monitoring curves and regressed the forward and backward reaction rate constants as a function of pore size and $A_s/A_t$ (FIG. 3f and Table 6). We found that $k_1$ was enhanced by an order of magnitude when the pore size increased from 0 to 720 nm and correspondingly $A_s/A_t$ increased from 0 to ~1.2%. On the other hand, $k_{-1}$ was not much affected, exhibiting a moderate two-fold increase. This result is consistent with our hypothesis that nanopores enhances the reactivity of the semiconductor layer by exposing highly reactive sites to the pore wall, resulting in ultrasensitive and ultrafast sensing performance of nanoporous devices. (FIG. 3d and FIG. 18). It is worth noting that recent studies on OFET gas sensors have reported improved sensitivity by decreasing the film thickness. The observed enhancement was frequently attributed to lowered analyte diffusion barrier. Our work indicates that enhanced reactivity is key to attaining high device sensitivity, not removing diffusion barriers in the case of thin film transistor based gas sensors. We also note that the devices fabricated via meniscus-guided coating and spin coating methods yielded almost the same sensing performance, showing the robustness of our nanoporous approach for attaining high sensing performance (FIG. 19). More importantly, the porous DPP-TT devices exhibit excellent environment stability, as demonstrated by the negligible current response to various concentration of $NH_3$ in a humidity regime of 0-90% and environment temperature at 20~50° C. (FIG. 20).

TABLE 6

Calculated reaction constants as a function of pore sizes obtained from fitting the dynamic monitoring curves with Equation 1.

| Pore diameter | 0 nm | 170 nm | 260 nm | 410 nm | 550 nm | 670 nm | 720 nm |
|---|---|---|---|---|---|---|---|
| $A_s/A_t$ (×10$^{-2}$) | 0 | 0.34 ± 0.1 | 0.52 ± 0.2 | 0.83 ± 0.1 | 1.09 ± 0.2 | 1.27 ± 0.1 | 1.19 ± 0.1 |
| $k_1$ (×10$^8$ s$^{-1}$) | 0.798 | 1.81 | 3.04 | 3.30 | 4.32 | 6.27 | 6.10 |
| $k_{-1}$ (s$^{-1}$) | 0.64 | 1.18 | 1.53 | 1.27 | 1.37 | 1.74 | 1.42 |

In OFET, the charge carriers accumulate and transport in the conducting channel at the semiconductor-dielectric interface. When the device is exposed to ammonia, a change in the charge carrier density takes place due to charge transfer reaction between ammonia and polymer resulting in a current change. Specifically, ammonia molecules act as electron donors to the p-channel, leading to a decrease of the source-drain current. Studies on the transduction mechanism of resistive gas sensors show that the sensing performance is determined by two processes: gas diffusion and surface reaction.

In thin film devices employed in this work, we estimated that the diffusion time scale is much smaller than the device response time scale. Considering ammonia diffusion in a solid film of 20-30 nm thick (h) and a diffusion coefficient (D) of $10^{-9}$ cm$^2$/s, the time scale for diffusion is on the order of $10^{-4}$ s estimated from equation t=h$^2$/D, which is at least three orders of magnitude shorter than the measured response time. Therefore, we infer that the sensing process is in the reaction-limited regime with the Damkohler number ($D_a$) much less than 1 ($D_a$=reaction rate/diffusion rate). This simplifies the reaction-diffusion problem into a simple reaction problem. We assume the reaction is a first-order homogenous reaction as the following:

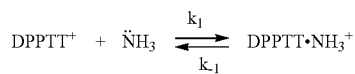

(Reaction S1)

with the gate induced hole carriers DPPTT$^+$ ($C_{DPPTT^+}$) homogenously distributed in the conductive channel, and analyte $NH_3$ ($C_{NH3}$) uniformly distributed through the film and inside the pores. The evolution of the DPPTT·$NH_3^+$ (C) can be formulated as, $$\frac{\partial C}{\partial t} = R \qquad \text{(Equation S3)}$$

$$R = k_1 C_{NH_3} C_{DPPTT^+} - k_{-1} C \qquad \text{(Equation S4)}$$

where t is the time, R is the charge-transfer reaction rate, $k_1$ and $k_{-1}$ represent the forward and backward reaction rate coefficients respectively. Combining equation S3 and S4 gives $$\frac{\partial C}{\partial t} = k_1 C_{NH_3} C_{DPPTT^+} - k_{-1} C = k_1 (C_0 - C) C_{NH_3} - k_{-1} C \qquad \text{(Equation S5)}$$

where $C_0$ is the gate voltage induced hole concentration, $C_{NH_3}$ is the ammonia concentration. Solving equation S5 yields $$C = \frac{C_0}{1 + \frac{k_{-1}}{k_1 C_{NH_3}}} \left(1 - e^{-(k_1 C_{NH_3} + k_{-1})t}\right) \qquad \text{(Equation S6)}$$

In this case, C corresponds to the reduced hole concentration directly. The source-drain current (I) is proportional to the charge carrier concentration (n) in the conductive channel following I∝σ=nqµ, wherein, q is the elementary charge and the mobility µ is constant. Therefore, the sensitivity relates to C as the following, $$\Delta I / I_0 = \qquad \text{(Equation S7)}$$

$$\frac{n' - n_0}{n_0} = \frac{-C}{C_0} = -\frac{1}{1 + \frac{k_{-1}}{k_1 C_{NH_3}}} \left(1 - e^{-(k_1 C_{NH_3} + k_{-1})t}\right)$$

where $n_0$ and n' are hole concentrations in the conductive channel before and after reaction with $NH_3$. Equation S7 informs that the response time and sensitivity are controlled by the reaction rate constants ($k_1$ and $k_{-1}$) and ammonia concentration ($C_{NH_3}$). Specifically, a higher forward reaction rate constant and higher ammonia concentration lead to faster response and better sensitivity. This relationship is illustrated in FIG. 18.

Example 5A. Nanoporous Small Molecule OFET for Formaldehyde Sensing

Figure 4A:
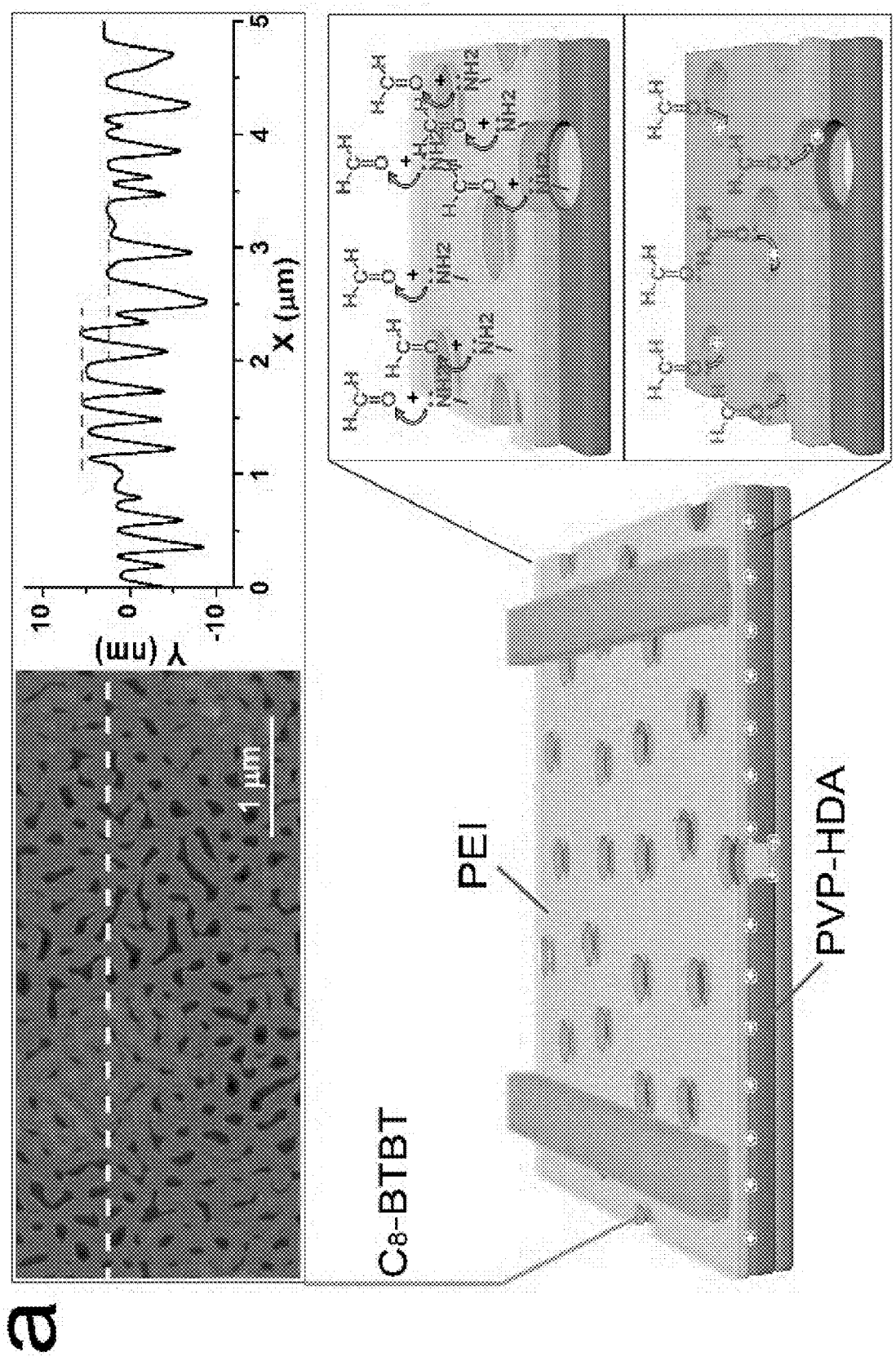
FIG. 4A-4B. Nanoporous $C_8$-BTBT OFET sensor. (a) Schematic of the device configuration. The top-contact, bottom-gate transistor device has a nanoporous semiconductor layer templated by the porous PVP:HDA layer, and covered by the PEI sensory layer. The AFM image and cross-sectional profile of the nanoporous $C_8$-BTBT semiconductor layer are shown. How formaldehyde molecules interact with the device is further illustrated. (b) Current response of $C_8$-BTBT/PEI transistor device with and without pores as compared to $C_8$-BTBT transistor device with and without pores to a wide range of formaldehyde gas concentration ($V_{GS}=-40V$, $V_{DS}=-40V$). The inset shows the magnified current responses at 1 ppb formaldehyde concentration. The nanopore size was approximately 500 nm on average.
Figures 21A, 21B, 21C, 21D, 21E, 21F:
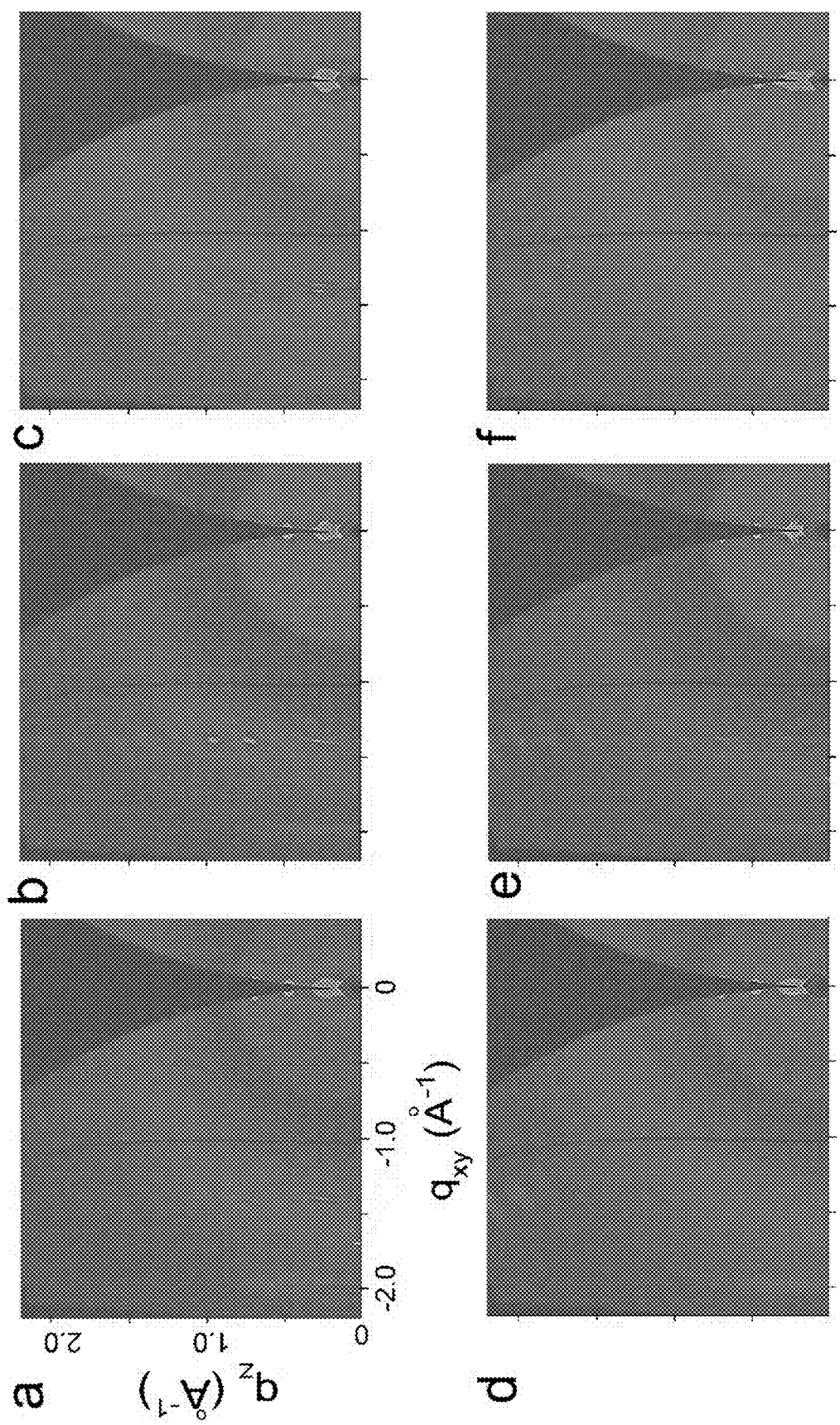
FIG. 21A-21F. GIXD images of $C_8$-BTBT thin films. GIXD images of (a-c) spin-coat and (d-f) printed $C_8$-BTBT films on PVP:HDA with (a, d) 0 nm, (b, e) 100 nm and (c, f) 400 nm pores. The printing direction is parallel to the incident beam, which is also the charge transport direction in the transistor devices.
Figures 26A, 26B:
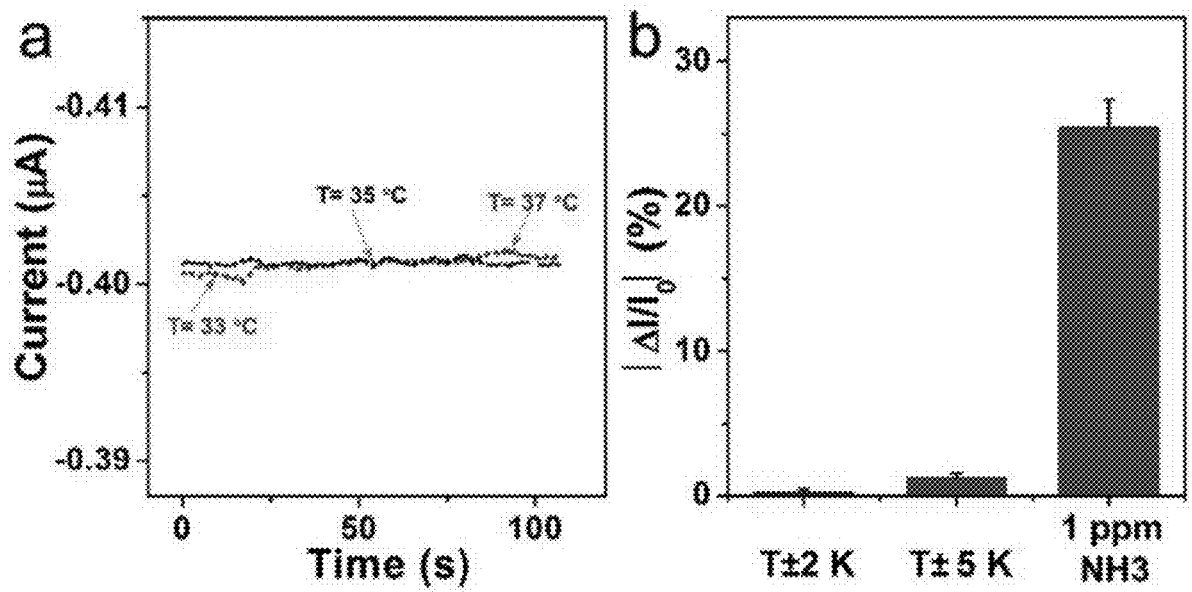
FIG. 26A-26B. Effect of temperature fluctuations on sensing performance. (a) Dynamic current response of nanoporous DPP-TT sensors at constant 35° C. and with varying temperatures between 33-37° C. (b) Sensitivity of nanoporous DPP-TT devices to temperature fluctuations vs. to 1 ppm $NH_3$.

To demonstrate the generality of our approach, we fabricated nanoporous OFET sensors using a small molecule semiconductor $C_8$-BTBT via both meniscus-guided coating and spin coating following a similar procedure (see Methods section below). Strikingly, we obtained large yet nanoporous single-crystalline domains with well-defined terraces (FIG. 4a). The structural integrity of these large crystalline domains was not affected by introducing a high area density of nanopores. The high crystallinity is manifested in the formation of micron-sized nanoporous terraces of 2.6 nm~2.8 nm in height, indicating that the terraces are comprised of a single molecular layer of $C_8$-BTBT. The high crystallinity is also evident from the appearance of high index peaks in the GIXD patterns (FIG. 21). In addition, only a few Bragg rods were observed due to the large size of crystalline domains well beyond the X-ray beam width, and therefore only very few grains were sampled by the X-ray. Interestingly, coating on nanoporous templates resulted in narrower diffraction peaks compared to the case of nonporous substrate (FIG. 26, and Table 7). Correspondingly, we measured higher hole mobility in the nanoporous transistor devices (Table 8). The mechanism by which nanopores improve molecular ordering in $C_8$-BTBT thin film is unclear. Nonetheless, high charge carrier mobilities obtained verify the continuity and charge percolation in the nanoporous thin films despite high pore densities (See also Table 9).

sensing is important and relevant for both environmental and health monitoring. Formaldehyde is a common carcinogenic indoor air pollutant with long-term exposure limits of only 16 ppb. In addition, formaldehyde in human breath is a biomarker for breast cancer. A breath formaldehyde concentration exceeding 1.2 ppm is strongly correlated with the disease condition, compared to the healthy level of 0.3 ppm on average. However, it remains challenging to detect formaldehyde ($CH_2O$) at such low concentration due to its weak electron donating and withdrawing abilities and therefore low reactivity with most organic semiconductors, including $C_8$-BTBT (black squares in FIG. 4b). Hence, we added a sensory layer to the $C_8$-BTBT OFET comprised of polyethyleneimine (PEI) rich in primary amine groups to enhance reactivity with $CH_2O$ (FIG. 4a). The nanoporous structure was maintained after PEI coating atop the $C_8$-BTBT layer

TABLE 7

Molecular packing in $C_8$-BTBT films characterized by GIXD.

| Organic thin films | Spin-coated film | | | Printed film | | |
| --- | --- | --- | --- | --- | --- | --- |
| | Without pores | 100 nm pores | 400 nm pores | Without pores | 100 nm pores | 400 nm pores |
| Lamella spacing (Å) | 26.54 ± 0.02 | 26.50 ± 0.02 | 26.50 ± 0.02 | 26.65 ± 0.02 | 27.84 ± 0.01<br>26.47 ± 0.02 | 26.95 ± 0.02 |
| FWHM of (002) peak (Å$^{-1}$) | 0.057 ± 0.002 | 0.047 ± 0.001 | 0.049 ± 0.001 | 0.046 ± 0.001 | 0.006 ± 0.000<br>0.028 ± 0.001 | 0.047 ± 0.001 |
| Stacking distance of peak at $Q_{xy}$ = 2 (Å$^{-1}$) | 3.20 ± 0.001<br>3.11 ± 0.000 | 3.17 ± 0.001 | 3.14 ± 0.001 | 3.16 ± 0.001 | 3.81 ± 0.000<br>3.16 ± 0.001 | 3.17 ± 0.002 |
| FWHM of peak at $Q_{xy}$ = 2 (Å$^{-1}$) | 0.045 ± 0.002<br>0.031 ± 0.000 | 0.024 ± 0.001 | 0.024 ± 0.002 | 0.074 ± 0.001 | 0.025 ± 0.002<br>0.011 ± 0.001 | 0.053 ± 0.003 |

TABLE 8

Charge transport characteristics of C8-BTBT based OFET devices.

| Pore size | Treated conditions[a] | Mobility[b] (cm$^2$V$^{-1}$s$^{-1}$) Avg(Max) | $V_{th}$ (V) Avg(Min) | Log ($I_{on}/I_{off}$) Avg(Max) |
| --- | --- | --- | --- | --- |
| 0 nm | Without PEI | 1.49 (1.83) | −22.4 (−20.2) | 6.3 (6.8) |
| | With PEI | 1.22 (1.26) | −26.2 (−24.3) | 5.9 (6.2) |
| 300 nm | Without PEI | 2.53 (2.8) | −13.2 (−3.0) | 4.6 (5.5) |
| | With PEI | 2.20 (2.7) | −33.0 (−30.0) | 5.3 (6.0) |

[a]The devices were fabricated with Ag as source-drain electrodes and measured in the air.
[b]Porosity in the device is not accounted for when calculating the mobility, which may lead to an underestimation of mobility in nanoporous devices.

TABLE 9

Device performance for bottom gate top contact (BGTC) and bottom gate bottom contact (BGBC) organic field-effect transistors based on 2,2'-((4E,4'E)-4,4'-(5-(2-ethylhexyl)-4,6-dioxo-5,6-dihydro-1H-thieno[3,4-c]pyrrole-1,3-(4H)-diylidene)bis(2-hexylthieno[3,4-b]-thiophene-6,4-(4H)-diylidene))dimalononitrile (2DQTT-o-B) with and without pores. Gold was deposited as source-drain electrodes. The device channel length and width are 60~80 μm and 4500 μm, respectively.

| Devices | Structure | $\mu_{Sat}$[a] (cm$^2$V$^{-1}$s$^{-1}$) | Vth (V) | Log ($I_{on}/I_{off}$) | $\mu_{Linear}$[b] (cm$^2$V$^{-1}$s$^{-1}$) |
| --- | --- | --- | --- | --- | --- |
| Without pores | BGTC | 0.38 ± 0.05 | 6.6 ± 1.4 | 4.5 ± 1.2 | 0.17 ± 0.02 |
| | BGBC | 0.05 ± 0.03 | 3.6 ± 3.0 | 4.8 ± 0.2 | 0.03 ± 0.01 |
| With pores | BGTC | 0.24 ± 0.01 | 4.8 ± 0.6 | 4.0 ± 0.5 | 0.12 ± 0.01 |
| | BGBC | 0.07 ± 0.01 | 1.9 ± 2.2 | 4.4 ± 0.4 | 0.08 ± 0.01 |

Figure 4B:
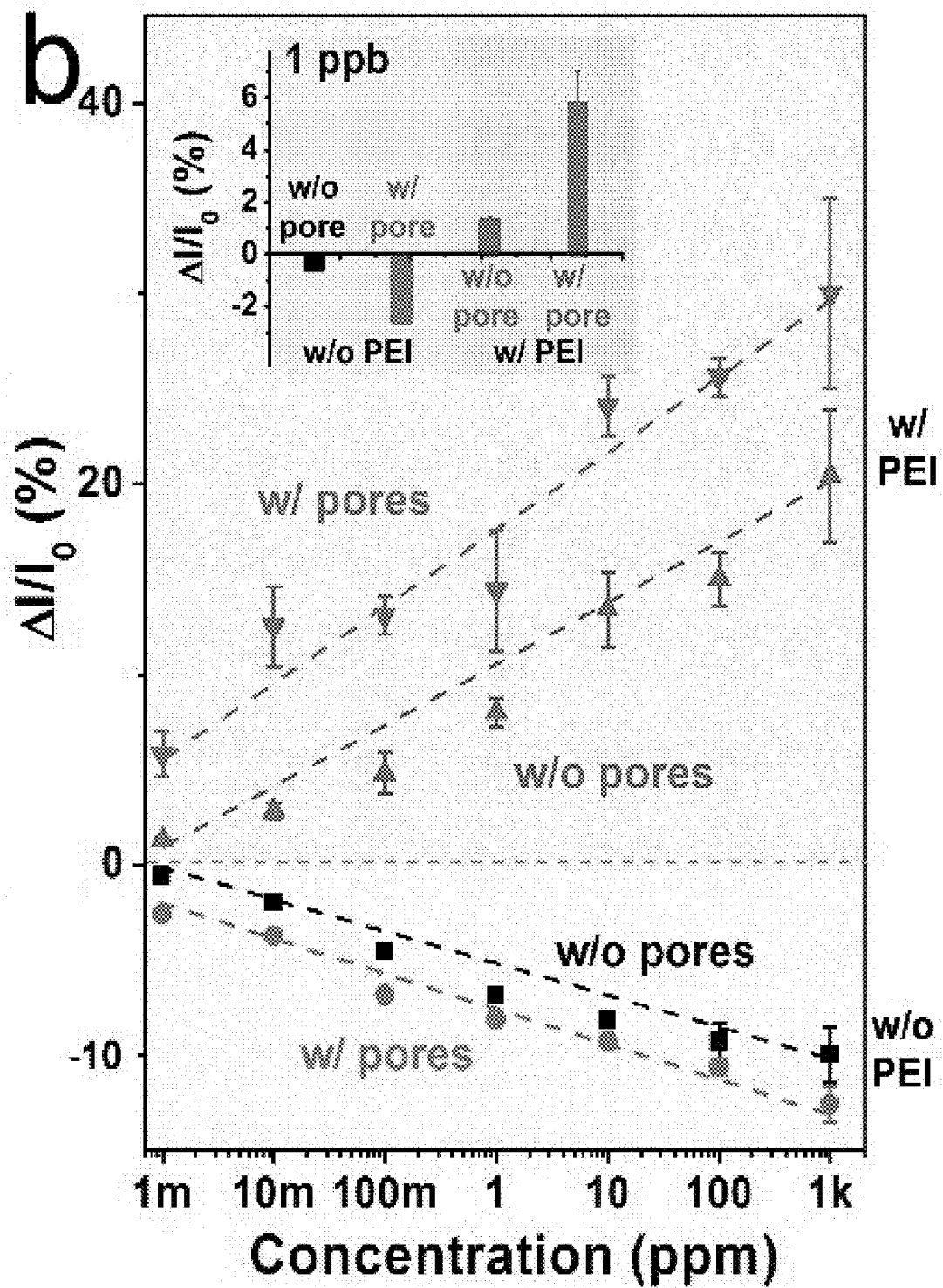
Figures 22A, 22B:
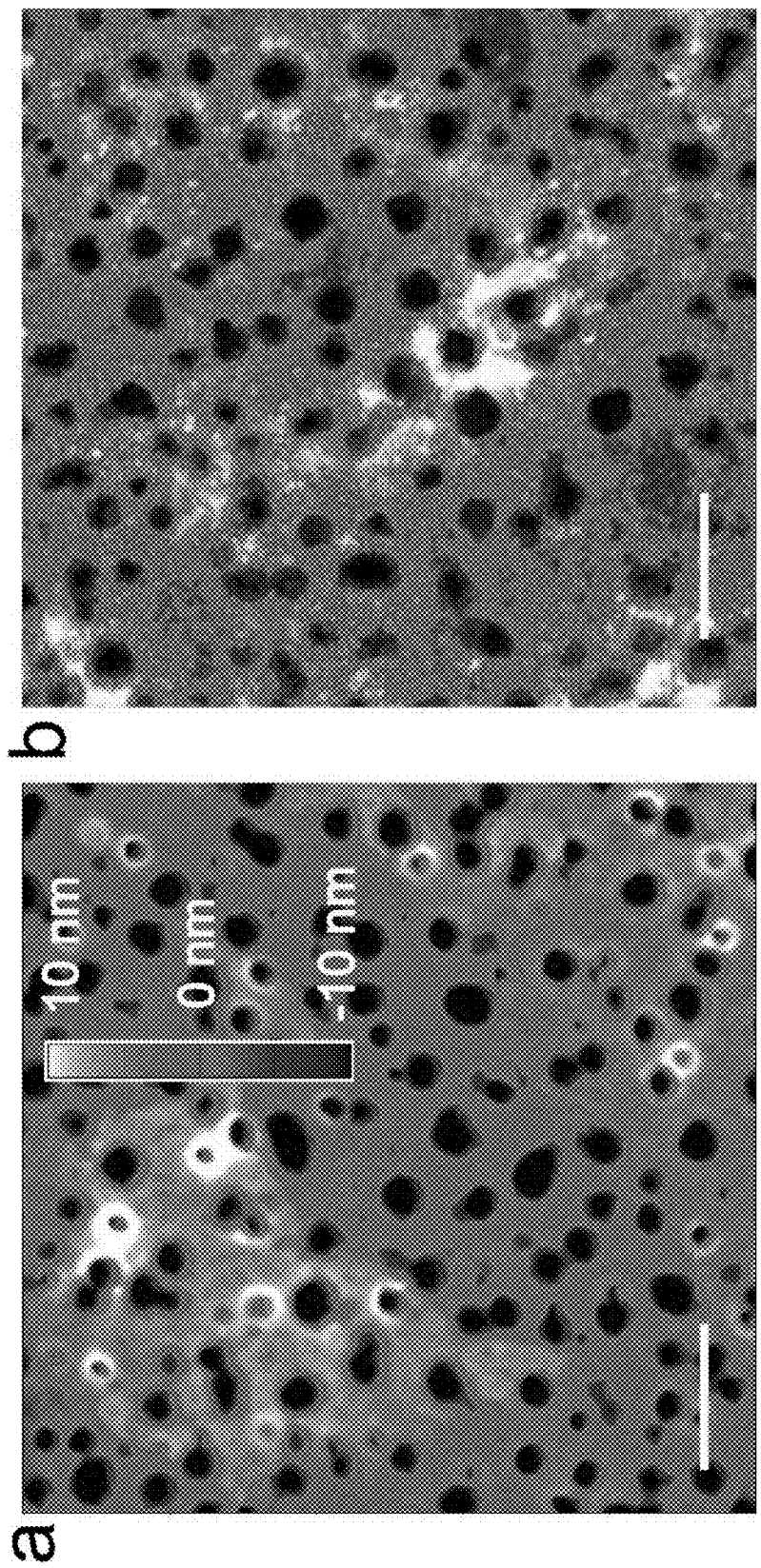
FIG. 22A-22B. AFM image for $C_8$-BTBT film (a) before and (b) after PEI coated. The device was deposited with pores. Scale bar: 1 μm.
Figure 23:
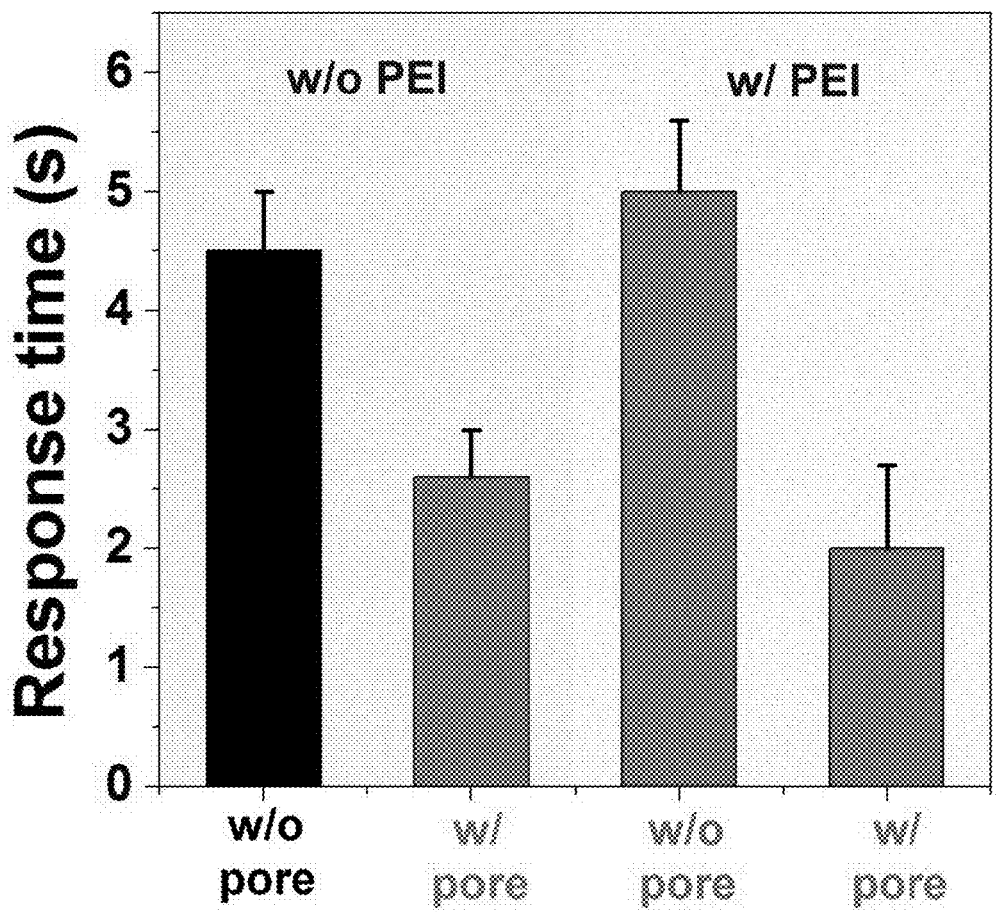
FIG. 23. Current response time for formaldehyde sensor for porous and nonporous $C_8$-BTBT device with and without PEI.
Figure 24:
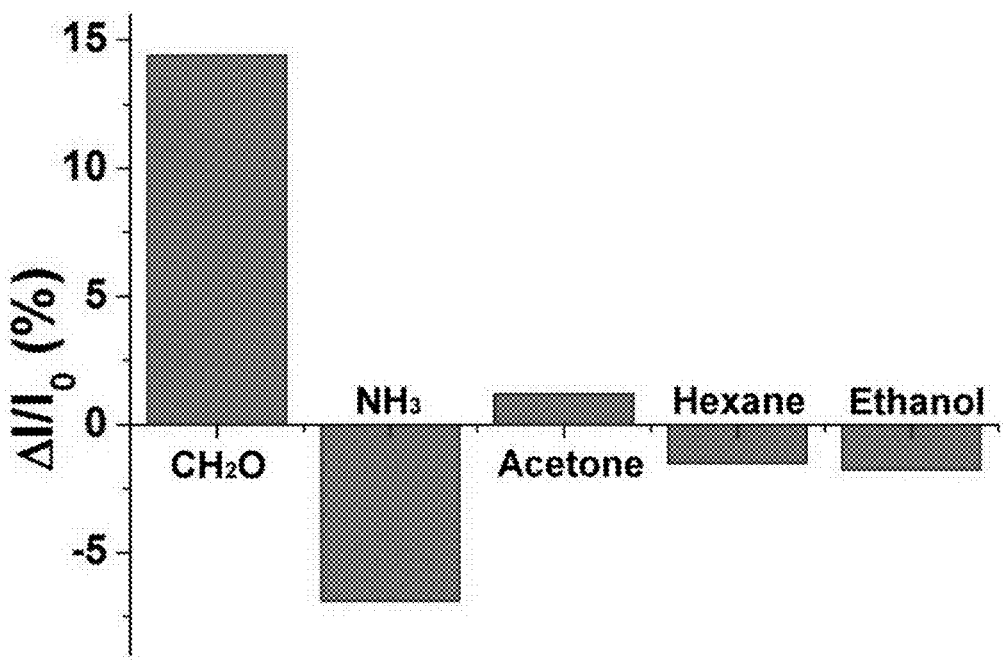
FIG. 24. (a) Selectivity of PEI coated nanoporous $C_8$-BTBT sensors. Figure shows current response of nanoporous $C_8$-BTBT OFETs to various gases with a concentration of 10 ppb. The sensing measurements were carried out with a gate voltage of −40 V and drain voltage of −40 V. (b) Graph of samples versus current response.

[a]Saturation mobility, which is measured at $V_{DS}$ = 100 V;
[b]Mobility measured at $V_{DS}$ = 2 V and reflect the carrier mobility at linear regime We next tested the sensing performance of $C_8$-BTBT OFET for trace formaldehyde detection. Formaldehyde (FIG. 22). The as fabricated nanoporous $C_8$-BTBT/PEI OFET exhibited excellent $CH_2O$ sensing performance reaching an unprecedented detection limit of 1 ppb. Furthermore, introducing nanopores increased the sensitivity of nonporous devices by an order of magnitude from 0.6% to 5.8%. Without PEI, nanopores also enhanced device sensitivity, but to a lesser extent (FIG. 4b). From the opposite current responses of devices with vs. without PEI, we infer a doping-dedoping sensing mechanism as the following. First, PEI acts as an electron donor doping the hole-conducting $C_8$-BTBT, which brings a decrease in current; when the carbonyl groups of $CH_2O$ reacts with the amine groups of PEI, the $C_8$-BTBT layer is dedoped and the current rises back. The PEI layer enhances the reactivity with $CH_2O$ while nanopores expose the reactive conducting channel originally buried in the $C_8$-BTBT layer. Both factors combined leads to the ultrasensitivity for $CH_2O$ sensing. As far as we know, this is the best sensing performance among OFET-based formaldehyde sensors reported so far. Typical detection limits between 1 ppm to 1000 ppm. We further show that the nanoporous $C_8$-BTBT sensors exhibit fast response and good selectivity for $CH_2O$ among major reactive VOCs (FIG. 23 and FIG. 24), enabling potential applications in ultrasensitive environmental and health monitoring.

Example 5B. Flexible Nanoporous OFETs for Breath Sensing

Figure 5A:
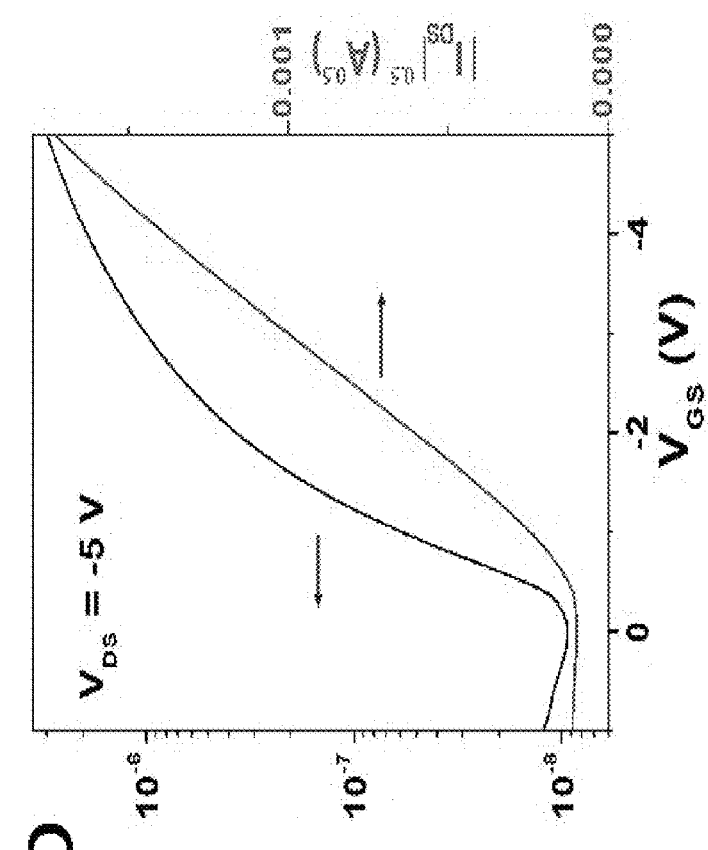
FIG. 5A-5F. Flexible sensor chip. (a) Photograph of a flexible gas sensor. The devices were fabricate with a structure PET/ITO/PVP:HDA/porous PVP:HDA/DPP-TT/electrodes. DPP-TT were deposited via the printing method. (b) Transfer curve of the transparent OFET. (c) Current response of the porous DPP-TT devices for $NH_3$. The average pore diameter is 600 nm. (d) Current responses of printed and spin-coated devices towards various VOCs at a concentration of 1 ppm. (e) Dynamic-sensing response curve of porous DPP-TT devices. Healthy breath sample (collected from a health female) was injected first. Subsequently, breath samples dosed with additional $NH_3$ at concentration of 10 ppb, 100 ppb, 1 ppm and 10 ppm was tested, to simulate the disease condition. (f) Comparison of current responses between healthy breath (without dosing $NH_3$; lower block) and simulated breath gas with additional $NH_3$ dosed at various concentrations (upper block).
Figure 5B:
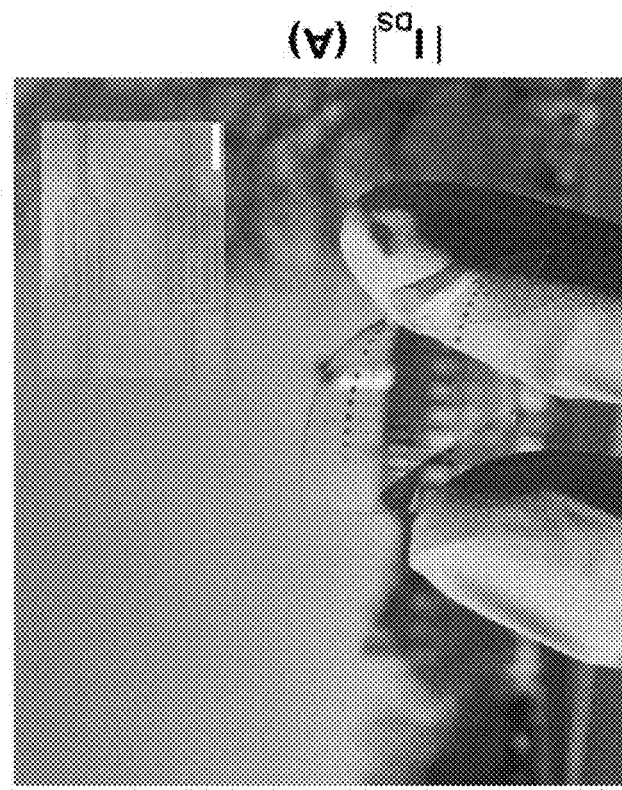
Figures 5C, 5D:
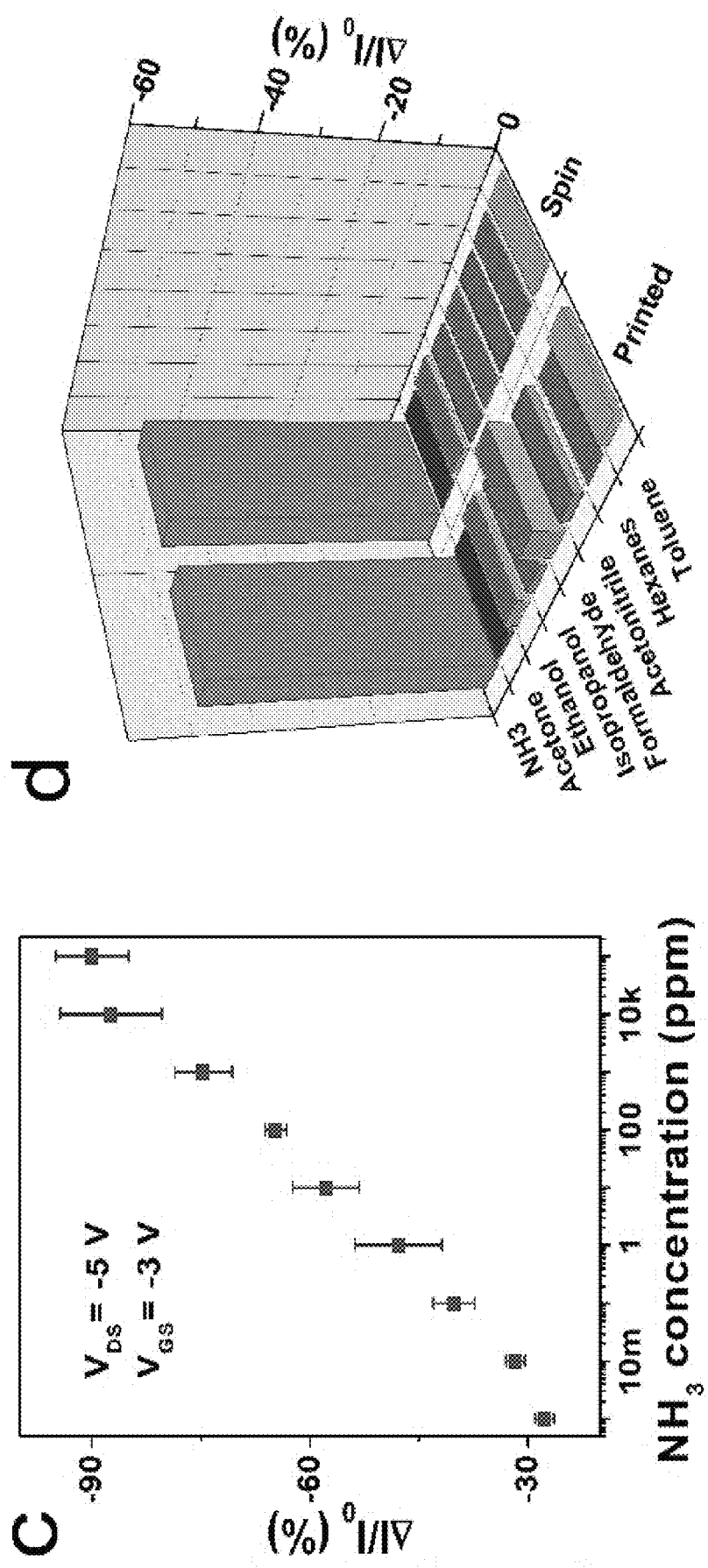
Figure 25:
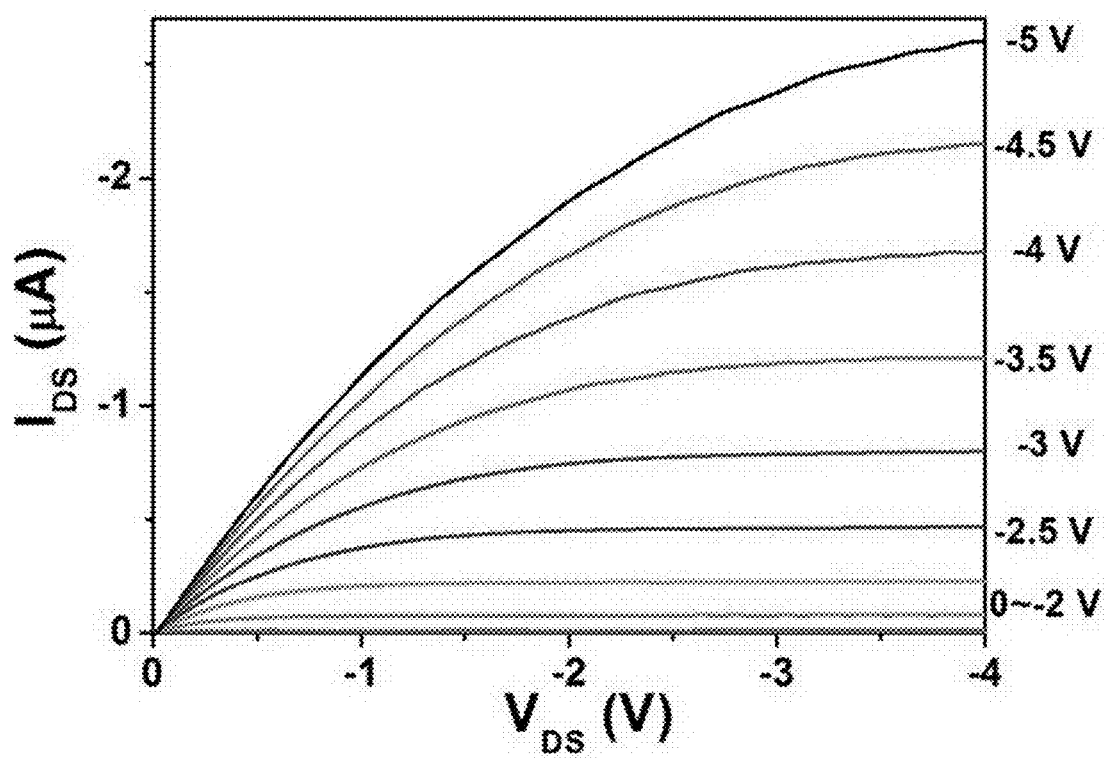
FIG. 25. Output characteristics of flexible OFET with DPP-TT as the semiconductor layer.
Figure 27:
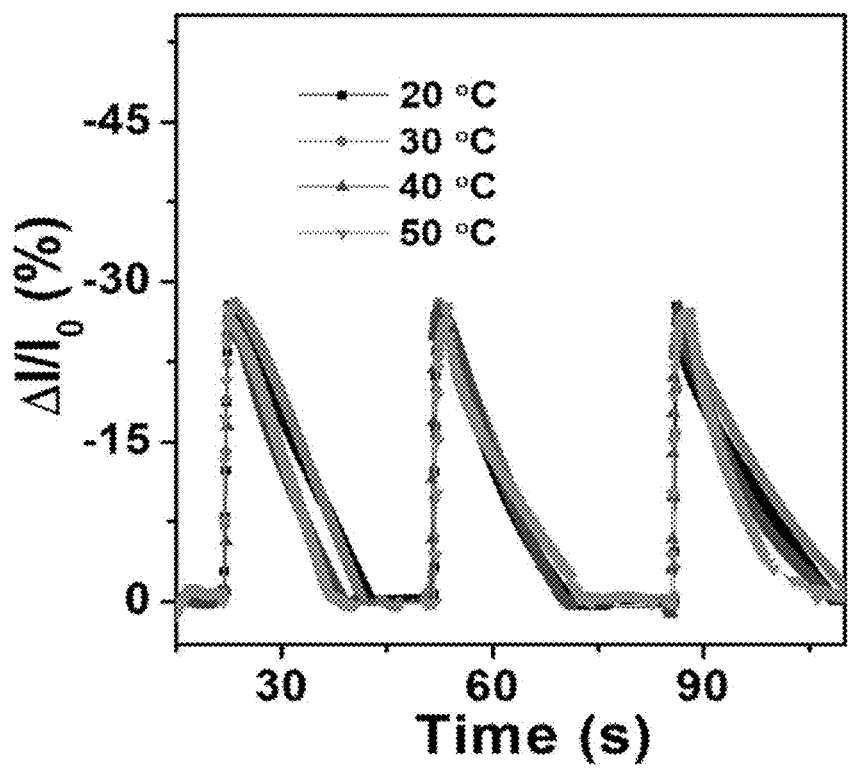
FIG. 27. Effect of environment temperature to sensitivity. Dynamic-sensing response curve of nanoporous DPP-TT FET devices to 1 ppb ammonia under various environment temperatures. The pore size is ~600 nm. The sensitivity $\Delta I/I_0\%$ to ammonia was found independent of environment temperature. This result is not surprising, because both the current change $\Delta I$ and the baseline I0 vary with respect to environment temperature and the effects cancel out.
Figures 28A, 28B:
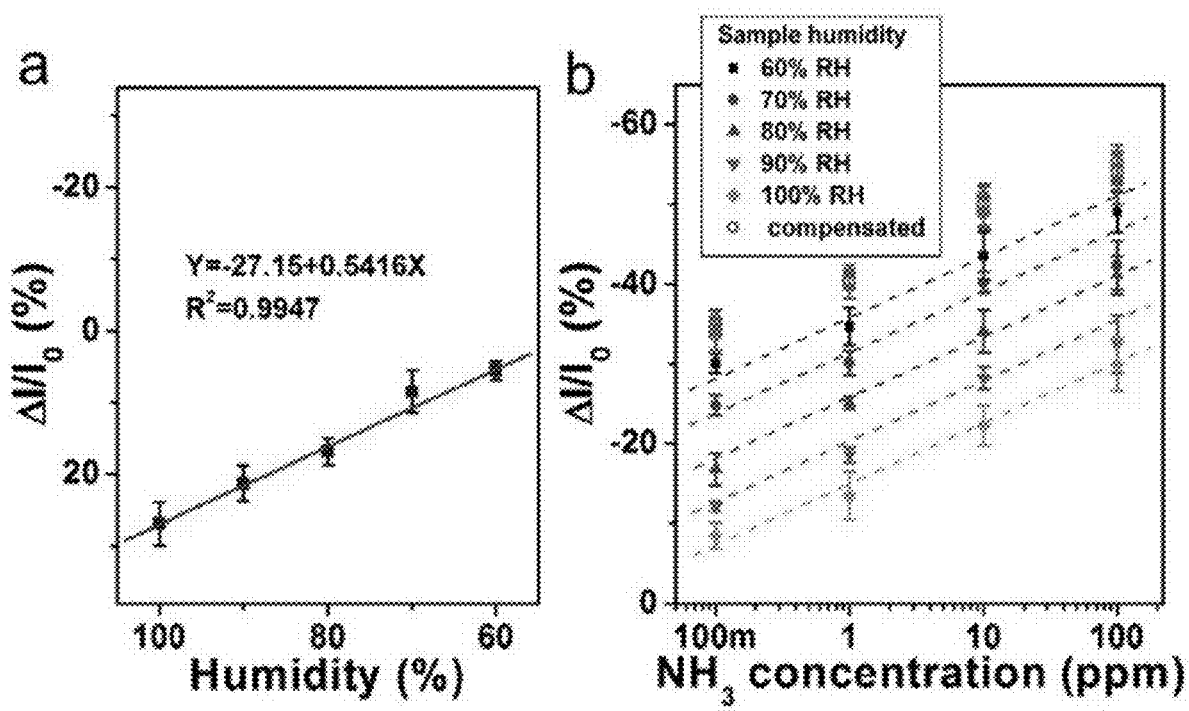
FIG. 28A-28B. Effect of sample humidity on sensitivity to NH3 gas. (a) Current response of the porous DPP-TT devices to air samples of various RH. To mimic the conditions during practical applications, we employed air as the carrier gas and performed the measurements in the ambient condition, at RH=56%. The humidity calibration curve yields 0.54% current change ($\Delta I/I_0\%$) per 1% variation in sample RH. This is equivalent to $1.7 \times 10\%$ change in $\Delta I/I_0\%$ per 1 ppm change of water concentration in the sample. (b) Uncompensated (closed symbols) and compensated (open circles) current response to various concentrations of ammonia. The error bars were calculated from more than 5 devices.
Figure 29:
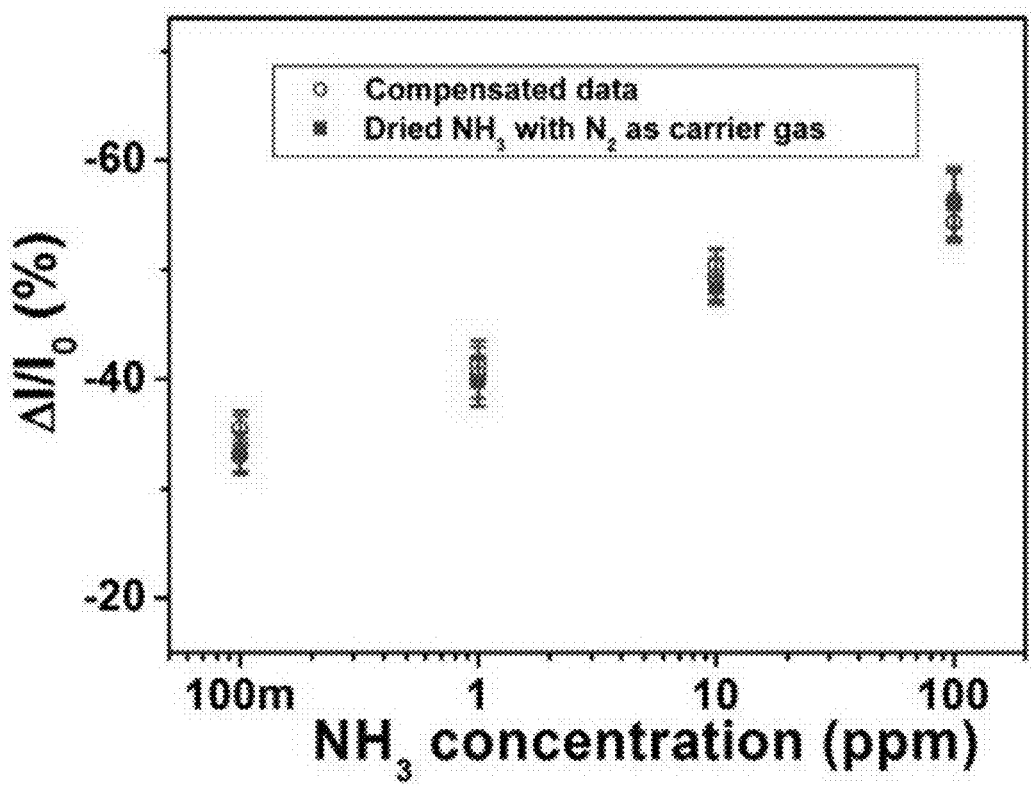
FIG. 29. Effectiveness of sample de-humidification using sodium hydroxide desiccants. Current responses of dried ammonia are compared with those of compensated humid samples. The NH3 was pre-treated with desiccant for 3 h and measured in the glovebox (RH~0).

The ultralow detection limit and ultrafast response of nanoporous OFET sensors open avenues for a wide range of applications in health and environmental monitoring. Here, we demonstrate low-voltage DPP-TT OFET sensor chip fabricated on flexible substrate and its application in sensing breath ammonia (FIG. 5). Ammonia is a common volatile organic compound found in human breath. The breath ammonia concentration is typically in the hundred ppb range; its rise to the ppm level strongly correlates with renal failure, as well as liver failure and Alzheimer's disease. The real-time detection of breath ammonia concentration contributes to personal healthcare monitoring. We adopted high capacitance PVP:HDA as the dielectric layer to reduce the operation voltage, and the ITO-coated polyethylene terephthalate (PET) as the flexible substrate in OFET fabrication (FIG. 5a). The transistor devices exhibited excellent transfer and output characteristics operating at low voltage (FIG. 5b and FIG. 25). Moreover, the ammonia sensing performance of low-voltage flexible devices (FIG. 5c) was comparable to that of OFETs fabricated on $SiO_2$/Si substrates (FIG. 3e). To demonstrate a clear path towards practical application in breath sensing, the effects of temperature and humidity fluctuations as well as mechanical bending on device sensitivity were further investigated. The porous DPP-TT devices exhibit excellent temperature stability within the range of breath temperature fluctuations (FIG. 26). The sensing performance is also stable against large fluctuations of environment temperature between 20~50° C. (FIG. 27). In terms of humidity effect, human breath usually exhibits >80% relative humidity (RH), which does significantly impact the device sensitivity (FIG. 28a). However, such humidity effect can be fully compensated following an established procedure (FIG. 28b). In other words, the sensitivity to humidity and VOC is additive. Alternatively, the humidity effect can be eliminated via sample de-humidification (FIG. 29).

Figure 30:
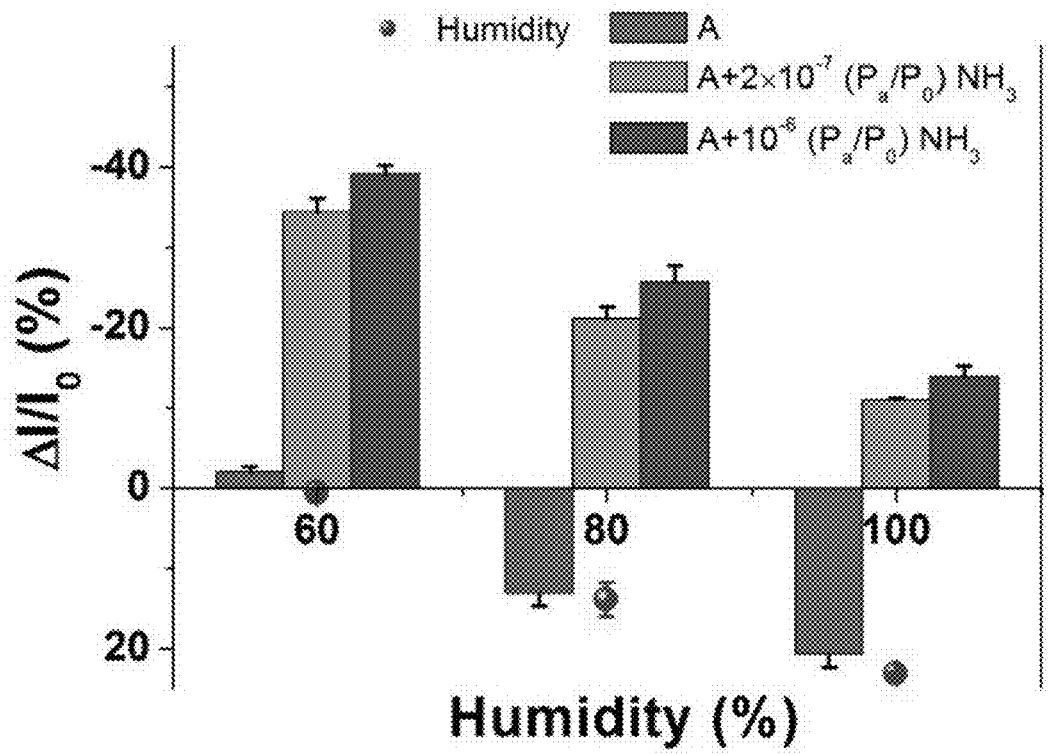
FIG. 30. Selectivity to ammonia in VOC mixture of high sample humidity.

We next investigated the selectivity of the flexible OFETs. Shown in FIG. 5d, the nanoporous DPP-TT sensors exhibited high selectivity for ammonia among major VOCs in breath tested at 1 ppm. Furthermore, such high selectivity is not undermined by the presence of common confounding factors in breath, such as a background of VOC mixtures, or a high sample humidity (FIG. 30). We also studied the effect of substrate bending on charge carrier mobility and sensitivity shown in FIG. 31.

Figure 5E:
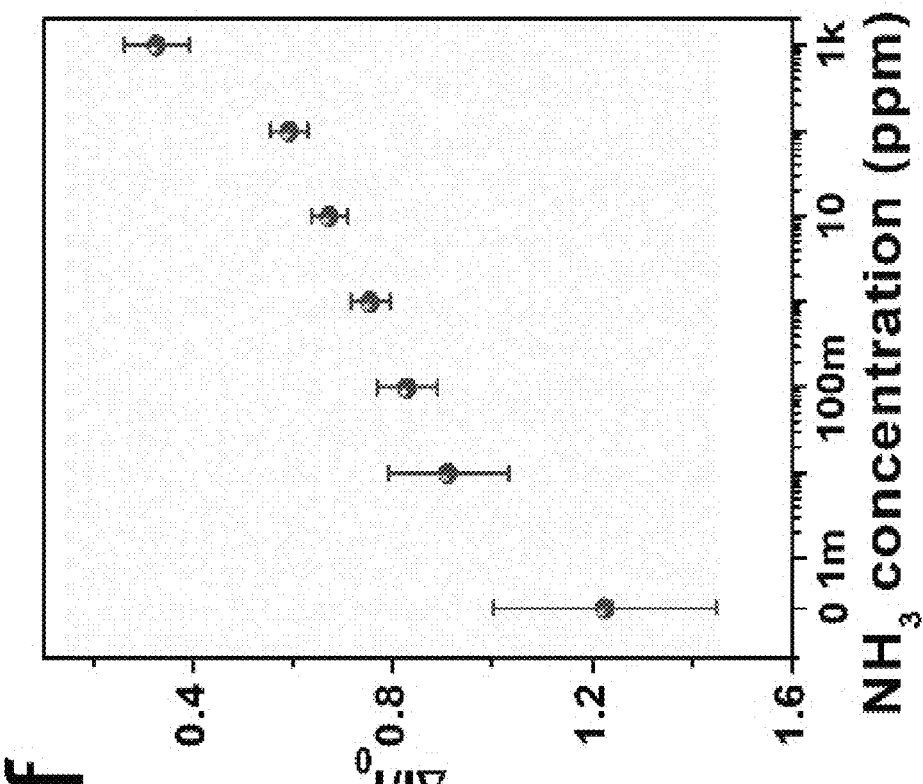
Figure 5F:
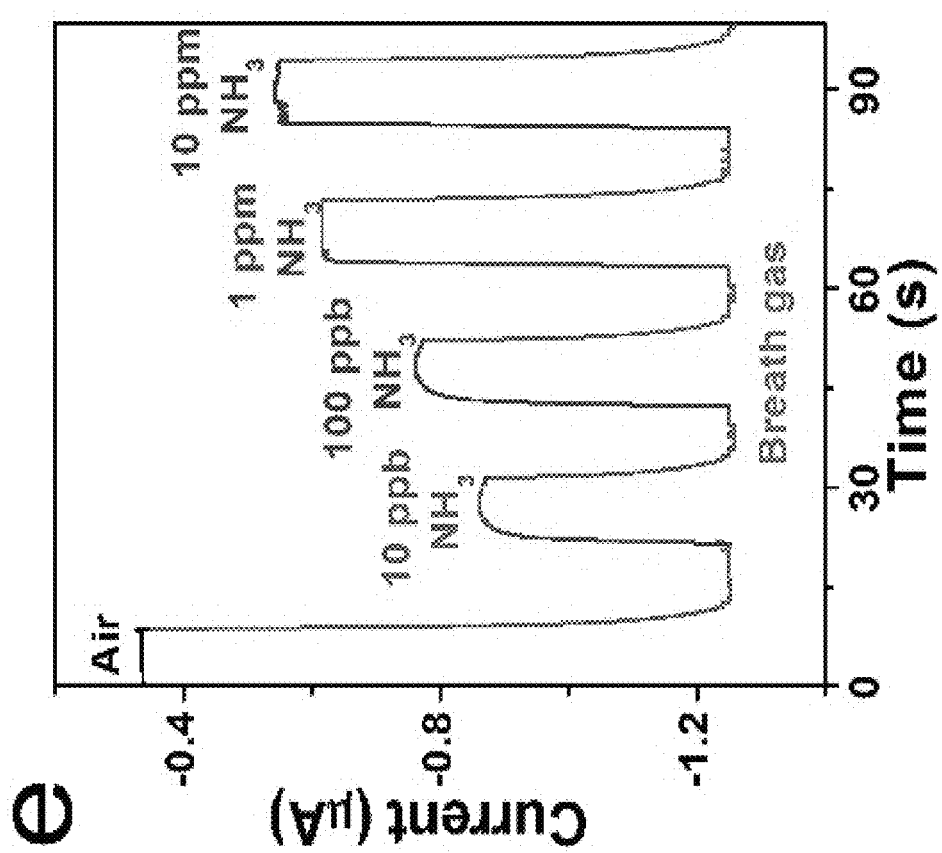
Figure 32:
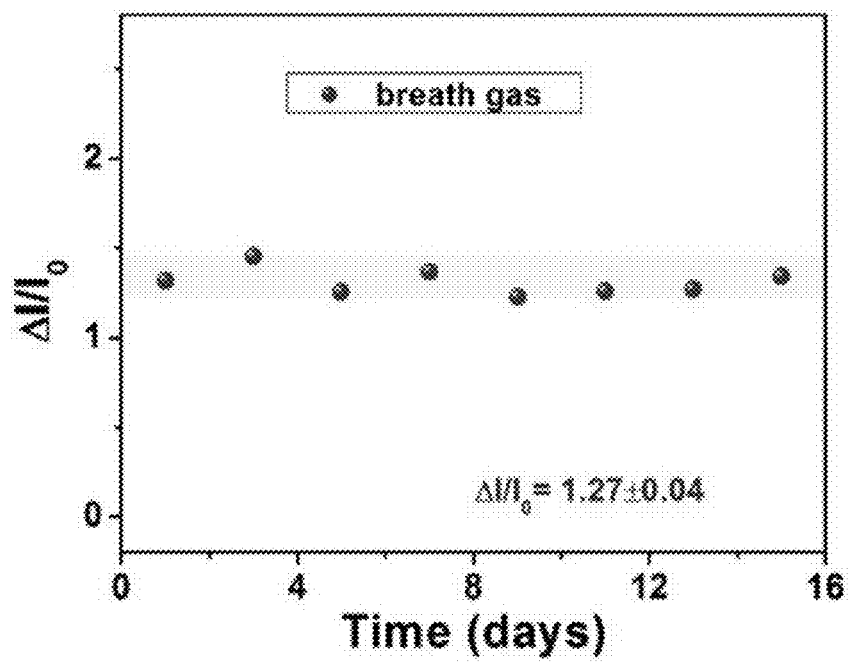
FIG. 32. Baseline for the current response of DPP-TT based breath sensors to health breath of an individual over a 15-day period. The devices were fabricated on flexible porous substrate and the breath gases were collected from the same volunteer at the same time of the day.
Figure 33:
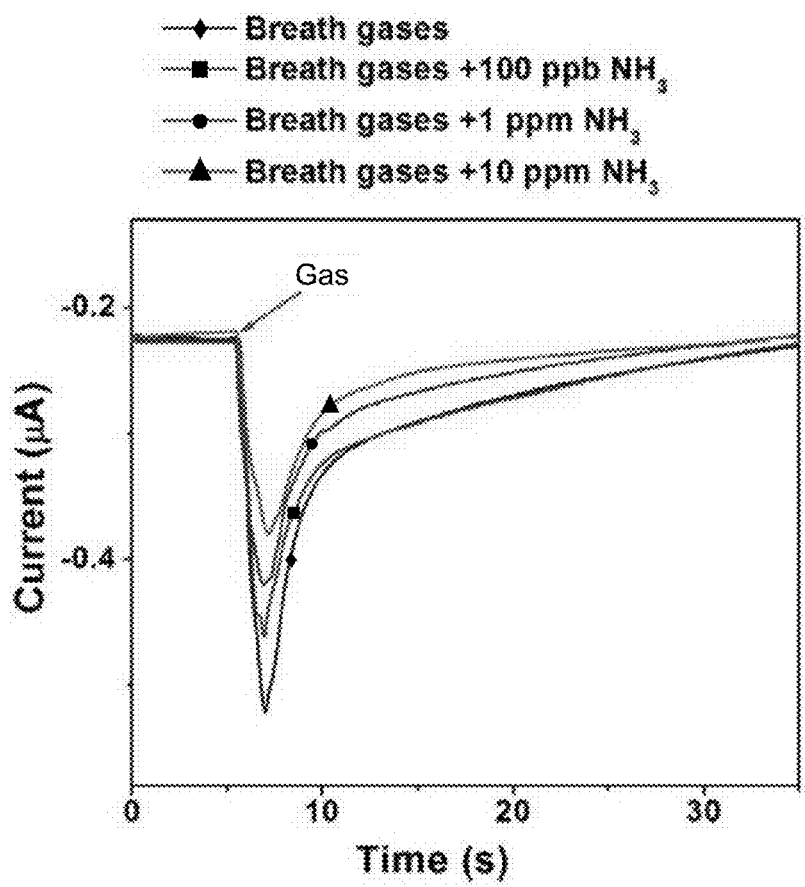
FIG. 33. Dynamic monitoring curve of nanoporous flexible breath sensor to healthy breath and simulated breath with higher than unusual ammonia concentrations. For the simulated breath sample, 100 ppb, 1 ppm and 10 ppm $NH_3$ were added to the health breath gas respectively.
Figure 34:
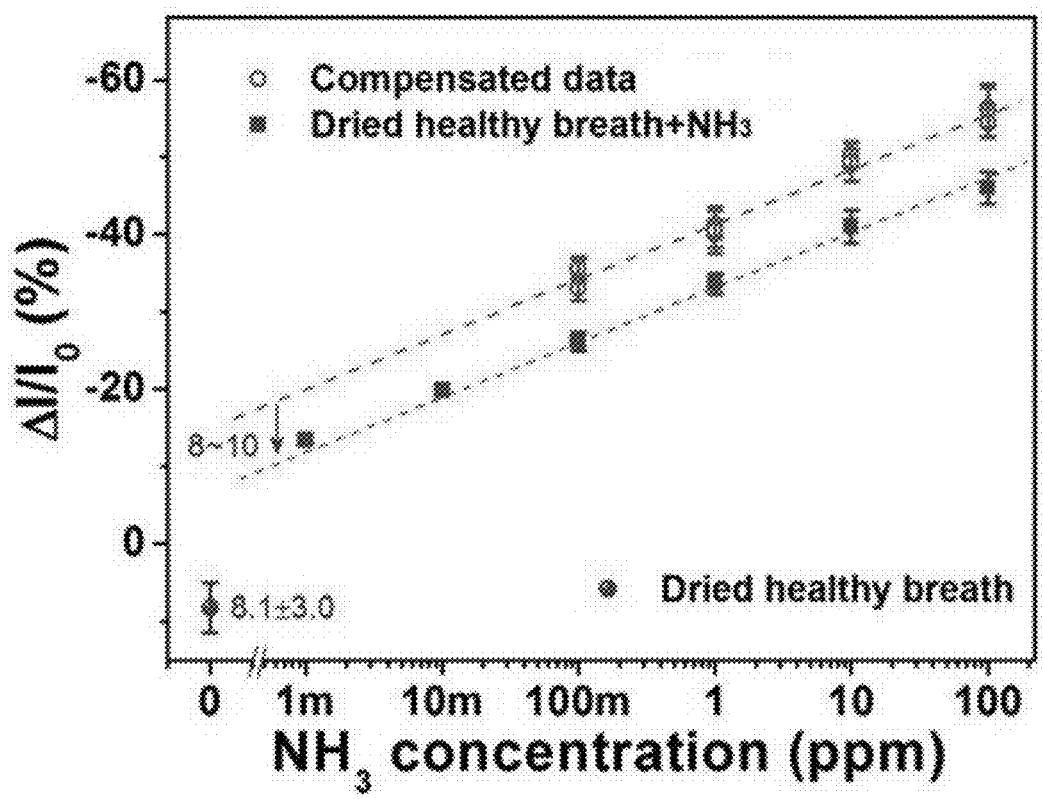
FIG. 34. Current response to dried healthy breath samples with various NH3. All of the samples were pre-treated with desiccant for 3 h and measured in the glovebox (RH~0).
Figure 35:
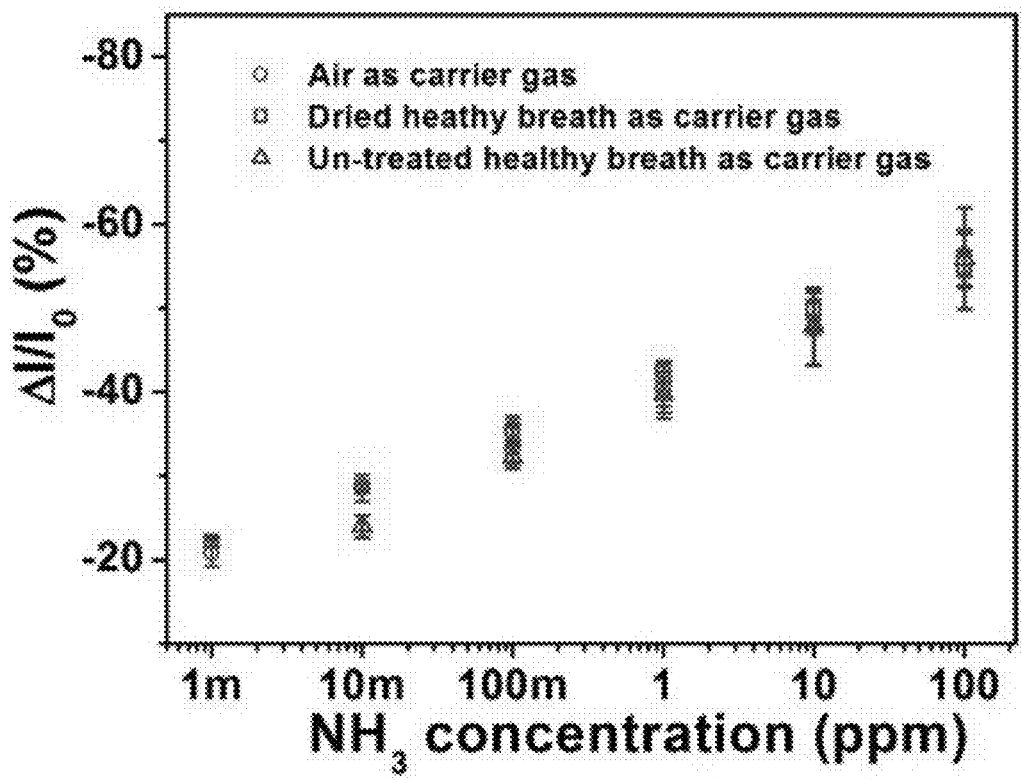
FIG. 35. Comparison of current responses to ammonia compensated with air (circle), dried health breath (squares) and untreated healthy breath gas (triangle) as the carrier gas, over a wide range of ammonia concentration from 10 ppb to 100 ppm. The error bars were calculated with more than 5 devices.
Figure 36:
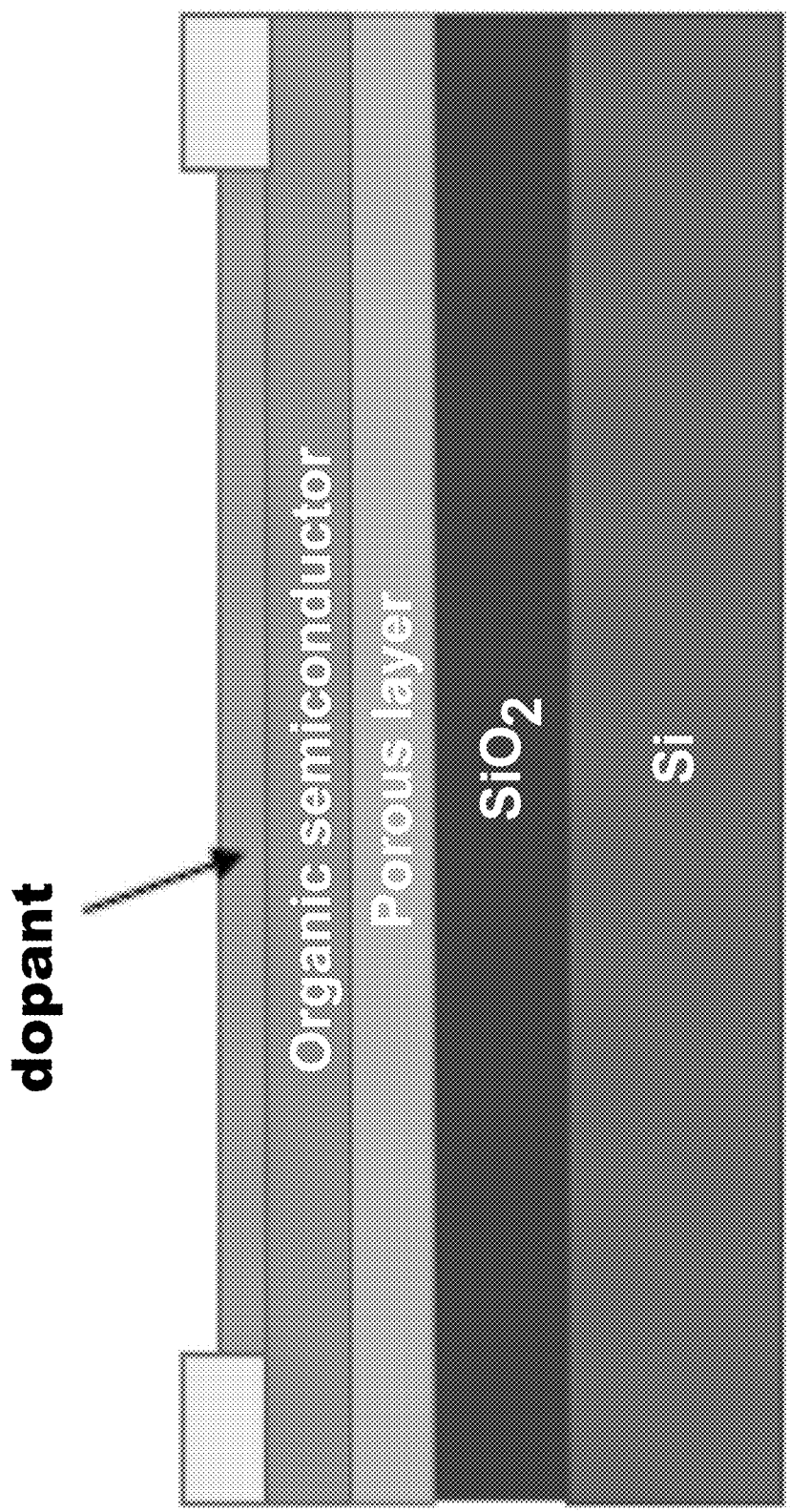
FIG. 36. Chemical doping with porous structures. Schematic illustration of chemical doping with porous organic thin film.
Figure 37:
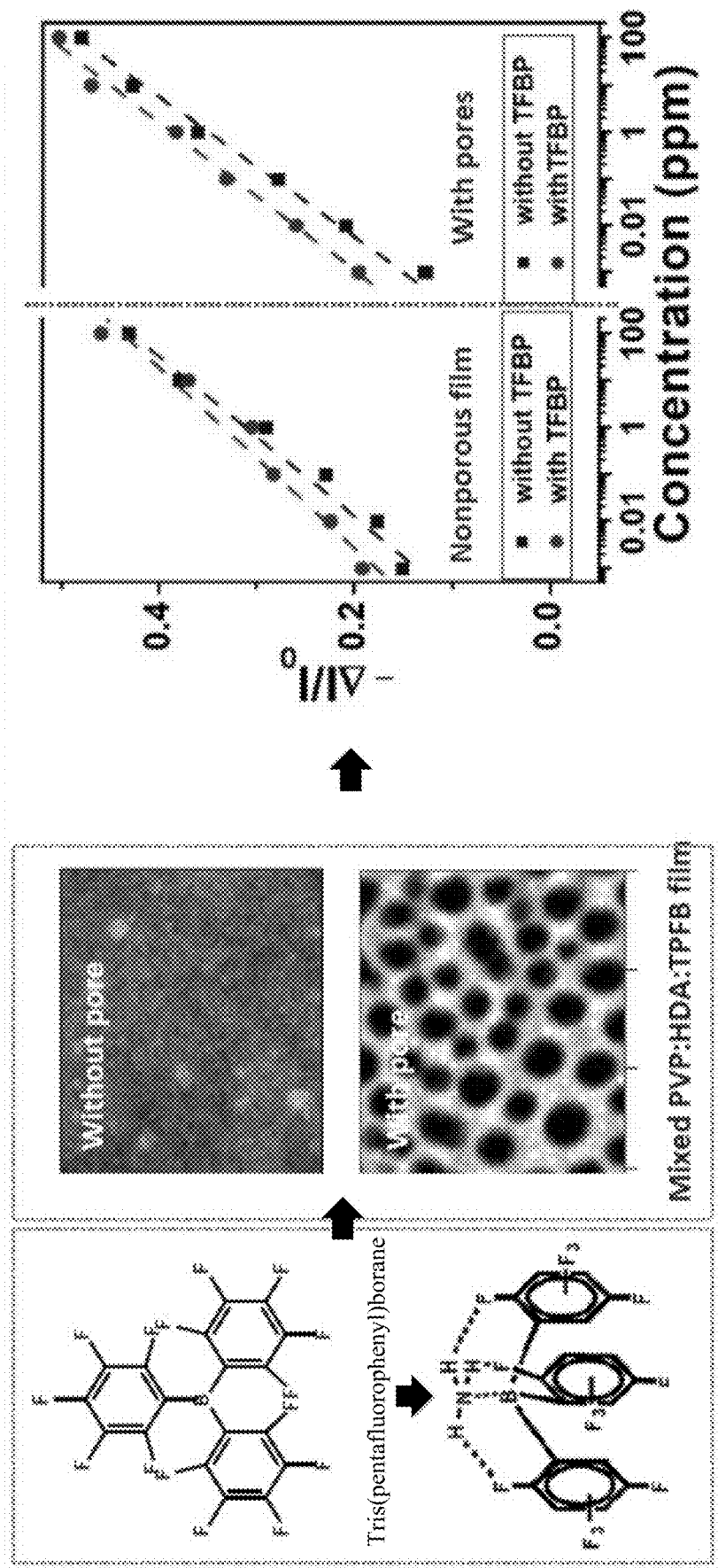
FIG. 37. TFBP doped DPP-TT OFETs as ultrasensitive ammonia sensor
Figure 38A:
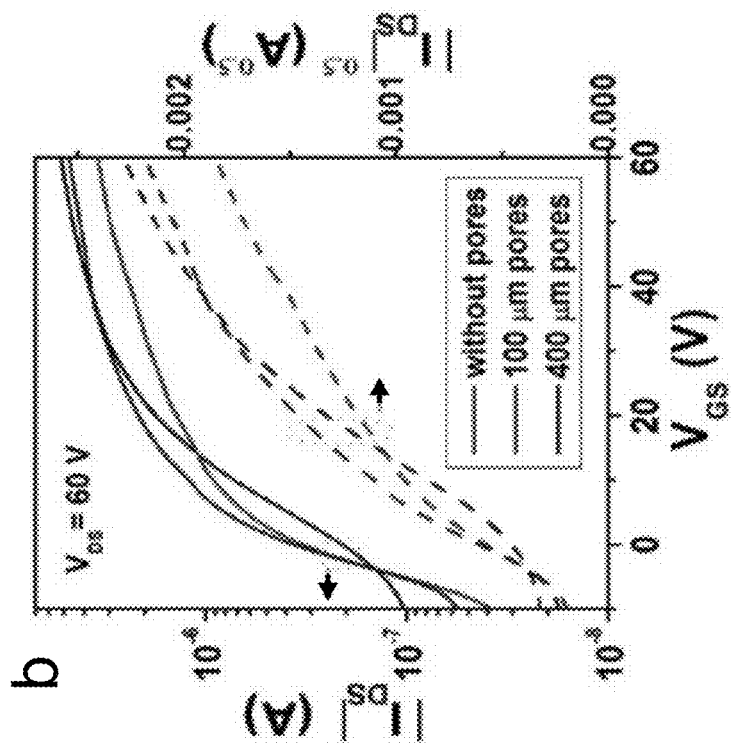
FIG. 38A-38B. PEI doped DPP-TT devices for demonstrating conversion from p-type of n-type transistors via doping. (a) Electron and hole mobility as a function of doping concentration. The organic semiconductor layer contains pores with average diameter of 0, 100 and 400 nm. (b) Transfer curves of doped OFETs comparing various surface nanostructures FIG. 39. Cross-polarized optical micrograph of $C_8$-BTBT films (top) coated with PFI (middle) or $F_4$-TCNQ (bottom) dopants. The arrow denotes the printing direction and C8BTBT films were printed at a speed of 1.3 mm s$^{-1}$ from 7.5 mg/ml $C_8$-BTBT/chloroform solution.
Figure 38B:
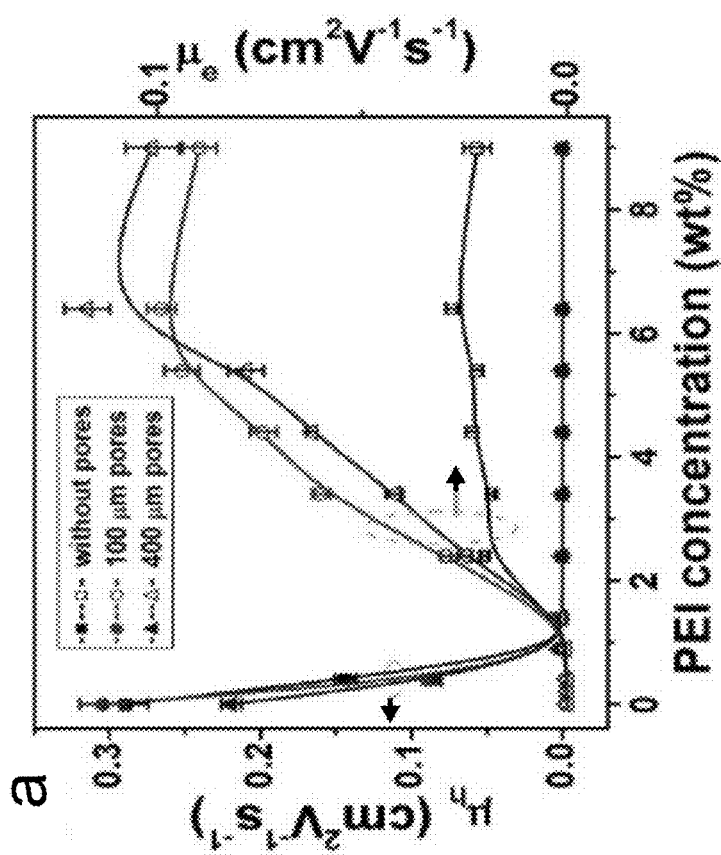
Figure 39:
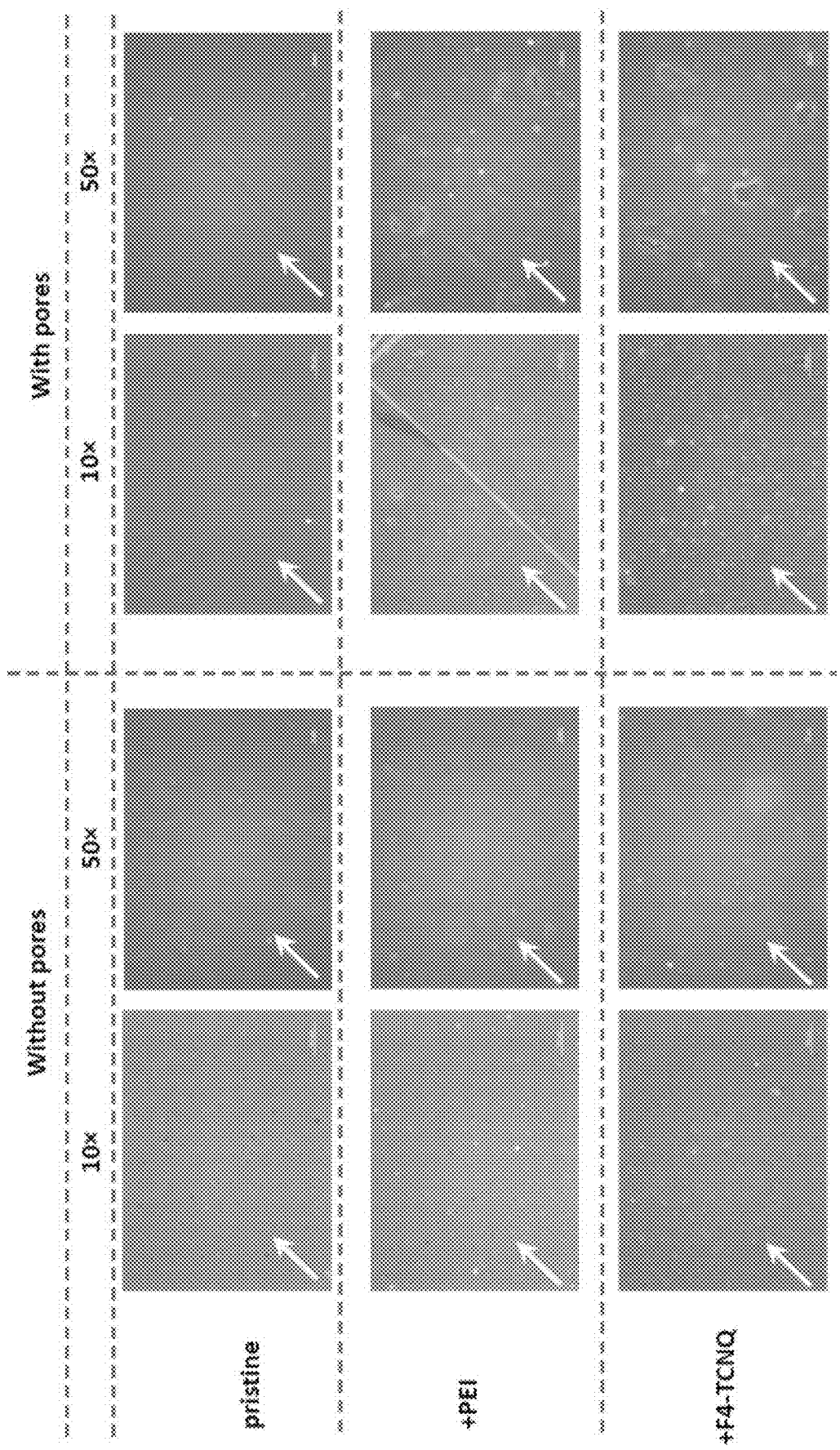
Figure 40:
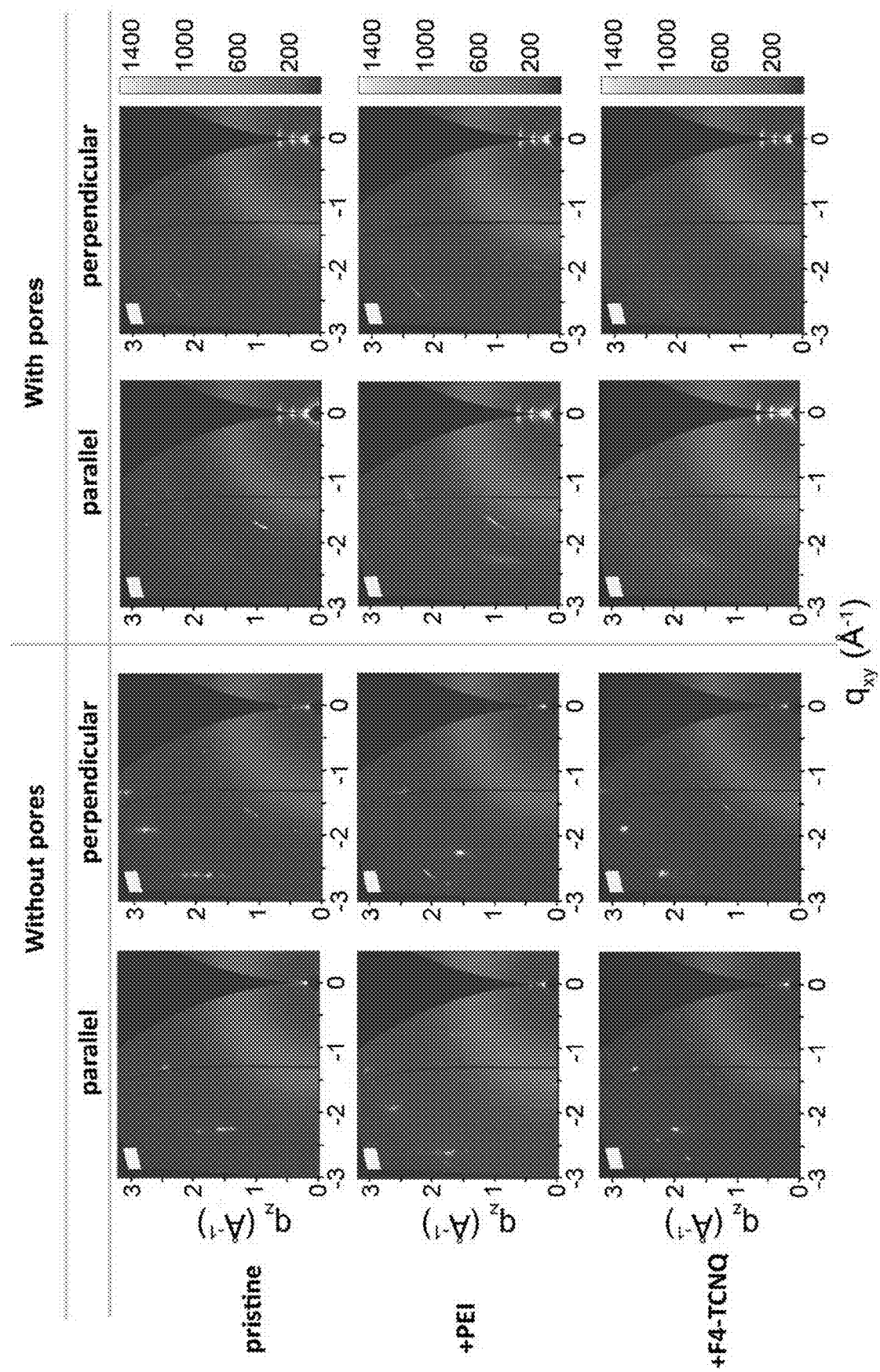
FIG. 40. Grazing incidence X-ray diffraction images of $C_8$-BTBT films (top) coated with PEI (middle) or $F_4$-TCNQ (bottom)
Figure 41:
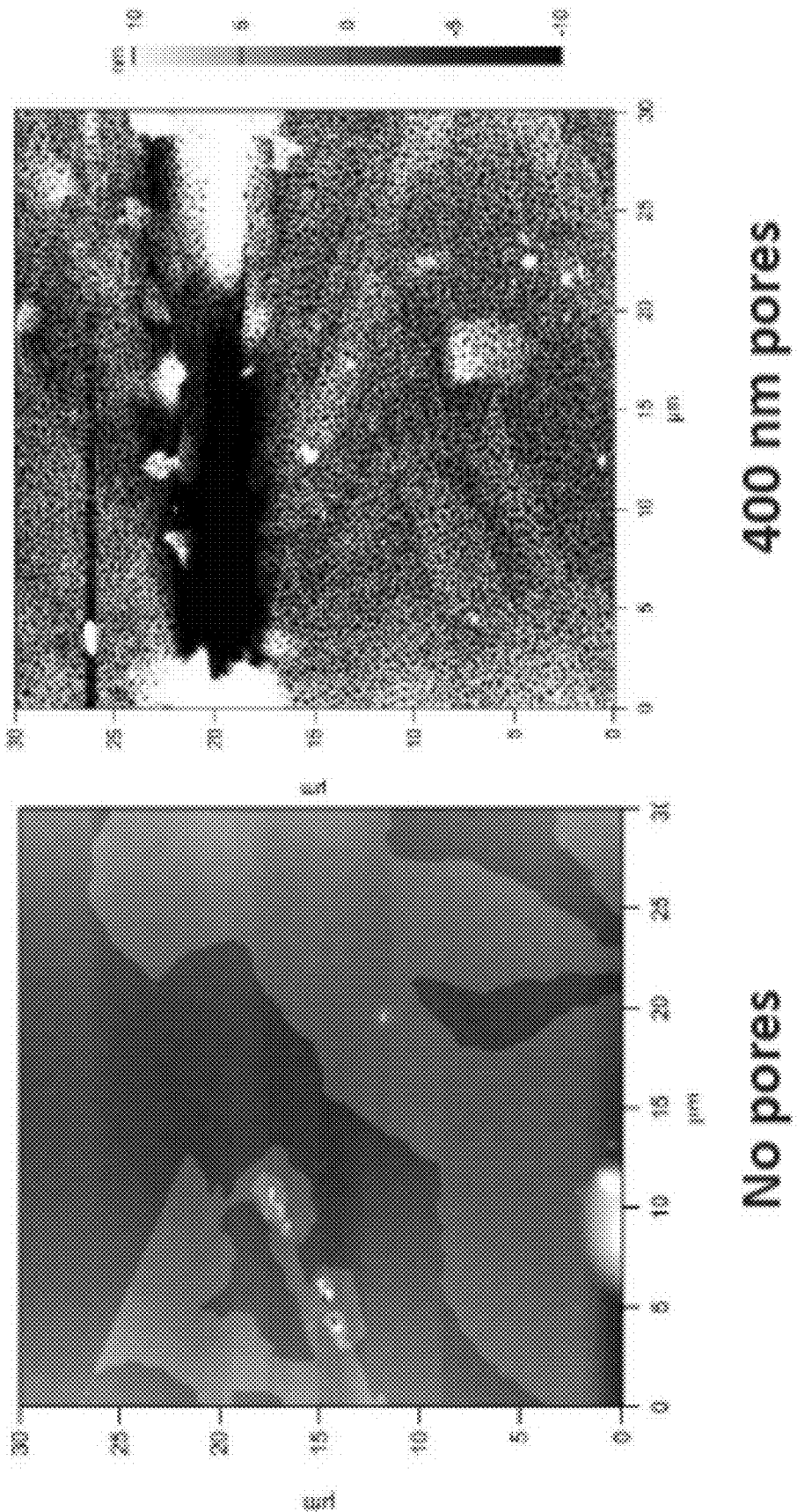
FIG. 41. AFM images of PEI doped $C_8$-BTBT film (left) without and (right) with pores.
Figure 42:
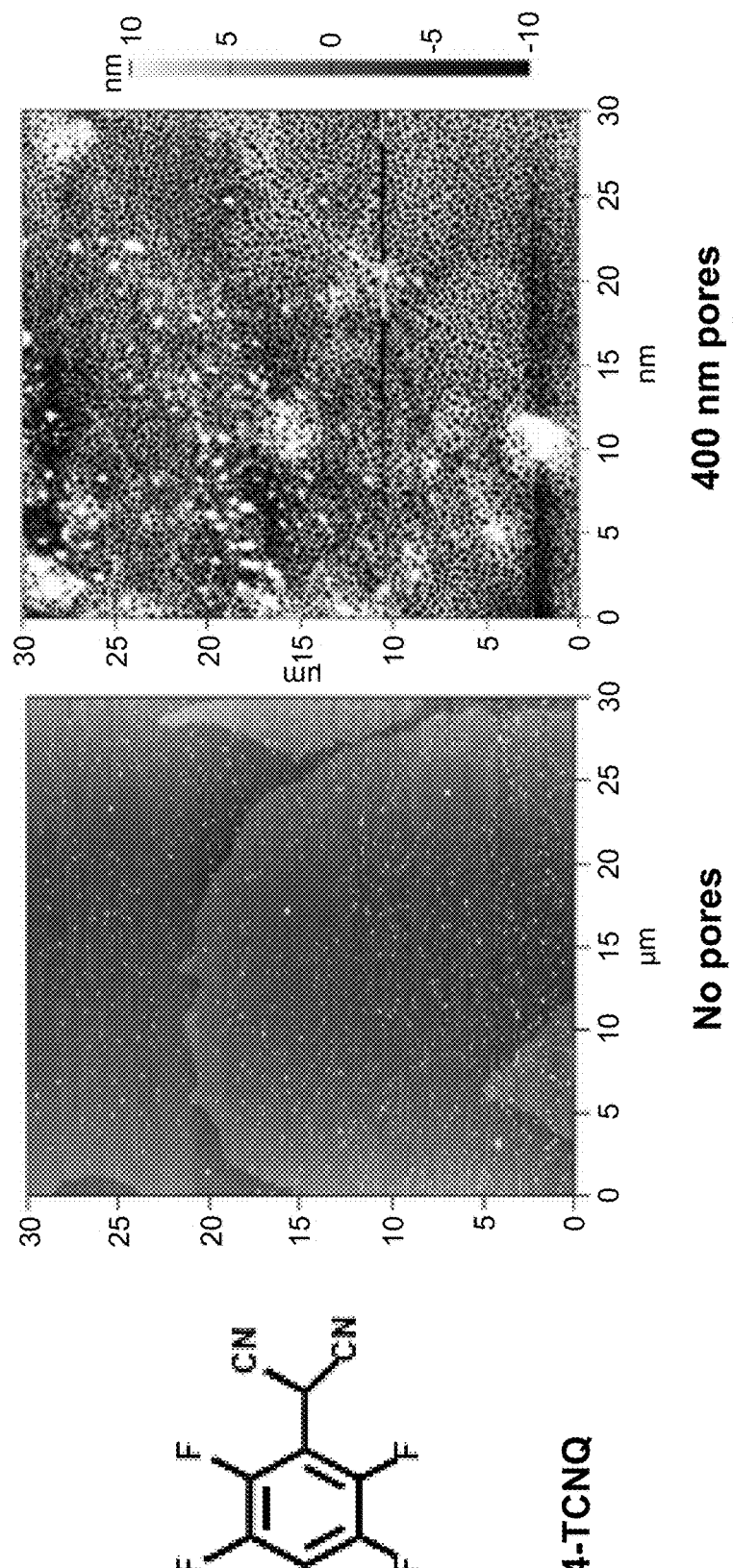
FIG. 42. (a) Molecular structure of F4-TCNQ. (b) AFM images of $F_4$-TCNQ doped $C_8$-BTBT film (left) without and (right) with pores.
Figure 42:
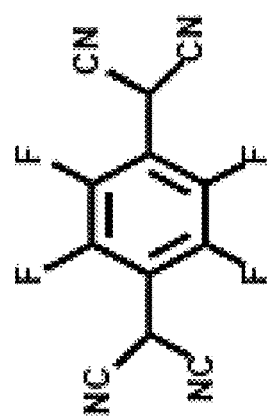

To test feasibility for breath sensing, we collected breath samples from a healthy female (age of 27) and simulated disease conditions by adding ammonia at a series of concentrations. The exhaled breath sample contains a mixture of water vapor, carbon oxide, oxygen and thousands of VOCs. For the as-collected breath sample, the DPP-TT OFET sensors showed a positive response with an increase in current (FIG. 5e). Repeated tests over a period of two weeks (sample collected at the same hour of the day) established a stable baseline and range of fluctuations of current responses to healthy breath for this individual (FIG. 5f and FIG. 32). We note that such stable response is attributed to the excellent stability of the fabricated DPP-TT transistor devices. For the simulated disease condition with higher than usual ammonia concentrations, we observed current responses clearly distinguishable from the healthy condition, even at an ammonia concentration as low as 10 ppb (FIG. 5e and FIG. 33). Specifically, at 1 ppm—a disease relevant ammonia concentration level, we observed a ~50% current change compared to the healthy condition, which was well beyond the baseline fluctuations (FIG. 5f). In addition, across the wide range of concentrations tested, the magnitude of current response was fully consistent with the case when air was used as the carrier gas as opposed to the healthy breath sample (FIG. 34). In the practical application for breath testing, the temperature and humidity of breath gases are always controlled to minimize their effects during direct breath sampling due to the inter-individual fluctuations. For instance, humidity level in the breath samples significantly influence the precious VOCs monitoring. Pre-cooled or pre-dried the exhaled gases are always used in the breath analysis. Hence, we measured current response for dried gas samples. As shown in FIG. 35, the extra $NH_3$ can be distinguished from the health condition after drying the samples.

Example 6. HDA Decreases the Miscibility of PVP with THF

We infer that addition of HDA decreases the miscibility of PVP with THF. This inference is made on the following basis: 1) HDA interacts with THF more favorably as compared to PVP with THF, as evidenced by the much smaller HDA-THF distance as compared to the PVP-THF distance. 2) HDA interacts with THF more favorably as compared to with PVP:HDA, as evidenced by smaller HDA-THF distance compared to the HDA—PVP:HDA distance. Thereafter, we prepared saturated PVP-HTA solution with and without HDA. As shown in FIG. 7, the solution is transparent for PVP-THF solution without and with 5 wt. % HDA; when the concentration of HDA increases to 15 wt. %, the precipitation can be observed in the solution; further increasing the addition of HDA, the solution becomes opaque, which is agree with the mechanism that addition of HDA induce microphase separation in the PVP-THF solution. These conditions suggest THF/HDA solution to be phase separated from the crosslinked PVP:HDA phase with increasing HDA concentration.

Example 7. Methods

Nanoporous Device Fabrication.

Heavily doped silicon wafer (n-type) with a thermally grown $SiO_2$ (300 nm) were used as bottom-gate electrode and the dielectric layer, respectively. The substrates were rinsed with toluene, acetone, and isopropyl alcohol, and dried with nitrogen before deposition of the organic materials. Poly-4-vinylphenol (PVP, $M_w$=25000 mg/mL, Sigma-Aldrich) solution was spin-coated on the substrate at a rotation speed of 7000 rpm for fabricating the porous template. The solutions of PVP were prepared with 4,4'-(hexafluoroisopropylidene)diphthalic anhydride (HDA, Sigma-Aldrich) in a series PVP:HDA ratio of 10:1 to 1:1 by weight in tetrahydrofuran (THF, Sigma-Aldrich). The concentrations of PVP range from 2.5 mg/mL to 20 mg/mL. Prior to spin-coating, the substrates were treated with plasma (Plasma Etch Inc. PE-25) for 6 min at 150 W. To obtain the porous structure, the humidity needs to be kept at 50% during the preparing process. Subsequently, the modified layer was cured at 100° C. in air for 1 hr. For the nanoporous sensors fabrication, the templates were fabricated following the procedure above with PVP at a concentration of 5.5 mg/mL. After plasma treated for 12 s, the substrates were modified an octadecyltrichlorosilane (OTS, Sigma-Aldrich) assembly layer via vapor method.

OSC layers were deposited via meniscus-guided printing and spin-coating. The printing conditions were as the following: a silicon wafer with 300 nm $SiO_2$ treated with a monolayer of OTS was used as the printing blade; the gap distance between the substrate and the blade was set as 100 µm; the blade was titled by 7°; the substrate was kept at 25° C. A 3 mg/mL DPP-TT/chloroform solution was used to deposit OSC films on the OTS modified template substrates, at printing speed of 0.5 mm/s. For $C_8$-BTBT, the thin film was deposited on the PVP:HDA template layer (without OTS) from 7.5 mg/mL chloroform solution at printing speed of 1 mm/s. In the spin-coating process, a DPP-TT/chlorobenzene solution (5 mg/mL) was dispensed on the substrate when the spin-coater motor was operating at a speed of 4000 rpm. The resulting DPP-TT film thickness was ~23 nm. $C_8$-BTBT/o-dichlorobenzene solution (5 mg/mL) was utilized to fabricate thin films by an off-center spin-coating method, wherein the substrate was offset from the center of the spin-coater.

Finally, gold source and drain electrodes (35 nm) were deposited on the DPP-TT thin film by vacuum evaporation through a shadow mask with a channel and width of 60 μm and 4500 μm respectively, while silver (35 nm) were thermally evaporated on $C_8$-BTBT surface as source and drain electrodes with the same pattern structure. The deposition rate was 0.5 Å/s. For formaldehyde sensor, polyethyleneimine (PEI)/water solution (Sigma-Aldrich, 0.2 mg/mL) was spin coated on the top of $C_8$-BTBT devices when the spin coater was rotated at a speed of 5000 rpm.

Fabrication of flexible devices. For flexible-sensor fabrication, the indium tin oxide (ITO) coated polyethylene terephthalate (PET) substrate (0.127 mm in thickness, Sigma-Aldrich) was cleaned with toluene, acetone and isopropyl alcohol. The substrate was treated with plasma for 6 min at 150 W, and the PVP:HDA solution (with a weight ratio of 10:1 in propylene glycol monomethyl ether acetate) was then utilized to fabricate the dielectric layer as previous reported (Roberts et al., Chem. Mater., 2009, 21, 2292-2299). Following heat treatment at 100° C. for 1 hr on the hot plate in air, the porous PVP:HDA template layer was spin-coated as described above. After the deposition of an OTS monolayer, DPP-TT (5 mg/mL, chloroform) solution was then printed onto the substrate at a speed of 0.5 mm/s. The patterned Au source-drain electrodes were finally thermally deposited onto the film with a thickness of 35 nm.

Film Characterizations.

The surface morphology and thickness of the modified layer and semiconducting layer were characterized with Asylum Research Cypher (Asylum Research) under the tapping mode. Synchrotron-based Grazing-incidence X-ray diffraction (GIXD) were performed at the small-wide-angle X-ray scattering beamline 8ID-E at the Argonne National Laboratory. For GIXD measurement, DPP-TT and $C_8$-BTBT were deposited on the pre-coated PVP:HDA template layer (with and without pores) via spin-coating and printing method. The substrate used for the samples was silicon wafers with 300 nm $SiO_2$. During the measurement, the samples were placed in a helium chamber. The sample to the Pilatus 1M detector distance was 208 mm, and the incidence angle was 0.2°. The X-ray beam energy was 7.35 keV, corresponding to a wavelength of 1.6868 Å. Integration of the diffraction peak areas was performed with the software GIXSGUI. To analyze the domain orientation, pole figures were constructed by extracting (010) π-π stacking peak intensities as a function of the pole angle χ, which are shown in FIG. 2g and FIG. 13. The χ range was divided into 5° segments between 12.5° and 87.5°. To remove the strong background scattering from the underlying template layer, we performed careful peak deconvolution to extract the π-π stacking peak intensity. Multipeak fitting was performed on intensity vs. q curve of each segments to deconvolute the π-π stacking peak from the amorphous ring and the background scattering. The peak area was further normalized by film thickness and exposure time. The normalized intensity was further geometrically corrected to plot FIG. 2g.

Electrical Characterization of Transistor Devices.

The OFET measurements were carried out in ambient air using an Agilent B1500A semiconductor parameter analyzer (Keysight) at room temperature. The mobilities were calculated from the equation $I_{DS}=(\mu W C_{eq}/2L)(V_{GS}-V_T)^2$, where $I_{DS}$ represent the source-drain current, μ is the mobility, W and L are the channel width and length, $C_{eq}$ is the capacitance per unit area of the substrate, $V_{GS}$ and $V_T$ are the gate voltage and threshold voltage, respectively. To measure $C_{eq}$, a metal-dielectric layer-metal structure devices were constructed. The Agilent B1500A was used to carry out the Quasi-Static Capacitance Voltage (QSCV) measurement.

A PDMS micro-flow cell was laminated on the top of the OFET with part of the electrodes exposed to serve as a gas chamber. A two-syringe push-pull syringe pump was connected to the flow cell with inlet and outlet polytetrafluoroethylene tubing. The sensing performance was monitored with the air-diluted analytes at a constant flow speed.

Summary

We demonstrate a simple, additive approach to fabricate nanoporous semiconductor thin films in solution processing. The solution processing methods we used include spin coating and meniscus-guided unidirectional coating; the latter shares the same fundamental physics as large-scale roll-to-roll printing (FIG. 1).

In this work, we achieved porous polymer and small molecular thin film as well as the fine-tuning of pore structure by controlling the template. The morphology and molecular stacking of organic thin films have been determined. With the porous organic thin film, we fabricated and measured the organic field-effect transistor's performance. Based on the electric properties, we obtained an ammonia sensor and a formaldehyde sensor with ultra-high sensitivity and fast response time, which was demonstrated in the application towards breath analysis for healthcare and environment monitoring.

Based on the porous organic thin film, we investigated the chemical doping for both of polymer and small molecule. As shown by the results, the doping induced mobility increase of devices with pores can reach 5 times high compares to the OFETs without pores. The careful modulation of the doping properties of organic thin film can be further used in flexible invertor and organic thermoelectrics as shown in FIG. 2.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A nanoporous semiconducting device comprising:
   a) a substrate having a dielectric layer;
   b) a nanoporous insulating layer comprising one or more insulating polymers that are crosslinked with a cross-linking agent, wherein the weight ratio of the one or more insulating polymers and cross-linking agent is 20:1 to 1:1;

c) a layer comprising an organic semiconductor having a conjugated core, wherein the nanoporous insulating layer and the organic semiconductor comprise a plurality of nanopore channels that have an average pore diameter ranging from 50 nm to about 1500 nm, the conjugated core of the organic semiconductor is oriented parallel to the perimeter of a nanopore channel such that a charge-transfer with an analyte entering the nanopore channel can be facilitated, and the organic semiconductor optionally comprises a small molecule; and d) a coating at the surface of the organic semiconductor comprising a dopant; wherein the plurality of nanopore channels extend from the surface of the organic semiconductor layer, through the nanoporous insulating layer and to the dielectric layer; and wherein the one or more insulating polymers comprise poly(4-vinylphenol) (PVP), the cross-linking agent comprises 4,4'-(hexafluoroisopropylidene) diphthalic anhydride (HDA), the organic semiconductor comprises poly(diketopyrrolopyrrole-thiophene-thieno[3,2,b]thiophene-thiophene) (DPP-TT), and the dopant comprises polyethylenimine (PEI).

2. The device of claim 1, wherein the ratio of PVP to HDA is about 1:1 to about 10:1.

3. The device of claim 1, wherein the organic semiconductor comprises the small molecule wherein the small molecule is a benzothieno[3,2-b]benzothiophene (BTBT), a dinaphthothieno[3,2-b]thiophene (DNTT), a perplene diimide (PDI), a naphthalene diimide (NDI), a quinoidal terthiophene (DQTT), a phenyl-butyric acid methyl ester, a buckminsterfullerene (C60), a pentacene, a rubrene, or a combination thereof.

4. An organic field-effect transistor (OFET) comprising: the nanoporous semiconducting device of claim 1, a source electrode, and a drain electrode, wherein the substrate comprises a bottom-gate electrode.

5. A method of detecting an analyte, the method comprising:

a) exposing the organic field-effect transistor (OFET) of claim 4 to a sample comprising an analyte, wherein the analyte interacts with the pi-electrons of the organic semiconductor, thereby causing a change in current;

b) optionally measuring a baseline current in OFET; and c) detecting a change in the current; wherein a detectable change in current indicates the presence of the analyte, and wherein the analyte is a small molecule or a macromolecule.

6. The method of claim 5 wherein the limit of detection is as low as about 1 part per billion.

7. The method of claim 5 wherein the total surface area of the plurality of nanopore channels in the nanoporous semiconducting device as a fraction of the total surface area of the organic semiconductor layer is proportional to the sensitivity of detection.

8. The method of claim 5 wherein the analyte donates electrons to a p-type nanopore channel to decrease current, the analyte accepts electrons from a p-type nanopore channel to increase current, the analyte donates electrons to a n-type nanopore channel to increase current, or the analyte accepts electrons from an n-type nanopore channel to decrease current.

9. The method of claim 5 wherein the dopant can donate electrons to the organic semiconductor, or accept electrons from the organic semiconductor, thereby forming a charge-transfer complex having a charge carrier concentration at the organic semiconductor.

10. The method of claim 9 wherein the analyte reacts with the dopant thereby changing the charge carrier concentration at the organic semiconductor and changing the source-drain current of the OFET.

11. A method of fabricating the nanoporous semiconducting device of claim 1, the method comprising:

a) coating a substrate with a solution to form a film, wherein the solution comprises one or more insulating polymers, a cross-linking agent, and a porogen for inducing nucleation and pore formation;

b) curing the film to form a microphase separated nanoporous insulating layer on the substrate;

c) optionally modifying the hydrophobicity of the surface of the nanoporous insulating layer; and d) depositing an organic semiconductor on the surface of the nanoporous insulating layer;

wherein steps a-d result in the formation of a nanoporous semiconducting device having a semiconducting surface area that is higher relative to the semiconducting surface area of semiconducting device lacking a plurality of nanopore channels.

12. The method of claim 11 wherein the porogen comprises tetrahydrofuran (THF), propylene glycol monomethyl ether acetate (PGMEA), dimethylformamide (DMF), dimethyl sulfoxide (DMSO), chloroform, chlorobenzene, dichlorobezene, acetone, acetonitrile, ethanol, isopropanol, or a combination thereof.

13. The method of claim 11 wherein coating a substrate with the film is performed by spin coating, drop casting, meniscus guided coating, roll-to-roll printing, flexographic printing, slot-die coating, gravure printing, bar-coating, screen printing, ink-jet printing, pen-writing, spray coating, transfer printing, contact printing, or laser printing.

14. The method of claim 11 wherein the substrate is a flexible substrate, a rigid substrate, or a combination thereof, and wherein the substrate optionally comprises $SiO_2$, $Al_2O_3$, $HfO_2$, $V_2O_5$, $TiO$, an insulating polymer, divinyltetramethyldisiloxane-bis(benzocyclobutene) (BCB), or tetratetracontane.

* * * * *